United States Patent
Hennek et al.

(10) Patent No.: US 11,754,562 B2
(45) Date of Patent: Sep. 12, 2023

(54) METHODS FOR MULTIPLEX IMAGING USING LABELED NUCLEIC ACID IMAGING AGENTS

(71) Applicant: Ultivue, Inc., Cambridge, MA (US)

(72) Inventors: Stephanie Rae Hennek, Medford, MA (US); Mael Manesse, Medford, MA (US); Abdul Mohammed, Cambridge, MA (US); Xi Chen, West Newton, MA (US); Michael Jules Natan, Weston, MA (US)

(73) Assignee: Ultivue, Inc., Cambridge, MA (US)

( * ) Notice: Subject to any disclaimer, the term of this patent is extended or adjusted under 35 U.S.C. 154(b) by 0 days.

(21) Appl. No.: 16/992,654

(22) Filed: Aug. 13, 2020

(65) Prior Publication Data
US 2020/0371097 A1    Nov. 26, 2020

Related U.S. Application Data

(63) Continuation of application No. 16/794,686, filed on Feb. 19, 2020, which is a continuation of application
(Continued)

(51) Int. Cl.
| | | |
|---|---|---|
| *C12Q 1/6804* | (2018.01) | |
| *C12Q 1/6832* | (2018.01) | |
| *C12Q 1/6874* | (2018.01) | |
| *C12Q 1/6806* | (2018.01) | |
| *C12Q 1/6823* | (2018.01) | |

(Continued)

(52) U.S. Cl.
CPC ......... *G01N 33/54386* (2013.01); *C12Q 1/68* (2013.01); *C12Q 1/682* (2013.01); *C12Q 1/6804* (2013.01); *C12Q 1/6806* (2013.01); *C12Q 1/6816* (2013.01); *C12Q 1/6818* (2013.01); *C12Q 1/6823* (2013.01); *C12Q 1/6832* (2013.01); *C12Q 1/6874* (2013.01); *G01N 33/543* (2013.01); *G01N 33/54306* (2013.01);
(Continued)

(58) Field of Classification Search
CPC ........ C12Q 1/6804; C12Q 1/682; C12Q 1/68; C12Q 1/6806; C12Q 1/6816; C12Q 2537/143; C12Q 2563/179
See application file for complete search history.

(56) References Cited

U.S. PATENT DOCUMENTS

| | | |
|---|---|---|
| 5,047,523 A | 9/1991 | Woods et al. |
| 5,403,711 A | 4/1995 | Walder et al. |

(Continued)

FOREIGN PATENT DOCUMENTS

| | | |
|---|---|---|
| DE | 4421891 A1 | 1/1996 |
| EP | 868530 A1 | 10/1998 |

(Continued)

OTHER PUBLICATIONS

Bruno et al., "Analysis of AtGUS1 and AtGUS2 in *Arabidopsis* root apex by a highly sensitive TSA-MISH method," Int. J. Dev. Biol., vol. 59, pp. 221-228. (Year: 2015).*

(Continued)

*Primary Examiner* — Young J Kim
(74) *Attorney, Agent, or Firm* — McNeill Baur PLLC

(57) ABSTRACT

The present application provides certain advantageous ways of conducting multiplexed imaging.

15 Claims, 23 Drawing Sheets
(4 of 23 Drawing Sheet(s) Filed in Color)

Related U.S. Application Data

No. 15/836,322, filed on Dec. 8, 2017, now abandoned.

(60) Provisional application No. 62/445,896, filed on Jan. 13, 2017, provisional application No. 62/432,511, filed on Dec. 9, 2016.

(51) Int. Cl.
| | |
|---|---|
| *G01N 33/543* | (2006.01) |
| *G01N 33/58* | (2006.01) |
| *C12Q 1/68* | (2018.01) |
| *C12Q 1/6818* | (2018.01) |
| *C12Q 1/6816* | (2018.01) |
| *C12Q 1/682* | (2018.01) |

(52) U.S. Cl.
CPC ....... *G01N 33/54333* (2013.01); *G01N 33/58* (2013.01); *G01N 33/587* (2013.01)

(56) References Cited

U.S. PATENT DOCUMENTS

| | | |
|---|---|---|
| 6,083,486 A | 7/2000 | Weissleder et al. |
| 6,150,173 A | 11/2000 | Schubert |
| 6,277,632 B1 | 8/2001 | Harney |
| 6,316,229 B1 | 11/2001 | Lizardi et al. |
| 6,344,329 B1 | 2/2002 | Lizardi |
| 6,511,809 B2 | 1/2003 | Baez et al. |
| 6,531,286 B2 | 3/2003 | Jayasena et al. |
| 6,534,041 B1 | 3/2003 | Licha et al. |
| 6,783,943 B2 | 8/2004 | Christian et al. |
| 6,797,474 B2 | 9/2004 | Lizardi |
| 6,833,246 B2 | 12/2004 | Balasubramanian |
| 6,924,115 B2 | 8/2005 | Schubert |
| 7,371,520 B2 | 5/2008 | Zhao et al. |
| 7,422,855 B2 | 9/2008 | DiCesare |
| 7,553,619 B2 | 6/2009 | Kumar et al. |
| 7,604,981 B1 | 10/2009 | Harris et al. |
| 7,618,776 B2 | 11/2009 | Lizardi |
| 7,629,125 B2 | 12/2009 | Sood et al. |
| 7,767,414 B1 | 8/2010 | Smith et al. |
| 7,838,302 B2 | 11/2010 | Zhuang et al. |
| 7,883,669 B2 | 2/2011 | Sun et al. |
| 8,043,834 B2 | 10/2011 | Abarzúa et al. |
| 8,481,714 B2 | 7/2013 | Fujimoto et al. |
| 8,859,266 B2 | 10/2014 | Gerasimova et al. |
| 9,008,378 B2 | 4/2015 | Micheva et al. |
| 9,578,306 B2 | 2/2017 | Micheva et al. |
| 9,625,387 B2 | 4/2017 | Demos et al. |
| 9,677,131 B2 | 6/2017 | Fredriksson et al. |
| 10,415,080 B2 | 9/2019 | Dunaway et al. |
| 11,021,737 B2 | 6/2021 | Church et al. |
| 2002/0106648 A1 | 8/2002 | Lizardi et al. |
| 2002/0115841 A1 | 8/2002 | Brown et al. |
| 2002/0173053 A1 | 11/2002 | Damaj et al. |
| 2002/0177141 A1 | 11/2002 | Chee et al. |
| 2002/0177149 A1 | 11/2002 | Rimm et al. |
| 2003/0008313 A1 | 1/2003 | Wiltshire |
| 2003/0044353 A1 | 3/2003 | Weissleder et al. |
| 2003/0064398 A1 | 4/2003 | Barnes |
| 2003/0073149 A1 | 4/2003 | Archer et al. |
| 2003/0124595 A1 | 7/2003 | Lizardi |
| 2003/0124629 A1 | 7/2003 | Tse et al. |
| 2003/0175828 A1 | 9/2003 | Lazar |
| 2004/0009612 A1 | 1/2004 | Zhao et al. |
| 2004/0086918 A1 | 5/2004 | Loewy et al. |
| 2004/0121382 A1 | 6/2004 | Liu et al. |
| 2004/0121385 A1 | 6/2004 | Andersson et al. |
| 2004/0137456 A1 | 7/2004 | Yokota et al. |
| 2004/0241759 A1 | 12/2004 | Tozer et al. |
| 2004/0248325 A1 | 12/2004 | Bukusoglu |
| 2005/0026161 A1 | 2/2005 | Jablonski et al. |
| 2005/0074781 A1 | 4/2005 | Schroeder et al. |
| 2005/0169843 A1 | 8/2005 | Weissleder et al. |
| 2005/0171434 A1 | 8/2005 | Madden et al. |
| 2005/0214809 A1 | 9/2005 | Han |
| 2005/0287578 A1 | 12/2005 | Davis |
| 2006/0024695 A1 | 2/2006 | Li et al. |
| 2006/0063196 A1 | 3/2006 | Akeson et al. |
| 2006/0166227 A1 | 7/2006 | Kingsmore et al. |
| 2006/0199216 A1 | 9/2006 | Su et al. |
| 2006/0228733 A1 | 10/2006 | Pierce et al. |
| 2006/0252079 A1 | 11/2006 | Oldham et al. |
| 2006/0292616 A1 | 12/2006 | Neely et al. |
| 2007/0048759 A1 | 3/2007 | Luo et al. |
| 2007/0117109 A1 | 5/2007 | Rothemund |
| 2007/0166709 A1 | 7/2007 | McCreavy et al. |
| 2008/0032307 A1 | 2/2008 | Buzby |
| 2008/0096258 A1 | 4/2008 | Korfhage et al. |
| 2008/0118934 A1 | 5/2008 | Gerdes et al. |
| 2008/0152207 A1 | 6/2008 | Micheva et al. |
| 2008/0269068 A1 | 10/2008 | Church et al. |
| 2008/0287668 A1 | 11/2008 | Toth-Fejel |
| 2009/0004749 A1 | 1/2009 | Yamagata et al. |
| 2009/0011956 A1 | 1/2009 | Yin et al. |
| 2009/0111094 A1 | 4/2009 | Storhoff et al. |
| 2010/0015607 A1 | 1/2010 | Geiss et al. |
| 2010/0055685 A1 | 3/2010 | Saul |
| 2010/0069621 A1 | 3/2010 | Maune et al. |
| 2010/0081134 A1 | 4/2010 | Mirkin et al. |
| 2010/0216978 A1 | 8/2010 | Shih |
| 2010/0304994 A1 | 12/2010 | Wu et al. |
| 2011/0039304 A1 | 2/2011 | Church et al. |
| 2011/0223585 A1 | 9/2011 | Gullberg et al. |
| 2012/0004132 A1 | 1/2012 | Zhang et al. |
| 2012/0022244 A1 | 1/2012 | Yin |
| 2012/0178081 A1 | 7/2012 | Nguyen et al. |
| 2012/0252685 A1 | 10/2012 | Treynor et al. |
| 2013/0040840 A1 | 2/2013 | Huang et al. |
| 2013/0072390 A1 | 3/2013 | Wang et al. |
| 2013/0123121 A1 | 5/2013 | Schwartz et al. |
| 2013/0237437 A1 | 9/2013 | Russell et al. |
| 2013/0261019 A1 | 10/2013 | Lin et al. |
| 2013/0288249 A1 | 10/2013 | Gullberg et al. |
| 2013/0323729 A1 | 12/2013 | Landegren et al. |
| 2013/0344500 A1 | 12/2013 | Trautman et al. |
| 2014/0030705 A1 | 1/2014 | Deshpande et al. |
| 2014/0038201 A1 | 2/2014 | Zhuang et al. |
| 2014/0194311 A1 | 7/2014 | Gullberg et al. |
| 2014/0349288 A1 | 11/2014 | Church et al. |
| 2015/0267251 A1 | 9/2015 | Cai et al. |
| 2016/0002704 A1 | 1/2016 | Diehl et al. |
| 2016/0161472 A1 | 6/2016 | Jungmann et al. |
| 2016/0289750 A1 | 10/2016 | Landegren et al. |
| 2016/0319328 A1 | 11/2016 | Yin et al. |
| 2017/0009278 A1 | 1/2017 | Soderberg et al. |
| 2017/0089892 A1 | 3/2017 | Aghvanyan et al. |
| 2017/0101665 A1 | 4/2017 | Banerjee et al. |
| 2017/0107566 A1 | 4/2017 | Church et al. |
| 2017/0159136 A1 | 6/2017 | Church et al. |
| 2017/0168047 A1 | 6/2017 | Aghvanyan et al. |
| 2017/0192013 A1 | 7/2017 | Agresti |
| 2017/0220733 A1 | 8/2017 | Zhuang et al. |
| 2017/0307627 A1 | 10/2017 | Wang et al. |
| 2018/0002736 A1 | 1/2018 | O'Connell et al. |
| 2018/0024139 A1 | 1/2018 | Peikon et al. |

FOREIGN PATENT DOCUMENTS

| | | |
|---|---|---|
| EP | 1915466 B1 | 11/2010 |
| EP | 1563100 B1 | 4/2013 |
| EP | 2369015 B1 | 4/2014 |
| EP | 2818867 A1 | 12/2014 |
| EP | 2593563 B1 | 11/2016 |
| EP | 2633081 B1 | 1/2017 |
| EP | 2627781 B1 | 2/2017 |
| EP | 2714925 B1 | 6/2017 |
| EP | 1771786 B1 | 12/2017 |
| JP | 2003259869 A | 9/2003 |
| JP | 2004512017 A | 4/2004 |
| WO | 0003034 A2 | 1/2000 |
| WO | 0020641 A1 | 4/2000 |
| WO | 0058507 A1 | 10/2000 |

(56) References Cited

FOREIGN PATENT DOCUMENTS

| WO | 2000068434 | A2 | 11/2000 |
|---|---|---|---|
| WO | 2001084146 | A2 | 11/2001 |
| WO | 0197616 | A1 | 12/2001 |
| WO | 02079771 | A1 | 10/2002 |
| WO | 2005017485 | A2 | 2/2005 |
| WO | 2006104979 | A2 | 10/2006 |
| WO | 2007076128 | A3 | 11/2007 |
| WO | 2012054735 | A2 | 4/2012 |
| WO | 2012058638 | A2 | 5/2012 |
| WO | 2013096851 | A1 | 6/2013 |
| WO | 2014028538 | A2 | 2/2014 |
| WO | 2014076214 | A1 | 5/2014 |
| WO | 2014079802 | A2 | 5/2014 |
| WO | 2014130388 | A1 | 8/2014 |
| WO | 2014135838 | A1 | 9/2014 |
| WO | 2014163886 | A1 | 10/2014 |
| WO | 2014182528 | A2 | 11/2014 |
| WO | 2014207245 | A1 | 12/2014 |
| WO | 2015089506 | A2 | 6/2015 |
| WO | 2015128490 | A1 | 9/2015 |
| WO | 2015138653 | A1 | 9/2015 |
| WO | 2016028843 | A2 | 2/2016 |
| WO | 2017143155 | A3 | 9/2017 |
| WO | 2017200870 | A1 | 11/2017 |
| WO | 2018017604 | A1 | 1/2018 |

OTHER PUBLICATIONS

Cao et al., "In-situ Immuno-PCR to detect antigens," The Lancet 356:1002-1003 (2000).

Ke et al., DNA brick crystals with prescribed depths. Nat Chem. Nov. 2014;6(1 1):994-1002. doi: 10.1038/nchem.2083. Epub Oct. 19, 2014.

Ke et al., Self-Assembled Water-Soluble Nucleic Acid Probe Tiles for Label-Free RNA Hybridization Assays. Science. Jan. 11, 2008;319(5860):180-3.

Ke et al., Three-dimensional structures self-assembled from DNA bricks. Science. Nov. 30, 2012;338(6111):1177-83. doi: 10 I 126/science.1227268.

Kuzuya et al., Six-helix and eight-helix DNA nanotubes assembled from half-tubes. Nano Lett. Jun. 2007;7(6):1757-63. Epub May 15, 2007.

Levsky et al., Fluorescence in situ hybridization: past, present and future. J Cell Sci. Jul. 15, 2003;116(Pt 14):2833-8.

Levsky et al., Single-cell gene expression profiling, Science, Aug. 2, 2002; 297(5582):836-40.

Li et al., Controlled fabrication of fluorescent barcode nanorods. ACS Nano. Aug. 24, 2010;4(8):4350-60. doi: 10.1021/nn9017137.

Li et al., Multiplexed detection of pathogen DNA with DNA-based fluorescence nanobarcodes. Nat Biotechnol. Jul. 2005;23(7):885-9. Epub Jun. 12, 2005.

Lichtman et al., Fluorescence microscopy. Nat Methods. Dec. 2005;2(12):910-9.

Lin et al., Designer DNA nanoarchitectures. Biochemistry. Mar. 3, 2009;48(8):1663-74. doi: 10.1021/bi802324w.

Lin et al., Functional DNA nanotube arrays: bottom-up meets top-down. Angewandte Chemie. 2007;119(32):6201-4.

Lin et al., Self-assembled combinatorial encoding nanoarrays for multiplexed biosensing. Nano Lett. Feb. 2007;7(2):507-12.

Lin et al., Submicrometre geometrically encoded fluorescent barcodes self-assembled from DNA. Nat Chem. Oct. 2012;4(10):832-9.

Liu et al., Aptamer-directed self-assembly of protein arrays on a DNA nanostructure. Angew Chem Int Ed Engl. Jul. 11, 2005;44(28):4333-8.

Livet et al., Transgenic strategies for combinatorial expression of fluorescent proteins in the nervous system. Nature. Nov. 1, 2007;450(7166):56-62.

Lubeck et al., "Single-cell in situ RNA profiling by sequential hybridization," Nature Methods, vol. 11, No. 4, Apr. 2014, pp. 360-361.

Mag et al., Synthesis and selective cleavage of an oligodeoxynucleotide containing a bridged internucleotide 5'-phosphorothioate linkage. Nucleic Acids Res. Apr. 11, 1991;19(7):1437-41.

Marcon et al., 'On-the-fly' optical encoding of combinatorial peptide libraries for profiling of protease specificity. Mol Biosyst. Jan. 2010;6(1):225-33. doi: 10.1039/b909087h. Epub Oct. 6, 2009.

Martin, Functional Synthetic DNA Nanostructures. Dissertation. Technische Universitat Mtinchen, Laboratory for Biomolecular Nanotechnolrn;,:v Filed on Mar. 12, 2013.

Mathieu et al., Six-helix bundles designed from DNA Nano Lett. Apr. 2005;5(4):661-5.

Mei et al., Stability of DNA origami nanoarrays in cell lysate. Nano Lett. Apr. 13, 2011;11(4):1477-82. doi: 10.1021/nll040836. Epub Mar. 2, 2011.

Meserve et al., A double-stranded molecular probe for homogeneous nucleic acid analysis. Analyst. Aug. 2008;l33(8): 1013-9. doi:10.1039/b804853c. Epub Jun. 6, 2008.

Mittag et al., Sequential photobleaching of fluorochromes for polychromatic slide-based cvtometry. Cytometry A. Mar. 2006;69(3):139-41.

Myhrvold et al., Isothermal self-assembly of complex DNA structures under diverse and biocompatible conditions. Nano Lett. Sep. 2013 I 1;13(9):4242-8. doi: 10.1021/nl4019512. Epub Aug. 26, 2013.

Nannenga et al., High-resolution structure determination by continuous-rotation data collection in MicroED. Nat Methods. Sep. 2014;I 1(9):927-30. doi: 10.1038/nmeth.3043. Epub Aug. 3, 2014.

Nannenga et al., Protein structure determination by MicroED. Curr Opin Struct Biol. Aug. 2014;27:24-31. doi: 10.1016/j.sbi.2014.03. 004. Epub Apr. 5, 2014.

New England Biolabs Inc. 2013-14 Catalog and Technical Reference, p. 129 (2013).

Nicewarner-Pena et al., Submicrometer metallic barcodes. Science. Oct. 5, 2001;294(5540):137-41.

Pinheiro et al., Challenges and opportunities for structural DNA nanotechnology. Nat Nanotechnol. Nov. 6, 2011;6(12):763-72. doi:10.1038/nnano.201I.187.

Raj et al., Imaging individual mRNA molecules using multiple singly labeled probes. Nat Methods. Oct. 2008;5(10):877-9. doi: 10.1038/nmeth.1253. Epub Sep. 21, 2008.

Rajendran et al., Selection of fluorescent aptamer beacons that light up in the presence of zinc. Anal Bioanal Chem. Feb. 2008;390(4):1067-75. Epub Nov. 30, 2007.

Resch-Genger et al., Quantum dots versus organic dyes as fluorescent labels. Nat Methods. Sep. 2008;5(9):763-75. doi: 10.1038/nmeth.1248.

Rinker et al., Self-assembled DNA nanostructures for distance-dependent multivalent ligand-protein binding. Nat Nanotechnol. Jul. 2008;3(7):418-22. doi: 10.1038/nnano.2008.164. Epub Jun. 22, 2008.

Rodgers et al., Transient association of Ku with nuclear substrates characterized using fluorescence photobleaching. J Immunol. Mar. 1, 2002;168(5):2348-55.

Rosi et al., Nanostructures in biodiagnostics. Chem Rev. Apr. 2005;105(4):1547-62.

Rothemund, Folding DNA to create nanoscale shapes and patterns. Nature. Mar. 16, 2006;440(7082):297-302.

Sadowski et al., Developmental self-assembly of a DNA tetrahedron. ACS Nano. Apr. 22, 2014;8(4):3251-9. doi:10.1021/nn4038223. Epub Apr. 11, 2014.

Schmied et al., DNA origami-based standards for quantitative fluorescence microscopy. Nat Protoc. 2014;9(6):1367-91. doi: 10.1038/nprot.2014.079. Epub May 15, 2014.

Schmied et al., Fluorescence and super-resolution standards based on DNA origami. Nat Methods. Dec. 2012;9(12):1133-4. doi: 10.1038/nmeth.2254.

Schubert et al., Analyzing proteome topology and function by automated multidimensional fluorescence microscopy. Nat Biotechnol. Oct. 2006;24(10):1270-8. Epub Oct. 1, 2006.

Schweitzer et al., "Immunoassays with rolling circle DNA amplification: A versatile platform for ultrasensitive antigen detection," PNAS, Aug. 29, 2000, vol. 97, No. 18, pp. 10113-10119.

(56) References Cited

OTHER PUBLICATIONS

Schweller et al., Multiplexed in situ immunofluorescence using dynamic DNA complexes. Angew Chem Int Ed Engl. Sep. 10, 2012;5 I (37):9292-6. doi: 10.1002/anie.201204304. Epub Aug. 15, 2012.

Seeman, Nucleic acid junctions and lattices. J Theor Biol. Nov. 21, 1982;99(2):237-47.

Shi et al., Three-dimensional electron crystallography of protein microcrystals. Elife. Nov. 19, 2013;2:e01345. doi:10.7554/eLife.01345.

Shi, A glimpse of structural biology through X-ray crystallography. Cell. Nov. 20, 2014;159(5):995-1014. doi: 10.1016/i.cell.2014.10.051.

Steinhauer et al., DNA origami as a nanoscopic ruler for super-resolution microscopy. Angew Chem Int Ed Engl. 2009;48(47):8870-3. doi: 10.1002/anie.200903308.

Tokunaga et al., Highly inclined thin illumination enables clear single-molecule imaging in cells. Nat Methods. Feb. 2008;5(2):159-61. Epub Jan. 6, 2008.

Torring et al., DNA origami: a quantum leap for self-assembly of complex structures. Chem Soc Rev. Dec. 2011;40(12):5636-46. doi: 10.1039/clcsl5057i. Epub May 19, 2011.

Tsien, The green fluorescent protein. Annu Rev Biochem. 1998;67:509-44.

Wahlby et al., Sequential immunofluorescence staining and image analysis for detection of large numbers of antigens in individual cell nuclei. Cytometry. Jan. 1, 2002;47(1):32-41.

[No Author Listed] DNA origami scaffolds for cryo-EM visualization of membrane associated complexes. University of Michigan. Project ID: 377. Last accessed from http://mcubed.umich.edu/projects/dna-origami-scaffolds-cryo-em-visualization-membrane-associated-complexes on Nov. 12, 2015.

Abulrob et al., Nanoscale imaging of epidermal growth factor receptor clustering: effects of inhibitors J Biol Chem. Jan. 29, 2010;285(5):3145-56. doi: 10.1074/jbc.M109.073338. Epub Dec. 3, 2009.

Agasti et al., DNA-barcoded labeling probes for highly multiplexed Exchange-PAINT imaging. Chem Sci. Apr. 1, 2017;8(4):3080-91. doi: 10.1039/c6sc05420j. Epub Jan. 30, 2017.

Agasti et al., Photocleavable DNA barcode-antibody conjugates allow sensitive and multiplexed protein analysis in single cells. J Am Chem Soc. Nov. 14, 2012;134(45):18499-502. doi: 10.1021/ja307689w. Epub Nov. 2, 2012.

Christensen et al., Role of the Bombyx mori R2 element N-terminal domain in the target-primed reverse transcription (TPRT) reaction. Nucleic Acids Res. Nov. 10, 2005;33(20):6461-8.

Citri et al., EGF-ERBB signalling: towards the systems level. Nat Rev Mol Cell Biol. Jul. 2006;7(7):505-l 6.

Dejneka et al., Rare earth-doped glass micro barcodes. Proc Natl Acad Sci US A Jan. 21, 2003;100(2):389-93. Epub Jan. 6, 2003.

Deng et al., CASFISH: CRISPR/Cas9-mediated in situ labeling of genomic loci in fixed cells. Proc Natl Acad Sci US A. Sep. 22, 2015;112(38):11870-5. doi: 10.1073/pnas.1515692112. Epub Aug. 31, 2015.

Dirks et al., Triggered amplification by hybridization chain reaction. Proc Natl Acad Sci US A Oct. 26, 2004;101(43):15275-8. Epub Oct. 18, 2004.

Douglas et al., DNA-nanotube-induced alignment of membrane proteins for NMR structure determination. Proc Natl Acad Sci US A. Apr. 2007 I 7;104(16):6644-8. Epub Apr. 2, 2007.

Douglas et al., Self-assembly of DNA into nanoscale three-dimensional shapes. Nature. May 21, 2009;459(7245):414-8. doi: 10.1038/nature08016.

Eggeling et al., Photobleaching of Fluorescent Dyes under Conditions Used for Single-Molecule Detection Evidence of Two-Step Photolysis. Anal Chem. Jul. 1, 1998;70(13):2651-9. doi: 10.1021/ac980027p.

Elshal et al., Multiplex bead array assays: performance evaluation and comparison of sensitivity to ELISA. Methods. Apr. 2006;38(4):317-23.

Fournier-Bidoz et al., Facile and rapid one-step mass preparation of quantum-dot barcodes. Angew Chem Int Ed Engl. 2008;47(30):5577-81. doi: 10.1002/anie.200800409.

Geiss et al., Direct multiplexed measurement of gene expression with color-coded probe pairs. Nat Biotechnol. Mar. 2008;26(3):317-25. doi: 10.1038/nbtl385. Epub Feb. 17, 2008.

Gerdes et al., Highly multiplexed single-cell analysis of formalin-fixed, paraffin-embedded cancer tissue. Proc Natl Acad Sci US A Jul. 16, 2013;110(29):11982-7. doi:10.1073/pnas.1300136110. Epub Jul. 1, 2013.

Ghauharali et al., Fluorescence photobleaching-based image standardization for fluorescence microscopy. J Microscopy. May 2000;l98(2):88-100.

Gibriel, Options available for labelling nucleic acid samples in DNA microarray-based detection methods. Briefings in Functional Genomics Apr. 17, 2012;11(4):311-8. doi: 10.1093/bfgp/els015.

Giepmans et al., The fluorescent toolbox for assessing protein location and function. Science. Apr. 14, 2006;312(5771):217-24.

Gietl et al., DNA origami as biocompatible surface to match single-molecule and ensemble experiments. Nucleic Acids Res. Aug. 2012;40(14):el 10. doi: 10.1093/nar/gks326. Epub Apr. 20, 2012.

Goncalves MS, Fluorescent labeling of biomolecules with organic probes. Chem Rev. Jan. 2009;l09(1):190-212. doi:10.1021/cr0783840.

Gudiksen et al., Growth of nanowire superlattice structures for nanoscale photonics and electronics. Nature. Feb. 7, 2002;415(6872):617-20.

Guo et al., Four-color DNA sequencing with 3'-0-modified nucleotide reversible terminators and chemically cleavable fluorescent dideoxynucleotides. Proc Natl Acad Sci US A Jul. 8, 2008;105(27):9145-50. doi: 10.1073/pnas.0804023105. Epub Jun. 30, 2008.

Gusev et al., "Rolling Circle Amplification: A New Approach to Increase Sensitivity for Immunohistochemistry and Flow Cytometry," American Journal of Pathology, vol. 159, No. 1, Jul. 2001.

Gustafsson et al., Three-dimensional resolution doubling in wide-field fluorescence microscopy by structured Illumination. Biophys J. Jun. 2008;94(12):4957-70. doi: 10.1529/biophysj.107.120345. Epub Mar. 7, 2008.

Ha et al., Photophysics of fluorescent probes for single-molecule biophysics and super-resolution imaging. Annu Rev Phys Chem. 2012;63:595-617. doi: 10. I 146/annurev-physchem-032210-103340. Epub Jan. 30, 2012.

Han et al., Quantum-dot-tagged microbeads for multiplexed optical coding of biomolecules. Nat Biotechnol. Jul. 9, 2001;(7):631-5.

Huang et al., Selective photothermal therapy for mixed cancer cells using aptamer-conjugated nanorods. Langmuir. Oct. 21, 2008;24(20):11860-5. doi: 10.1021/la801969c. Epub Sep. 26, 2008.

International Search Report and Written Opinion issued in corresponding Application No. PCT/US2017/065362, dated Feb. 16, 2018, 14 pages.

Jenner et al., Crystal structure of the 80S yeast ribosome. Curr Opin Struct Biol. Dec. 2012;22(6):759-67. doi:10.1016/j.sbi.2012.07.013. Epub Aug. 8, 2012. Review.

Jones et al., Nanomaterials. Programmable materials and the nature of the DNA bond. Science. Feb. 20, 2015;347(6224):1260901. doi:I0.1126/science.1260901.

Joo et al., Advances in single-molecule fluorescence methods for molecular biology. Annu Rev Biochem. 2008;77:51-76. doi:10.1 146/annurev.biochem.77.070606.101543.

Ju et al., Four-color DNA sequencing by synthesis using cleavable fluorescent nucleotide reversible terminators. Proc Natl Acad Sci US A Dec. 26, 2006;103(52):19635-40. Epub Dec. 14, 2006.

Jungmann et al., Single-Molecule Kinetics and Super-Resolution Microscopy by Fluorescence Imaging of Transient Binding on DNA Origami. Nano Lett. 2010, 10(11), pp. 4756-4761, doi:10.1021/nl103427w.

Jungmann et al., Multiplexed 3D cellular super-resolution imaging with DNA-PAINT and Exchange-PAINT. Nat Methods. Mar. 2014;11(3):313-8. doi: 10.1038/nmeth.2835. Epub Feb. 2, 2014. Supplementary Text and Figures; 38 pages. XP-002775144.

(56) References Cited

OTHER PUBLICATIONS

Jungmann et al., Nanoscale imaging in DNA nanotechnology. Wiley Interdiscip Rev Nanomed Nanobiotechnol. Jan.-Feb. 2012;4(1):66-81. doi:10.1002/wnan. I 73. Epub Nov. 23, 2011.
Kalies et al., Mechanisms of high-order photobleaching and its relationship to intracellular ablation. Biomed Opt Express. Mar. 4, 2011;2(4):805-16. doi:10.1364/BOE.2.000816.
Kao et al., Tracking of single fluorescent particles in three dimensions: use of cylindrical optics to encode particle position. Biophys J. Sep. 1994;67(3):1291-300.
Kato et al., High-resolution structural analysis of a DNA nanostructure by cryoEM. Nano Lett. Jul. 2009;9(7):2747-50. doi: 10.1021/nl901265n.
Blokzijl et al., "Protein biomarker validation via proximity litigation assays," Biochemica et Biophysica Acta 1844(5):933-939 (2013).
Dixon et al., "Recent developments in multiplexing techiniques for immunnohistochemistry," Expert Review of Molecular Diagnostics 15(9):1171-1186 (2015).
Extended European Search Report issued in European Application No. 17878526.7, dated Oct. 12, 2020, 9 pages.
HinP1I product information [retrieved on-line, retrieval date Oct. 7, retrieved from: https://www.neb.com/products/r0124-hinp1#ProductInformation]. (Year: 2020).
Leuchowius et al., "Parallel Visualization of Multiple Protein Complexes in Individual Cells in Tumor Tissue," Molecular & Cellular Proteomics 12(6):1563-1574 (2013).
Mignardi, "In situ Sequencing—Methods for spatially-resolved transcriptome analysis," 49 pages (2014), retrieved from the internet: URL:https://www.diva-portal.org/smash/get/diva2:768864/FULLTEXT01.pdf.
NEB restriction map [retrieved on-line, retrieval date Oct. 7, retrieved from: http://nc2.neb.com/NEBcutter2/] (Year: 2020).
Wang et al., Prototyping nanorod control: A DNA double helix sheathed within a DNA six-helix bundle. Chem Biol. Aug. 28, 2009;16(8):862-7. doi: 10.1016/j.chembiol.2009.07.008.
Warford et al., "Antigen retrieval, blocking, detection and visualisation systems in immunohistochemistry: A review and practical evaluation of tyramide and rolling circle amplification systems," Methods 70:28-33 (2014).
Weiss, Fluorescence spectroscopy of single biomolecules. Science. Mar. 12, 1999;283(5408):1676-83.
Wilner et al., Covalently linked DNA nanotubes. Nano Lett. Apr. 14, 2010;10(4):1458-65.
Winfree et al., Design and self-assembly of two-dimensional DNA crystals. Nature. Aug. 6, 1998;394(6693):539-44.
Wlodawer et al., Protein crystallography for aspiring crystallographers or how to avoid pitfalls and traps in macromolecular structure determination. FEES J. Nov. 2013;280(22):5705-36. doi:10.1111/febs.12495. Epub Sep. 18, 2013.
Xiao et al., Direct determination of haplotypes from single DNA molecules. Nat Methods. Mar. 2009;6(3):199-201. doi:10.1038/nmeth.1301. Epub Feb. 8, 2009.
Xu et al., Multiplexed SNP genotyping using the Qbead system: a quantum dot-encoded microsphere-based assay. Nucleic Acids Res. Apr. 15, 2003;31(8):e43.
Yang et al., Nanostructures as Programmable Biomolecular Scaffolds. Bioconjug Chem. Aug. 19, 2015;26(8):1381-95. doi:10.1021/acs.bioconjchem.5b00194. Epub May 22, 2015.
Yin et al., Programming biomolecular self-assembly pathways. Nature. Jan. 2008 I 7;451(7176):318-22. doi:10.1038/nature0645 I.
Yin et al., Programming DNA tube circumferences. Science. Aug. 8, 2008;321(5890):824-6. doi:10.1 126/science.1157312.
Yurke et al., A DNA-fuelled molecular machine made of DNA. Nature. Aug. 11, 2000;406(6796):605-8.
Zhang et al., Dynamic DNA nanotechnology using strand-displacement reactions. Nat Chem. Feb. 2011;3(2):103-13. doi: 10.1038/nchem.957.
Zhang et al., Structural DNA nanotechnology: state of the art and future perspective. J Am Chem Soc. Aug. 13, 2014;136(32): 11198-211. do:10.1021/ia50510la. Epub Jul. 28, 2014.
Zhao et al., Advances of multiplex and high throughput biomoelecular detection technologies based on encoding microparticles. Science China Chemistry. 2011;54(8):1185-1201.
Zheng et al., From molecular to macroscopic via the rational design of a self-assembled 3D DNA crystal. Nature. Sep. 3, 2009;461(7260):74-7. doi:10.1038/nature08274.
Zhou et al., "In Situ Detection of Messenger RNA Using Digoxigenin-Labeled Oligonucleotides and Rolling Circle Amplification," Experimental and Molecular Pathology 70, 281-288 (2001).
Koos et al., "Analysis of Protein Interactions in situ by Proximity Ligation Assays," Current Topics in Microbiology and Immunology, pp. 1-17 (2013).
Lyamichev et al., "Polymorphism identification and quantitative detection of genomic DNA by invasive cleavage of oligonucleotide probes," Nature Biotechnology 17:292-296 (1999).
Anderson et al., Improved fluoroimmunoassays using the dye Alexa Fluor 647 with the RAPTOR, a fiber optic biosensor. J Immunol Methods. Dec. 20, 2002;271(1-2):17-24.
Asanuma et al., Enantioselective Incorporation of Azobenzenes into Oligodeoxynbonucleotide tor Effective Photoregulation of Duplex Formation This work was partially supported by a Grant-in-Aid for Sdentific Research from the Ministry of Education, Culture, Sports, Science and Technology, Japan (Molecular Synchronization for Design of New Materials System). The support by the Grant from "Research for the Future" Program of the Japan Society for the Promotion of Science JSPS-RFTF97I0030I) is also acknowledged .. Angew Chem Int Ed Engl. Jul. 16, 2001;40, 2671-2673.
Averbuch et al., Two Linear Unmixing Algorithms to Recognize Targets Using Supervised Classification and Orthogonal Rotation in Airborne Hyperspectral Images. Remote Sens.2012;4(2):532-60.
Bai et al., Cryo-EM structure of a 3D DNA-origami object. Proc Natl Acad Sd US A Dec. 4, 2012;109(49):20012-7. doi:10.1073/pnas.1215713109. Epub Nov. 19, 2012.
Beliveau et al., Versatile design and synthesis platform for visualizing genomes with Oligopaint FISH probes. Proc Natl Acad Sci US A Dec. 26, 2012;109(52):21301-6. doi: 10.1073/pnas.1213818110. Epub Dec. 11, 2012.
Ben-Shem et al., The structure of the eukaryotic ribosome at 3.0 A resolution. Science. Dec. 16, 2011;334(6062):1524-9. doi: 10.1126/science.1212642. Epub Nov. 17, 2011.
Braeckmans et al., Encoding microcarriers by spatial selective photobleaching. Nat Mater. Mar. 2003;2(3):169-73.
Chapman et al., Femtosecond X-ray protein nanocrystallography. Nature. Feb. 3, 2011;470(7332):73-7. doi: 10.1038/nature09750.
Cheng et al., A primer to single-partide cryo-electron microscopy. Cell. Apr. 23, 2015;161(3):438-49. doi:10.1016/j.cell.2015.03.050.
Chhabra et al., DNA self-assembly for nanomedidne. Adv Drug Deliv Rev. Apr. 30, 2010;62(6):617-25. doi: 10.1016/j.addr.2010.03.005. Epub Mar. 15, 2010.
Choi et al., Next-generation in situ hybridization chain reaction: higher gain, lower cost, greater durability. ACS Nano. May 27, 2014;8(5):4284-94. doi: 10.1021/nn405717p. Epub Apr. 8, 2014.
A capture of a webpage available at https://ultivue.com/about-US/ retrieved Nov. 14, 2022.
A capture of a webpage available at https://ultivue.com/assay-development/ retrieved Nov. 14, 2022.
A capture of a webpage available at https://ultivue.com/spatial-phenomics/ retrieved Nov. 14, 2022.
Fakruddin et al., "Nucleic acid amplification: Alternative methods of polymerase chain reaction," Journal of Pharmacy and Bioallied Sciences 5(4):245-252 (2013).
Ke et al., "In situ sequencing for RNA analysis in preserved tissue and cells," Nat. Methods 10(9):857-60 (2013).
Larsson et al., "In situ genotyping individual DNA molecules by target-primed rolling-circle amplification of padlock probes," Nat. Methods 1(3):227-232 (2004).
Lee et al., "Highly multiplexed subcellular RNA sequencing in situ," Science 343(6177):1360-1363 (2014).
Tan et al., "Overview of multiplex immunohistochemistry/immunofluorescence techniques in the era of cancer Immunotherapy," Cancer Communications 40:135-153 (2020).

* cited by examiner

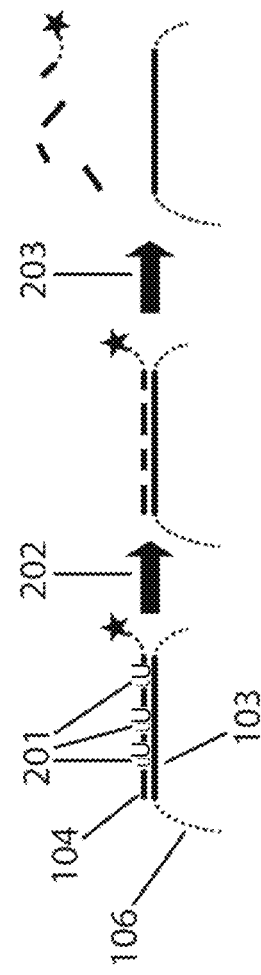
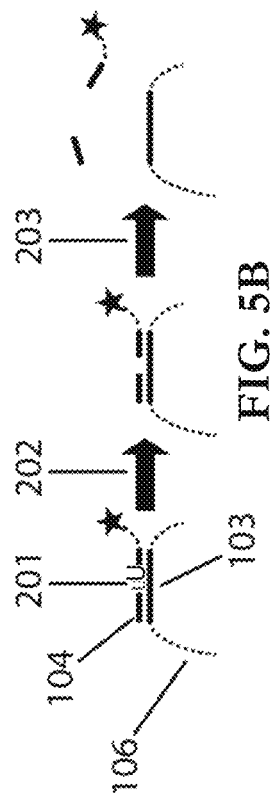
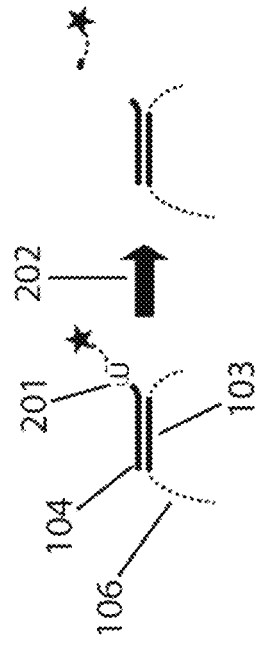
FIG. 5B
FIG. 5C
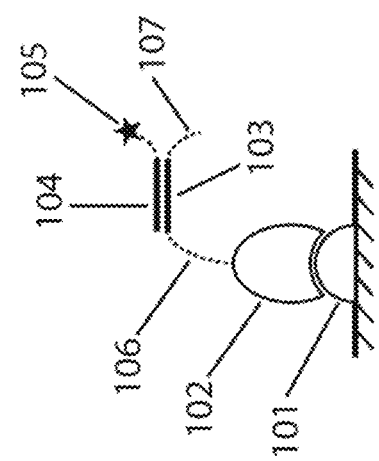
FIG. 5D
FIG. 5A

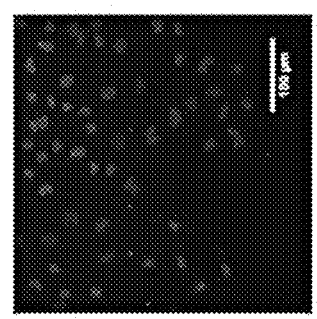
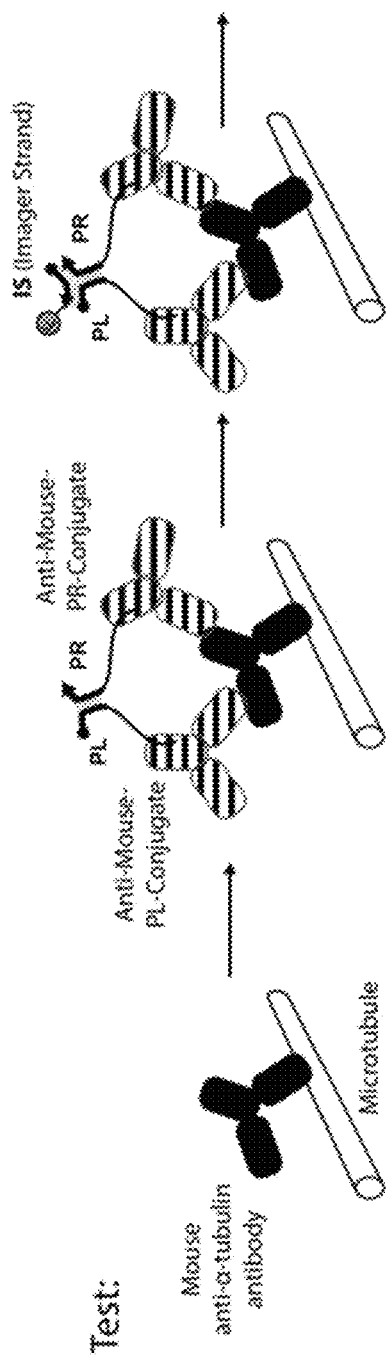
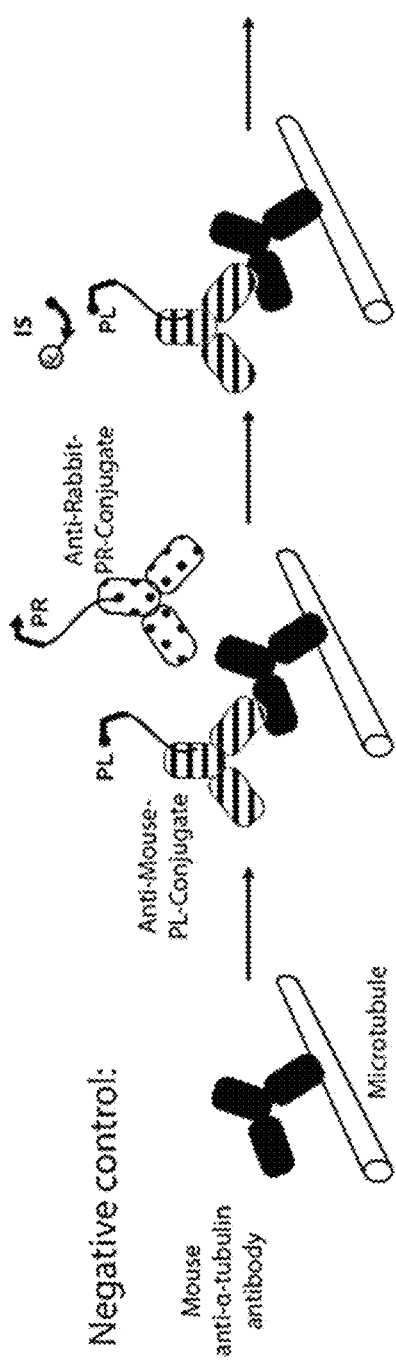
FIG 10A
FIG 10B

FIG. 14A
FIG. 14B
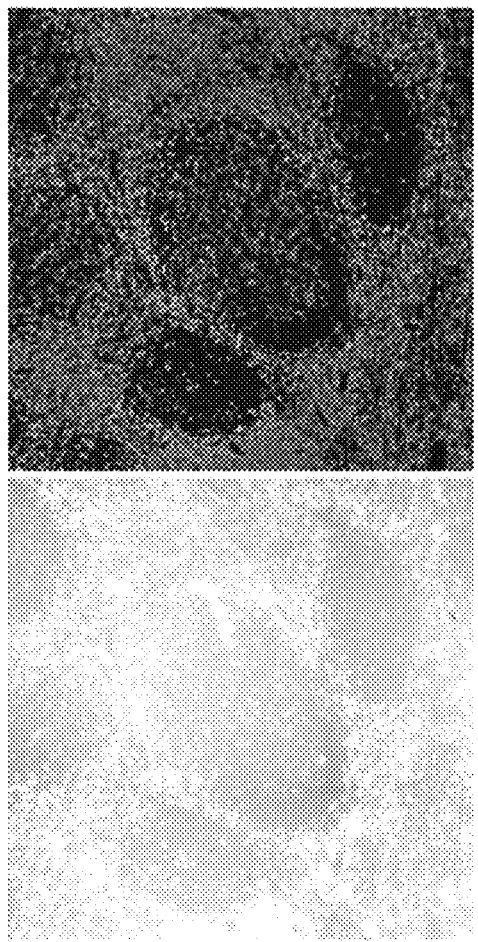
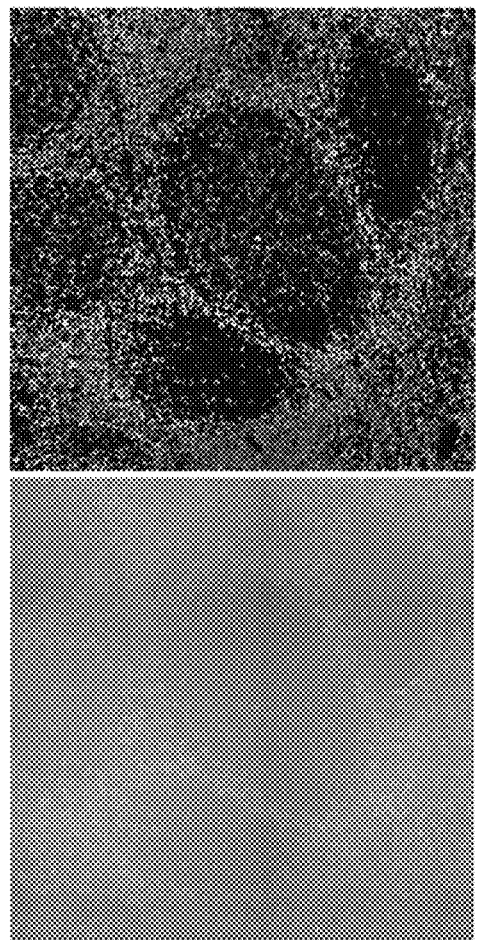
FIG. 14C
FIG. 14D

METHODS FOR MULTIPLEX IMAGING USING LABELED NUCLEIC ACID IMAGING AGENTS

This application is a continuation of U.S. application Ser. No. 16/794,686, filed Feb. 19, 2020, which is a continuation of U.S. application Ser. No. 15/836,322, filed Dec. 8, 2017, which claims the benefit of U.S. Provisional Application No. 62/432,511, filed Dec. 9, 2016, and U.S. Provisional Application No. 62/445,896, filed Jan. 13, 2017, the contents of each of which are incorporated by reference herein in their entirety for any purpose.

DESCRIPTION

Field

This application relates generally to the field of detection and quantification of analytes (e.g., targets).

Background

Fluorescence microscopy is a powerful tool for exploring molecules in, for example, a biological system. However, the number of distinct species that can be distinguishably and simultaneously visualized (i.e. the multiplexing power) is limited by the spectral overlap between the fluorophores. Some multiplexed imaging methods are known, but may not adequately produce a strong enough signal or may require specific means of switching between targets being imaged. Thus, there is a need for new and improved multiplexed imaging methods employing improved amplification methods and additional means of switching between targets being imaged.

SUMMARY

In accordance with the description, in some embodiments, a method to test a sample for the presence of one or more targets comprises:
- (1) contacting a sample being tested for the presence of one or more targets with one or more target-specific binding partners, wherein each target-specific binding partner is linked to a nucleic acid strand and wherein target-specific binding partners of different specificity are linked to different nucleic acid strands,
- (2) optionally removing unbound target-specific binding partners,
- (3) contacting the sample with a nonlinear amplifier strand having complementarity to a nucleic acid strand, wherein the nucleic acid strand is either a docking strand or a primer strand,
- (4) optionally removing unbound nonlinear amplifier strands,
- (5) in either one or two steps amplifying the docking strand with rolling circle amplification and contacting the sample with labeled imager strands having complementarity to the docking strand or amplified strand,
- (6) imaging the sample to detect bound labeled imager strands,
- (7) removing the bound labeled imager strands, and
- (8) optionally repeating steps (1)-(8), or any subset thereof.

In some embodiments, a method to test a sample for the presence of one or more targets comprises:
- (1) contacting the sample with one or more target-specific binding partners, wherein each target-specific binding partner is linked to a nucleic acid strand, directly or indirectly, and wherein target-specific binding partners of different specificity are linked to different nucleic acid strands,
- (2) optionally removing unbound target-specific binding partners,
- (3) wherein the nucleic acid strand is a docking strand or a primer strand and if the nucleic acid is
  - (a) a docking strand, optionally increasing the number of docking strands associated with each target-specific binding partner, or
  - (b) a primer strand, optionally associating more than one docking strand with the primer strand,
- (4) contacting the sample with labeled imager strands capable of binding a docking strand, directly or indirectly,
- (5) optionally removing unbound labeled imager strands,
- (6) imaging the sample to detect bound labeled imager strands, and
- (7) optionally extinguishing signal from the bound labeled imager strand;
- (8) optionally repeating steps (1)-(7) or any subset thereof.

In some embodiment, a composition comprises: a sample bound to more than one target-specific binding partners, each binding partner bound to a nucleic acid strand and at least one docking strand stably bound to a labeled imager strand, directly or indirectly, wherein the nucleic acid strand is a docking strand or a primer strand if the nucleic acid is
- (a) a docking strand, increasing the number of docking strands associated with each target-specific binding partner, or
- (b) a primer strand, associating more than one docking strand with the primer strand.

In some embodiments, a composition comprises
- (1) a label,
- (2) a first nucleic acid domain, a second nucleic acid domain, and a third nucleic acid domain, wherein each nucleic acid domain is from 1 to 9 nucleotides long,
- (3) a first linking moiety linking the first nucleic acid domain and the second nucleic acid domain and
- (4) a second linking moiety linking the second nucleic acid domain and the third nucleic acid domain, wherein both linking moieties are independently chosen from (a) an abasic site with an intact phosphodiester backbone, (b) a linker cleavable by a nucleic acid glycosylase, (c) non-natural nucleotides, or (d) restriction site or a nicking site.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate one (several) embodiment(s) and together with the description, explain the principles described herein.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A shows Attachment of the Docking Strand to the target-recognizing moiety without signal amplification.

FIG. 1B shows attachment of the Docking Strand to the target-recognizing moiety with signal amplification using a branched structure, which can be created using processes such as HCR. FIG. 1C shows attachment of the Docking Strand to the target-recognizing moiety with signal amplification using a linear structure, which can be created using processes such as RCA. FIG. 1D shows modified hybridization chain reaction (HCR), where a docking site (domain b) is attached to one of the two hairpins of HCR, allowing introduction of multiple docking sites to one target-recognizing moiety. FIG. 1E shows rolling circle amplification to introduce multiple docking site (domain c-d) to one target-recognizing moiety. The following reference numbers are used in this figure. 101: Target. 102: Target-recognizing moiety. 103: Docking Strand. 120: Primer strand of the HCR reaction that is attached to the target-recognizing moiety. 121: one hairpin of HCR, which is attached with the docking site. 122: another hairpin of HCR. 123-126: Sequential hairpin assembly reactions. 127: Primer that is attached to the target-recognizing moiety. 128: linear template that can be circularized by ligation. 129: The ligation reaction. 130: Primer extension with DNA polymerase with strand-displacement activity. 131: multiple docking sites.

FIGS. 5A-D show removal of Imager Strand using nucleic acid-degrading enzymes. FIG. 5A shows a general scheme. FIG. 5B shows embodiments where there is a single deoxyuridine (dU) nucleotide in the Docking Strand-recognizing portion of the Imager Strand. FIG. 5C shows embodiments where there are multiple dU nucleotides in the Docking Strand-recognizing portion of the Imager Strand. FIG. 5D shows embodiments where the dU nucleotide is placed within the linkage between the Docking Strand-recognizing portion and the signal-generating moiety of the Imager Strand. 104: imager strand. 105: signal generating moiety of the imager strand. 106: linkage between the target-recognizing moiety and the docking strand. 107: optional linkage to additional docking strands. 120: primer strand of the hybridization chain reaction (HCR) that is attached. 201: dU as an example of a moiety that can be degraded enzymatically. 202: The enzymatic reaction to degrade dU. 203: The process where the remnant of the degradation reaction spontaneous dissociates from the Docking Strand.

FIG. 6A shows a self-priming hairpin is placed at the 3' end of the Imager Strand; the Imager Strand is removed using a polymerase with strand-displacement activity (e.g., phi29). FIG. 6B shows a self-priming hairpin is placed at the 3' end of the Imager Strand which is linked to the signal-generating moiety via nucleic acid hybridization; the Imager Strand is removed using a polymerase with strand-displacement activity. FIG. 6C shows a self-priming hairpin is placed at the 3' end of the Docking Strand; the Imager Strand is removed using a polymerase with strand-displacement activity. FIG. 6D shows a self-priming hairpin is placed at the 3' end of the Imager Strand; the Imager Strand is removed using a polymerase with 5'-to-3' exonuclease activity (e.g., DNA Polymerase I).

FIG. 6E shows a self-priming hairpin is placed at the 3' end of the Docking Strand; the Imager Strand is removed using a polymerase with 5'-to-3' exonuclease activity. FIG. 6F shows the self-priming hairpin is replaced by a hybridized duplex with an extendable 3' end. 301: Self-priming hairpin. 302: The reaction where the self-priming hairpin or the hybridized duplex with an extendable 3' end is extended by the DNA polymerase with strand-displacement activity. 303: The short oligonucleotide that brings the signal-generating moiety to the Imager Strand via hybridization. 304: The reaction where the self-priming hairpin or the hybridized duplex with an extendable 3' end is extended by the DNA polymerase with 5'-to-3' exonuclease activity. 305: hybridized duplex with an extendable 3' end. 306: Linkage between the target-recognizing moiety and the Docking Strand, wherein the linkage comprises covalent or non-covalent interactions.

FIG. 7A provides a schematic illustrating the process of switching between fluorescence imaging and brightfield imaging with DNA exchange and HRP-based amplification. FIG. 7B provides the resulting fluorescence image of tonsil tissue cytokeratin labeled with antibody-DNA conjugate and corresponding fluorescently labeled imager strand. FIG. 7C provides resulting brightfield immunohistochemistry image of cytokeratin in the same tonsil tissue following DNA exchange and HRP-based chromogenic amplification. FIGS. 7D and E show fluorescence signal obtained from cell samples stained for vimentin and DAPI without amplification (D, left) and with rolling circle amplification (E, right). FIG. 7F provides resulting fluorescence image of tonsil tissue cytokeratin labeled with antibody-DNA conjugate and corresponding fluorescently labeled imager strand (F, left). FIG. 7G, right, shows fluorescence image from the same tissue section after HCR amplification of the docking strands, and hybridization of the corresponding fluorescently labeled imager strand. In FIGS. 7D and 7E, the images show a DAPI nuclear stain in blue and appears as a generally round or bean-shaped object typically located in the center region of a cell. DAPI stains the DNA inside the nucleus of the cell, and was included in the images as proof that there are cells present in the field of view. The vimentin staining (red) in FIG. 7D is lower without amplification and in FIG. 7E brighter and more intense with amplification. The red vimentin staining shows filament-like or wispy staining mainly outside of the cell nucleus.

FIGS. 10A-B shows schematics and results for proximity detection with stable binding. Like FIGS. 7D-7E, FIGS. 10A-B show DAPI (blue) staining of the nucleus inside of cells. FIG. 10A also shows alpha-tubulin staining (green) primarily outside of the nucleus of the cell.

FIG. 13A shows DNA-Exchange imaging with the use of an intermediate strand (401) to link an imager strand and a docking strand bound to a target through a target-recognition moiety. FIG. 13B illustrates a primer strand (404) used to amplify the number of docking strands associated with a target-binding complex, where the resulting amplified product (403) is attached to multiple docking sites (103) and can be imaged with an imager strand, directly or indirectly through an intermediate strand as shown. FIG. 13C shows amplification of the number of docking strands associated with a target using a primer strand to initiate a hybridization chain reaction and imaging with the addition of an imager strand, bound to docking strand through an intermediate strand. FIG. 13D shows amplification of the number of docking strands associated with a target using a primer strand as a template for ligation and rolling circle amplification, followed by the addition of an imager strand, bound to docking strands through intermediate strands for imaging.

FIGS. 14A-D show removal efficiency of imager strands using nucleic acid-degrading enzymes varies with sequence design. Imager strands were synthesized with (FIGS. 14B and 14D) and without (FIGS. 14A and 14C) an abasic site. Fluorescence images of CD3 in tonsil tissues labeled with antibody-DNA conjugates are shown before (FIGS. 14A-B, shown at a 30,000-intensity scale) and after (FIGS. 14C-D, shown at a 2,000-intensity scale) removal of the corresponding fluorescently labeled imager strands.

FIGS. 15A-15F shows a combination of spectral and sequential multiplexing.

Figure 1A:
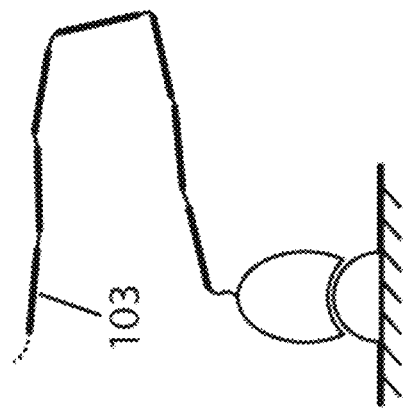
FIGS. 1A-E show a scheme of attaching Docking Strands to the target via a target-recognizing moiety. Specifically.

The following reference numbers are used throughout the figures and the application:

TABLE 1

| | Figure Reference Numbers |
|---|---|
| 101 | target |
| 102 | target-recognizing moiety |
| 103 | docking strand |
| 104 | imager strand |
| 105 | signal generating moiety of the imager strand |
| 106 | linkage between the target-recognizing moiety and the docking strand |
| 107 | optional linkage to additional docking strands |
| 120 | primer strand of the hybridization chain reaction (HCR) that is attached to the target-recognizing moiety |
| 121 | one hairpin of HCR, which is attached with the docking site |
| 122 | another hairpin of HCR |
| 123-126 | sequential hairpin assembly reactions |
| 127 | primer that is attached to the target-recognizing moiety |
| 128 | linear template that can be circularized by ligation |
| 129 | the ligation reaction |
| 130 | primer extension with DNA polymerase with strand-displacement activity |
| 131 | multiple docking sites |
| 201 | dU as an example of a moiety that can be degraded enzymatically |

TABLE 1-continued

| | Figure Reference Numbers |
|---|---|
| 202 | the enzymatic reaction to degrade dU |
| 203 | the process where the remnant of the degradation reaction spontaneous dissociates from the docking strand |
| 301 | self-priming hairpin |
| 302 | the reaction where the self-priming hairpin or the hybridized duplex with an extendable 3' end is extended by the DNA polymerase with strand-displacement activity |
| 303 | the short oligonucleotide that brings the signal-generating moiety to the Imager Strand via hybridization |
| 304 | the reaction where the self-priming hairpin or the hybridized duplex with an extendable 3' end is extended by the DNA polymerase with 5'-to-3' exonuclease activity |
| 305 | hybridized duplex with an extendable 3' end |
| 306 | linkage between the target-recognizing moiety and the docking strand, wherein the linkage comprises covalent or non-covalent interactions |
| 401 | intermediate strand |
| 402 | amplification reaction |
| 403 | amplification product and associated docking strands |
| 404 | primer |

DESCRIPTION OF THE EMBODIMENTS

I. Methods of Testing a Sample for the Presence of One or More Targets

This application relates to improved methods and compositions for testing for the presence of one or more targets with one or more target specific binding partners.

Exchange Imaging is a method to achieve high multiplexing capability so that many targets can be imaged on the same sample. The central concept of Exchange Imaging involves the following steps: (1) attaching different decodable information-carrying molecules (called docking strands) to different target-specific binding partners (such as but not limited to an antibody that recognizes a target), wherein target-specific binding partners of different specificity (i.e., binding different targets) are linked to different docking strands and optionally removing unbound target-specific binding partners (2) using a set of molecules (called imager strands), each specifically recognizing a docking strand and carrying an observable moiety, to label a subset of docking strands, and imaging the corresponding subset of targets, (3) extinguishing the signal from the bound labeled imager strand by removing the set of imager strands used in step 2, removing the observable moiety from the imager strand, or inactivating the observable moieties on such imager strands, and (4) using another set of imager strands, each specifically recognizing a docking strand and carrying an observable moiety, to label another subset of docking strands, and imaging the corresponding subset of targets, (5) optionally, steps 3 and 4 can be repeated to visualize multiple subsets of targets. End users will readily appreciate that not all steps should be repeated in all experiments. For example, in the last round of imaging, there would be no need to extinguish the signal from the bound labeled imager strand because no further imaging strands would be applied.

One non-limiting example of Exchange Imaging is DNA Exchange Immunofluorescence, where one uses antibodies as the target-recognizing molecules to image target proteins or other biomolecules, uses DNA oligonucleotides as docking strands, and uses DNA oligonucleotides that are complementary to the docking strands and labeled with at least one observable moiety (such as a fluorophore) as the imager strands. In step 3, extinguishing the signal from the bound labeled imager strand includes several embodiments. In some embodiments, one may remove the imager strand, remove the label from the imager strand, and/or the inactivate the label attached to the imager strand. These various methods may be employed by using high temperature, low ionic strength buffers, denaturant (including formamide, for example), DNA helicase, DNase, strand displacement, chemical cleavage, enzymatic cleavage, chemical bleaching, photo-bleaching, and/or photochemical bleaching. By bound labeled imager strand, we aim to distinguish the labeled imager strand that has, at one point, bound to the docking strand from the excess labeled imager strand that did not bind to a docking strand. During the process of extinguishing the signal, the so-called bound labeled imager strand may remain bound to the docking strand or it may not remain bound to the docking strand.

In some embodiments, imaging the sample to detect bound labeled imager strands detects the presence of bound labeled imager strands. In some embodiments, imaging the sample to detect bound labeled imager strands detects the presence, location, and/or number of bound labeled imager strands.

Various types of imaging may be used in conjunction with the methods. For example, the imaging may include any type of microscopy that has an objective, illumination, and a sensor. In some embodiments, imaging is performed using a light microscope, fluorescence microscope including widefield, confocal (line and point scanning, spinning disk), total internal reflection (TIR), stimulated emission depletion (STED), light-sheet illumination (including lattice light-sheet illumination), structured illumination (SIM), expansion microscopy, and electron microscopy.

A. Amplification Methods

In microscopy, signal amplification is desired in many situations such as when the abundance of target is low, when the allowable exposure time is short, and/or when the sensitivity of the imaging equipment is low. Signal amplification offers advantages in DNA exchange immunofluorescence. In traditional, single-plex immunofluorescence (where only one target is analyzed), one often uses unconjugated primary antibody and fluorescent-labeled secondary antibody. Because the secondary antibodies are often polyclonal, multiple molecules of secondary antibody can bind to one molecule of primary antibody, resulting in amplification of signal. In DNA Exchange Immunofluorescence, however, in some embodiments, users directly label the DNA docking strand to the primary antibody, thus eliminating such signal-amplification step obtained by using a polyclonal secondary antibody. As a result, in some cases, DNA exchange immunofluorescence may have lower signal intensity relative to traditional immunofluorescence.

Thus, in one embodiment, amplification is used to improve the signal intensity in multiplexed DNA exchange immunofluorescence. Many methods for signal amplification in microscopy exist, but not all can be applied to DNA exchange immunofluorescence. One of the most well-known methods involves linking (covalently or non-covalently) the target-recognizing molecule (e.g., antibody) to an enzyme that can convert a non-observable substrate into an observable product. Many enzymes such as horseradish peroxidase (HRP), alkaline phosphatase (AP), glucose oxidase (GO), β-galactosidase (β-gal) have been used for these purposes. And an array of chromogenic, fluorogenic and chemiluminescent substrates for these enzymes have been developed, such as 3,3'-diaminobenzidine (DAB), nitro blue tetrazolium chloride (NBT), 5-bromo-4-chloro-3-indolyl phosphate (BCIP), and 5-bromo-4-chloro-3-indoyl-β-D-galactopyranoside (X-Gal). Another strategy to exploit such enzymes in signal amplification is to create covalent bonds between the target (or other molecules in vicinity to the target) and an observable reporter molecule. This strategy is exemplified by tyramide signal amplification (TSA) technology that is commercialized by Thermo Fisher and Perkin Elmer, among others. However, none of these signal-amplification methods is compatible with exchange imaging, as the observable reporter, enzyme/primer or the substrate is brought to the vicinity of the target permanently or without a decodable docking strand. DNA-based (i.e., decodable) signal amplification methods where the observable signal can, at least in principle, be removed have been reported (e.g., Zimak, et al., Chembiochem 13(18):2722-8 (2012) (PMID: 23165916)). However, such methods involve multiple rounds of manipulation and the signal gain is modest.

Another type of signal amplification involves linking (covalently or non-covalently) the target-recognizing molecule to a primer molecule of a polymerization or dendrimerization reaction. On example of such polymerization reactions is rolling circle amplification (RCA) where the primer of the RCA is linked to the target-recognizing molecule and is converted to a long repetitive single-stranded DNA. Fluorescent molecules can be either directly incorporated into the RCA product via fluorescent-labeled nucleotides, or be bound to the RCA product as a part of a fluorescent-labeled oligonucleotide that is designed to hybridize to the RCA product. Other examples of such polymerization or dendrimerization reactions include branched DNA toehold-based strand displacement (Schweller et al. PMCID: PMC3517005), hybridization chain reaction (HCR) (Dirks et al., 2014, PMID: 15492210, 24712299) and a similar DNA hairpin-based dendrimerization reaction (Yin et al., 2008, PMID 18202654), which here we call HDR. Common applications of amplification methods such as RCA, HCR, and HDR do not include the option for Exchange Imaging, but could be compatible as demonstrated by the improvements described herein.

Herein we discuss embodiments covering signal amplification that is compatible with exchange imaging. We describe a series of embodiments that make signal amplification compatible with exchange imaging. These embodiments can be divided into two classes based on whether the amplification product is decodable. For example, if the amplification product contains a docking strand component (e.g. single-stranded DNA), many (e.g., >5) antibodies against different targets can be programmed to generate such product of distinct docking strand sequences that can later be decoded by the ssDNA molecules of complementary sequence. Thus, such amplification product is considered decodable. In such cases, signal amplification for different targets can be carried out simultaneously, followed by simultaneous and/or sequential imaging of different amplification products. Simultaneous amplification carried out for different targets can be considered multiplexed amplification.

In contrast, when the amplification product is a fluorophore or label that is covalently attached or noncovalently deposited near the target but does not contain a docking strand that could interact with an imager strand, these amplification products are considered undecodable. For example, when the enzyme responsible for signal amplification is HRP, the product is a chemical chromophore that does not allow many variations that can be specifically bound by many molecules serving as imager strands. In such cases, signal amplification for different targets may be carried out sequentially, and the enzyme linked to a target that has already been amplified may be removed from the sample. Simultaneous signal amplification of undecodable amplification products is possible if orthogonal enzyme-substrate pairs can be used.

Therefore, in some embodiments a method comprises (1) contacting a sample being tested for the presence of one or more targets with one or more target-specific binding partners, wherein each target-specific binding partner is linked to a nucleic acid strand, and wherein target-specific binding partners of different specificity are linked to different nucleic acid strands, (2) optionally removing unbound target-specific binding partners, (3) wherein the nucleic acid strand is a docking strand or a primer strand and if the nucleic acid is (a) a docking strand, increasing the number of docking strands associated with each target-specific binding partner or (b) a primer strand, associating more than one docking strand with the primer strand (in either (a) or (b), such as, for example, amplifying the number of docking strands available), (4) contacting the sample with labeled imager strands capable of binding a docking strand, directly or indirectly, (5) optionally removing unbound labeled imager strands, (6) imaging the sample to detect bound labeled imager strands, (7) optionally removing the bound labeled imager strands from the docking strands, and (8) optionally repeating steps (1)-(6), or any subset thereof.

By docking strands associated each target specific binding partner, here and throughout the application, Applicant does not intend to require amplification to occur on every single docking strand, but that amplification generally occurs on the docking strands associated with the various target-specific binding partners, as desired by the user (including amplifying only some docking strands participating in detecting targets A and B, while not amplifying docking strands participating in detecting target B.) Amplification may also be incomplete, such as amplification occurring on only some but not all of the copies of the docking strand participating in detecting a given target. Additionally, amplification may replicate the entire docking strand or it may replicate only a portion of the docking strand sufficient for binding an imager strand.

Additionally, in some embodiments, a method comprises (1) contacting a sample being tested for the presence of one or more targets with one or more target-specific binding partners, wherein each target-specific binding partner is linked to a nucleic acid strand and wherein target-specific binding partners of different specificity are linked to different nucleic acid strands, (2) optionally removing unbound target-specific binding partners, (3) contacting the sample with labeled imager strands capable of binding a docking strand, directly or indirectly, wherein the nucleic acid strand in (1) is either a primer strand or a docking strand and if the nucleic acid strand is a primer strand, it is linked to a docking strand (4) optionally removing unbound labeled imager strands, (5) imaging the sample to detect bound labeled imager strands and determine if amplification (step (7)) is required, (6) optionally removing the bound labeled imager strands from the docking strands, (7) optionally increasing the number of docking strands associated with each target-specific binding partner (such as, for example, amplifying the number of docking strands available by multiple means, including, but not limited to self-assembly of docking strand complexes, other assembly methods, branched and circular docking strands, etc.), and (8) optionally repeating steps (1)-(7), or any subset thereof.

1. Amplification

Decodable Amplification Products.

Figure 1B:
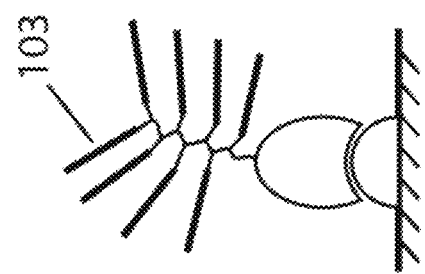
Figure 1C:
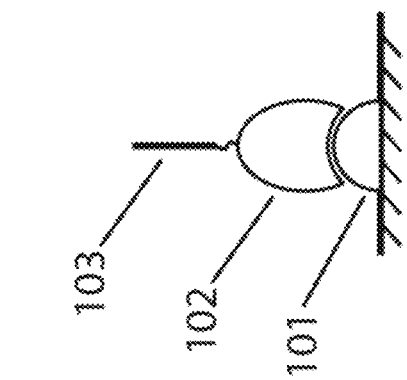

Decodable amplification products include those cases in which the amplified product is a docking strand. In one embodiment, the docking strand does not contain an observable label. In one embodiment, the docking strand serves as a barcode for an observable label (or imager strand). It should be noted at the outset that the docking strands, or docking sites, may be introduced to the target during a signal-amplification reaction (FIG. 1b-c), so that multiple docking strands are attached to one target molecule. Without being limiting, there are at least two strategies of achieving this: (Strategy 1) creating multiple docking sites that are attached to a scaffold, which is in turn attached to the target-recognizing moiety (FIG. 1b), and (Strategy 2) creating multiple binding sites on one piece of long single-stranded DNA that is attached to the target-recognizing moiety (FIG. 1c).

One may use RCA, HCR or HDR to generate a polymeric or dendrimeric product from the primer molecule linked to the antibody. In some embodiments, the product may contain many (e.g., greater than 2, 5, 10, 15, 20, 25, 50, 100, etc.) copies of single-stranded DNA domains that can serve as the docking strand and thus be recognized by oligonucleotides serving as the imager strand. Such DNA domains may be long enough (e.g. 7, 8, 9, 10, 11, 12, 13, 14, 15, 20, or more nucleotides long, or be able to bind its complementary strand with Kd<1 nM at imaging condition). For RCA, this is achieved regularly. For HCR and HDR, if necessary one can include, at the loop or tail of the substrate hairpin, DNA domains that do not participate in the strand-displacement cascades but constitute part or the entirety of the imager strand-binding site.

Figure 1D:
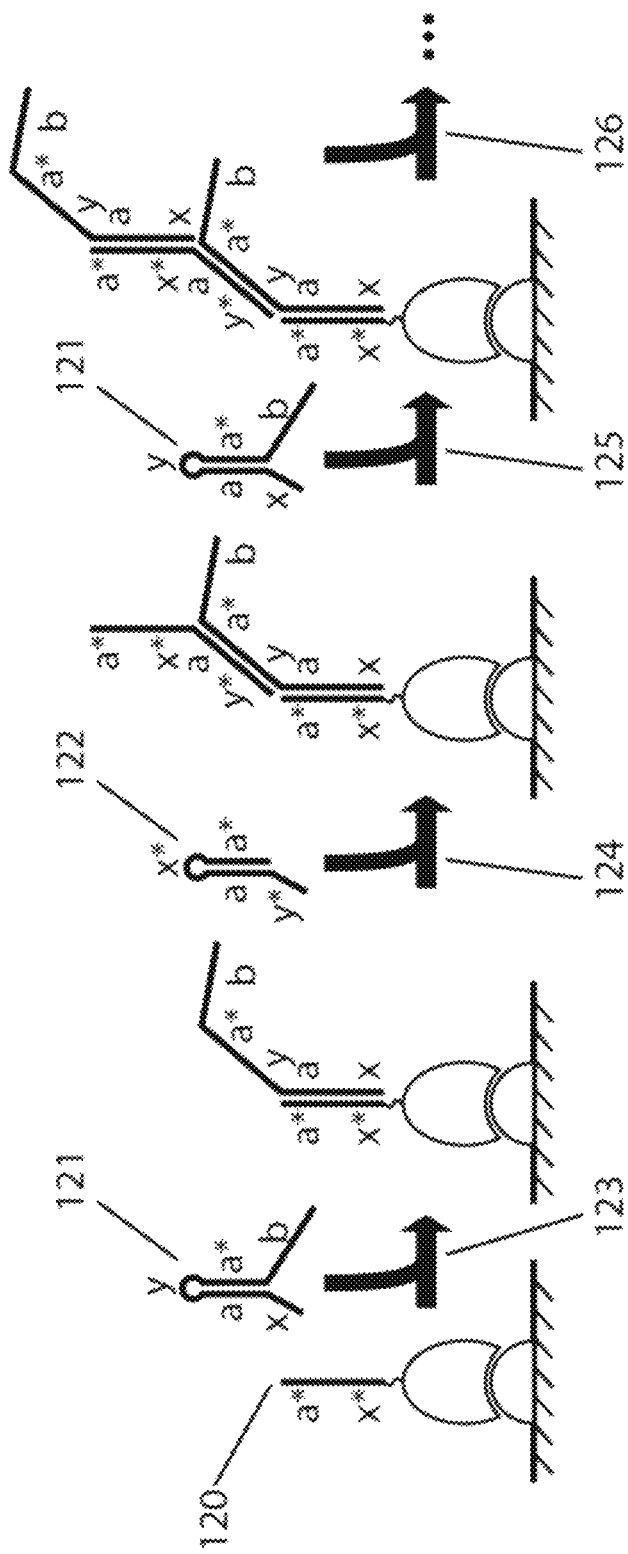

In one embodiment, a modified version of hybridization chain reaction (HCR) is employed for signal amplification, in which two hairpins (105 and 106 of FIG. 1d) are assembled onto the primer strand (104 of FIG. 1d) in an alternating fashion. Either or both of the two hairpins can carry a docking site (domain b on hairpin 105 of FIG. 1d). Tens to hundreds of hairpin units can be assembled onto one primer strand, brining tens to hundreds of docking sites to the target-recognizing moiety. Several pairs of hairpin sequences (without the docking site) have been demonstrated by the Pierce group to enable successful HCR reactions. Hairpin sequences with the docking sites can be designed with the same principle, although care may be taken to ensure that the docking site does not form unwanted secondary structure with the rest of the hairpin.

Figure 1E:
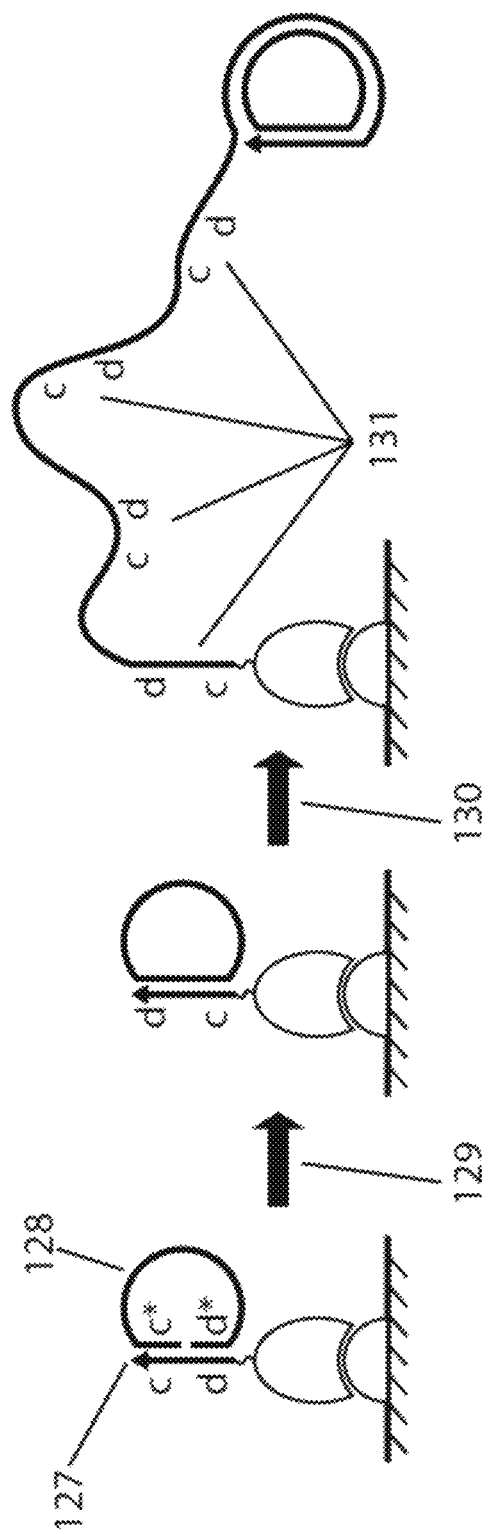

In another embodiment, signal amplification involves linking (covalently or non-covalently) the target-recognizing molecule to a primer molecule of a polymerization or dendrimerization reaction. On example of such polymerization reactions is rolling circle amplification (RCA, FIG. 1e) where the primer of the RCA is linked to the target-recognizing molecule and is converted to a long repetitive single-stranded DNA. Fluorescent molecules can be either directly incorporated into the RCA product via fluorescent-labeled nucleotides, or be bound to the RCA product as a part of a fluorescent-labeled oligonucleotide that is designed to hybridize to the RCA product.

There are many ways to carry out RCA, one of which is to first ensure that the oligonucleotide conjugated to the target-recognizing moiety (here we call 'primer', 111 of FIG. 1e) has an extendable 3' end. Then one can introduce a linear template strand (112 of FIG. 1e) that can hybridize to the primer in the circular fashion, in which the primer brings the two ends of the template together so that the two ends can be ligated. Next, a ligase (such as T4 DNA ligase or CircLigase™ ssLigase, for example) is used to ligate the two ends to form a circle. After the ligation the primer is hybridized to the circular template. Next, a DNA polymerase with strand-displacement activity (e.g., phi29, Bst, Vent (exo⁻)) can extend the primer along the circular template multiple rounds to create a concatemeric repeat. Part of the entirety of the repeat unit (domains c-d, or 115 of FIG. 1e) can serve as the docking sites (or docking strands) for imager strands.

An alternative method of RCA involves the use of a nonlinear amplifier or template strand, wherein an oligonucleotide (such as a docking strand) conjugated to the target-recognizing moiety is hybridized to a circular DNA template (amplifier strand), followed by extension of the docking strand by a DNA polymerase to create a concatemeric repeat of the reverse complement of the amplifier strand (i.e. an amplified strand or RCA product). The hybridization of the amplifier strand to the oligonucleotide conjugated target-recognizing moiety may occur before (preassembly or prehybridization) or after the oligonucleotide conjugated target-recognizing moiety contacts the sample.

Thus, in some embodiments, at least one oligonucleotide-conjugated target-recognizing moiety is hybridized to a nonlinear amplifier strand before being introduced to the sample. When the user chooses to pre-assemble an antibody-DNA conjugate with an amplifier, a method to test a sample for the presence of one or more targets comprises (1) contacting a sample being tested for the presence of one or more targets with one or more target-specific binding partners, wherein each target-specific binding partner is linked to a nucleic acid strand and wherein target-specific binding partners of different specificity are linked to different nucleic acid strands, and wherein at least one nucleic acid strand is hybridized to a nonlinear amplifier strand (2) optionally removing unbound target-specific binding partners, (3) amplifying the docking strand with rolling circle amplification (i.e., increasing the number of docking strands or introducing a plurality of docking strands) to produce a rolling circle amplification product (4) contacting the sample with labeled imager strands having complementarity to the docking strand or the rolling circle amplification product, (5) imaging the sample to detect bound labeled imager strands, (6) optionally removing the bound labeled imager strands, and (7) optionally repeating steps (1)-(7), or any subset thereof. In this process, the rolling circle amplification product comprises a concatemeric repeat of the reverse complement of the amplifier strand.

In another embodiment, imager strands may be hybridized to the RCA product (e.g. the concatemeric repeat of the reverse complement of the amplifier strand that is linked to the target-recognizing moiety) during the RCA reaction. In some embodiments, therefore, amplification occurs using rolling circle amplification, while in the presence of labeled imager strands having complementarity to the amplified strand. For example, a sample may be contacted with an oligonucleotide conjugated to a target-recognizing moiety that is either prehybridized to an amplifier strand or the amplifier strand may be hybridized in a later step. Then, all additional components for the RCA reaction may be added in one step including proteins (e.g. DNA polymerases, optionally BSA), nucleotides, buffer solution, salts, and imager strands. In some embodiments, a user may wish to prevent the imager strand from being amplified. This can be accomplished by several means, including, but not limited to employing a 3'-modified imager strand having a modification on the 3' end. For example, the 3' modification on the imager strand may include a label (such as a fluorophore), a modified base, a stop code or terminator, a 3'-O-modification, a dideoxy-C, a dideoxy-G, a dideoxy-A, a dideoxy-T, an inverted nucleotide, any modification that eliminates the presence of a 3' hydroxyl group, or a single-stranded extension of the 3' end that is not complimentary to the amplifier strand.

In addition to HCR and RCA, other examples of such polymerization or dendrimerization reactions include DNA hairpin-based dendrimerization reaction (HDR) (Yin et al., 2008, PMID 18202654), and toe-hold mediated strand displacement.

DNA strand displacement is a method for the isothermal and dynamic exchange of DNA complexes. Strand displacement can be designed and intentionally controlled based on an understanding of DNA hybridization interactions and thermodynamics, and can be facilitated by introducing engineered handles which are known as "toehold domains." The ability to modulate binding interactions and exchange hybridization partners gives rise to a series of potential signal amplification applications.

In another embodiment, an encodable tyramide-based signal amplification product is described. This method comprises (1) contacting a sample being tested for the presence of one or more targets with one or more target-specific binding partners, wherein each target-specific binding partner is linked to a nucleic acid strand and wherein target-specific binding partners of different specificity are linked to different nucleic acid strands, (2) optionally removing unbound target-specific binding partners, (3) contacting the sample with enzyme-labeled strands capable of binding a docking strand, wherein the nucleic acid strand in (1) is either a primer strand or a docking strand and if the nucleic acid strand is a primer strand, it is linked to a docking strand (5) optionally removing unbound enzyme-labeled strands, (4) contacting the sample with tyramide-bound docking strands, (5) enzymatically converting the tyramide moiety into an activated state, wherein the activated state results in a covalent linkage of the tyramide-bound docking strand to the enzyme-labeled target site, (6) optionally quenching the enzymatic reaction, (7) removing the enzyme-labeled strands, and (8) optionally repeating a subset of steps 3-8. In one embodiment, the enzyme-linked strand is an HRP-linked strand.

In another embodiment, a method comprises (1) contacting a sample being tested for the presence of one or more targets with one target-specific binding partner, wherein the target-specific binding partner is linked to an enzyme (2) optionally removing unbound target-specific binding partners, (3) contacting the sample with tyramide-bound docking strands, (4) enzymatically converting the tyramide moiety into an activated state, wherein the activated state results in a covalent linkage of the tyramide-bound docking strand to the enzyme-labeled target site, (5) quenching the enzymatic reaction, and (6) optionally repeating a subset of steps 1-8, wherein target-specific binding partners of different specificity are introduced. In one embodiment, the enzyme-linked target-specific binding partners contain HRP.

Figure 2:
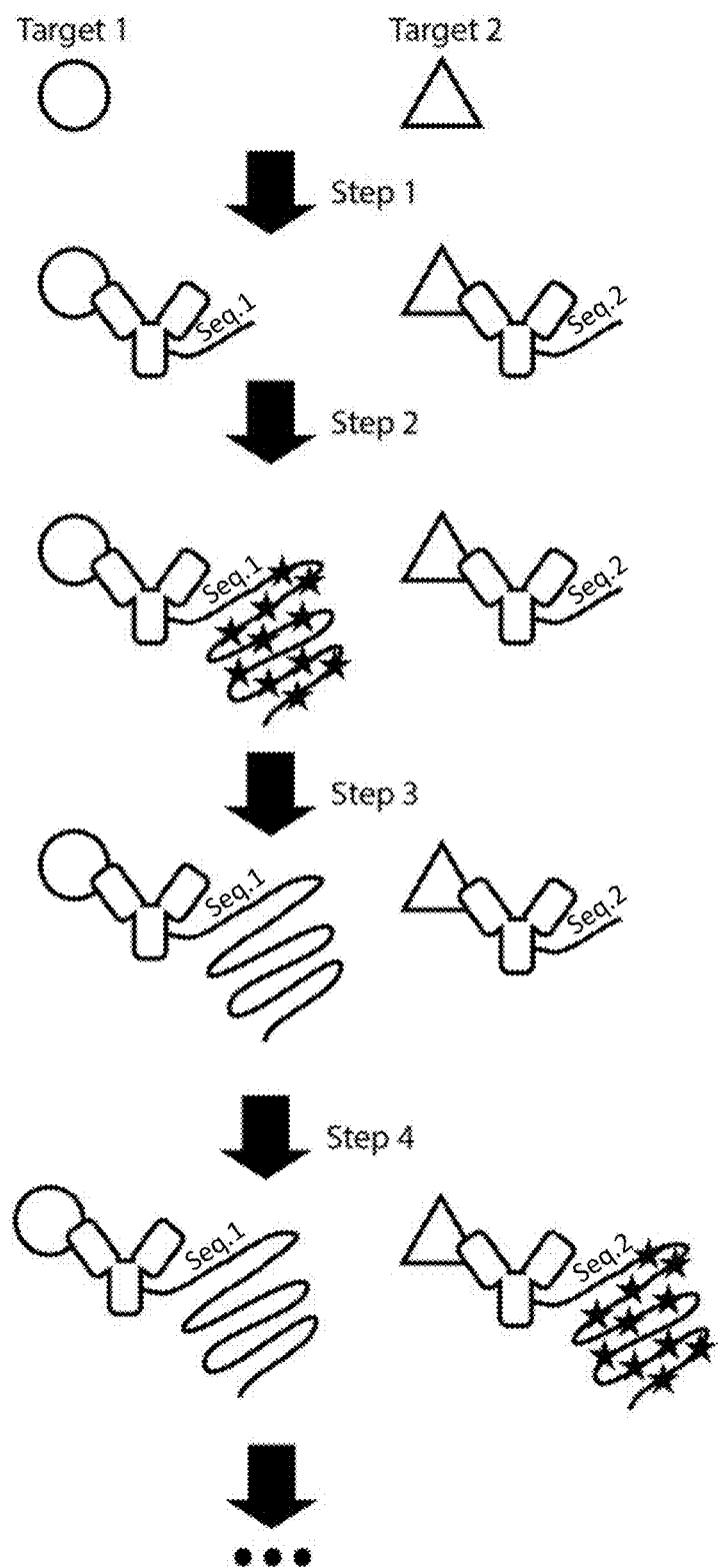
FIG. 2 shows sequential amplification, polymerization, and dendrimerization for amplified and removable signal.
Figure 3:
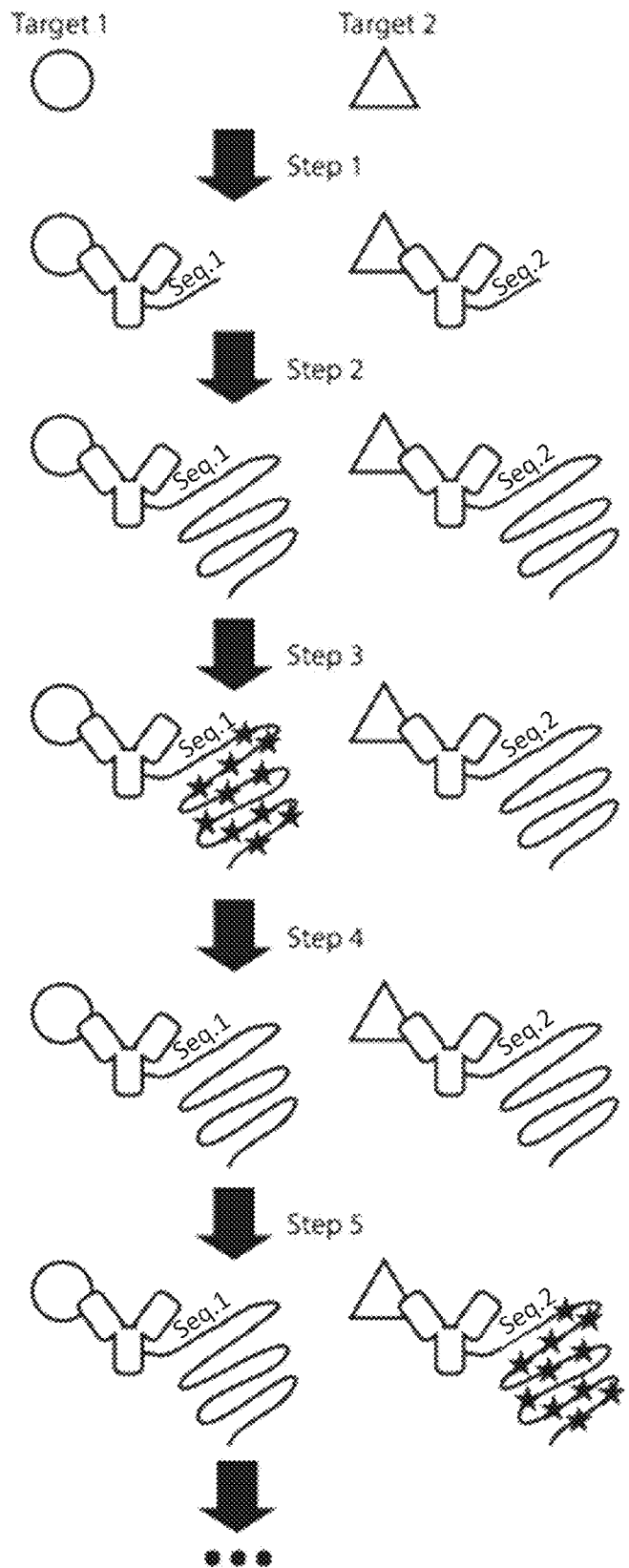
FIG. 3 shows simultaneous amplification, polymerization, and dendrimerization for amplified and removable signal.

As shown in FIG. 2, the amplification of multiple targets can be carried out sequentially. Alternatively, the amplification of multiple targets can be carried out simultaneously (FIG. 3). Imaging steps can be carried out between rounds of amplification, or following all rounds of amplification.

Undecodable Amplification Products.

Undecodable amplification products include those cases in which the amplified product is an observable label that does not have specific affinity for an imager strand. In one embodiment, the undecodable amplification product could be a fluorophore, chromogenic stain, or nanoparticle.

Figure 4A:
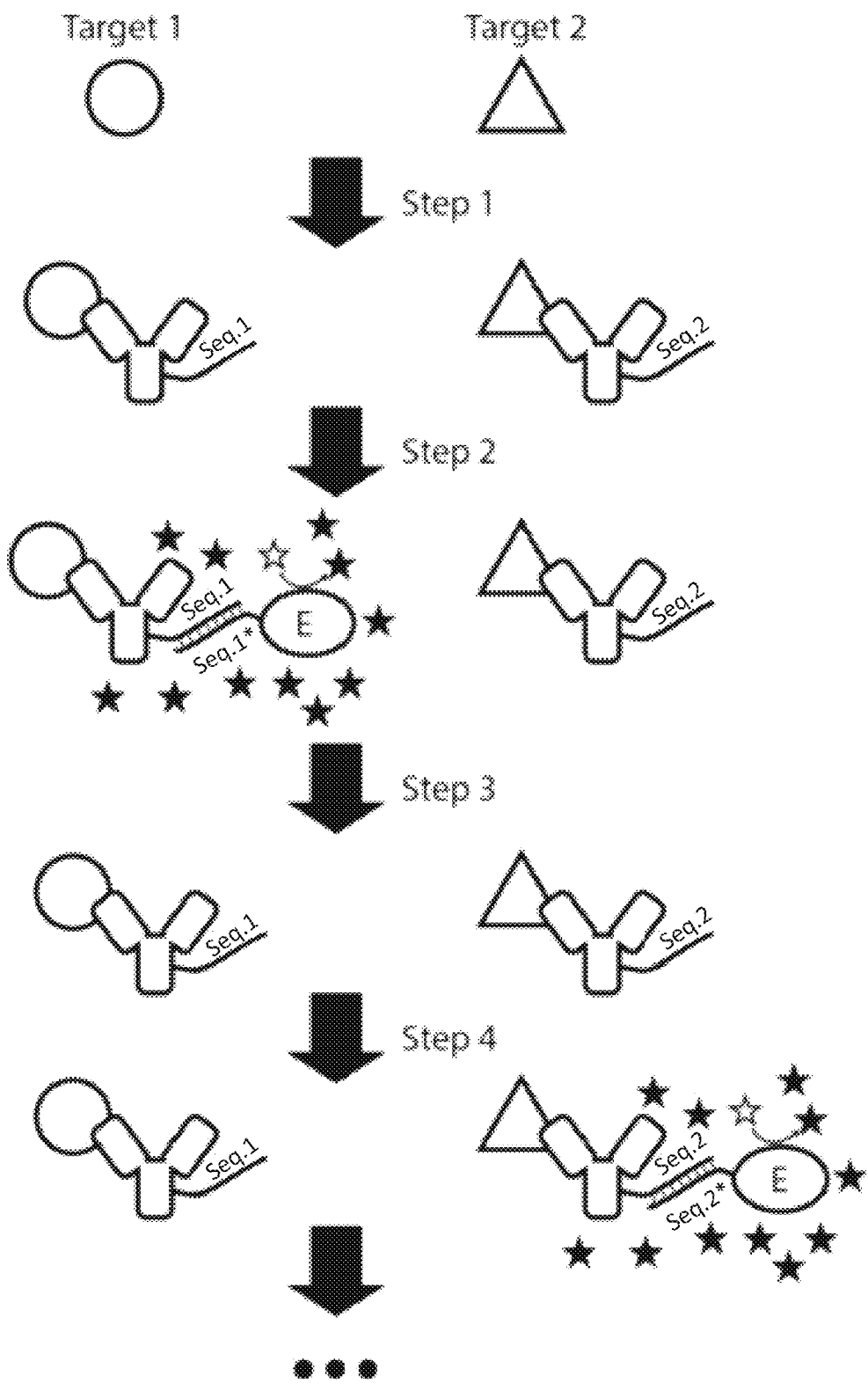
FIGS. 4A-B illustrate (A) sequential imaging with sequential amplification from HRP-like enzymes and (B) simultaneous imaging with sequential amplification from HRP-like enzymes.

In one embodiment, a method to produce undecodable amplification products comprises: (1) contacting a sample being tested for the presence of one or more targets with one or more target-specific binding partners, wherein each target-specific binding partner is linked to a nucleic acid strand and wherein target-specific binding partners of different specificity are linked to different nucleic acid strands, (2) optionally removing unbound target-specific binding partners, (3) contacting the sample with enzyme-labeled strands capable of binding a docking strand, wherein the nucleic acid strand in (1) is either a primer strand or a docking strand and if the nucleic acid strand is a primer strand, it is linked to a docking strand, (5) optionally removing unbound enzyme-labeled strands, (4) contacting the sample with a substrate for the enzyme, (5) allowing an enzymatic reaction to produce an amplification product, (6) quenching the enzymatic reaction, (7) imaging the sample to detect the presence or absence of one or more targets, (8) removing the amplification product, and (9) repeating a subset of steps 1-9. Examples of enzymes that could be used include HRP, AP, GO, β-gal. When the enzyme is linked to an imager strand, i.e. a strand capable of binding a docking strand), sequential amplification and imaging can be carried performed (FIG. 4). FIG. 4a illustrates a method for sequential amplification and sequential imaging. Here, a method is employed to remove or inactivate the amplification product between each imaging round. Removing or inactivating the amplification product can be done by carefully choosing the substrate. For example, one may use a chromogenic substrate of HRP that is soluble in sample-friendly organic solution (e.g., 3-amino-9-ethylcarbazole, which is alcohol-soluble, PMID 19365090). In this case, after staining of docking strand-conjugated antibodies (FIG. 4a, Step 1), introducing the imager strand-conjugated HRP for one target and the substrate (FIG. 4, Step 2), and imaging the sample, one can use alcohol (e.g., methanol) to remove the HRP product and remove the imager strand using any of the method described herein or their combination. Next one can introduce the imager strand-conjugated HRP for another target and repeat the process.

One may also use the TSA amplification method where the fluorophore can be readily bleached. For example, many cyanine fluorophores and Alexa fluorophore can be readily bleached by hydrogen peroxide in acidic or basic conditions (PMID: 26399630). Alternatively, one can synthesize a TSA dye that contains a cleavable bond between the tyramide and the fluorophore. In this case the fluorophore can be inactivated by cleaving this bond and washing.

Figure 4B:
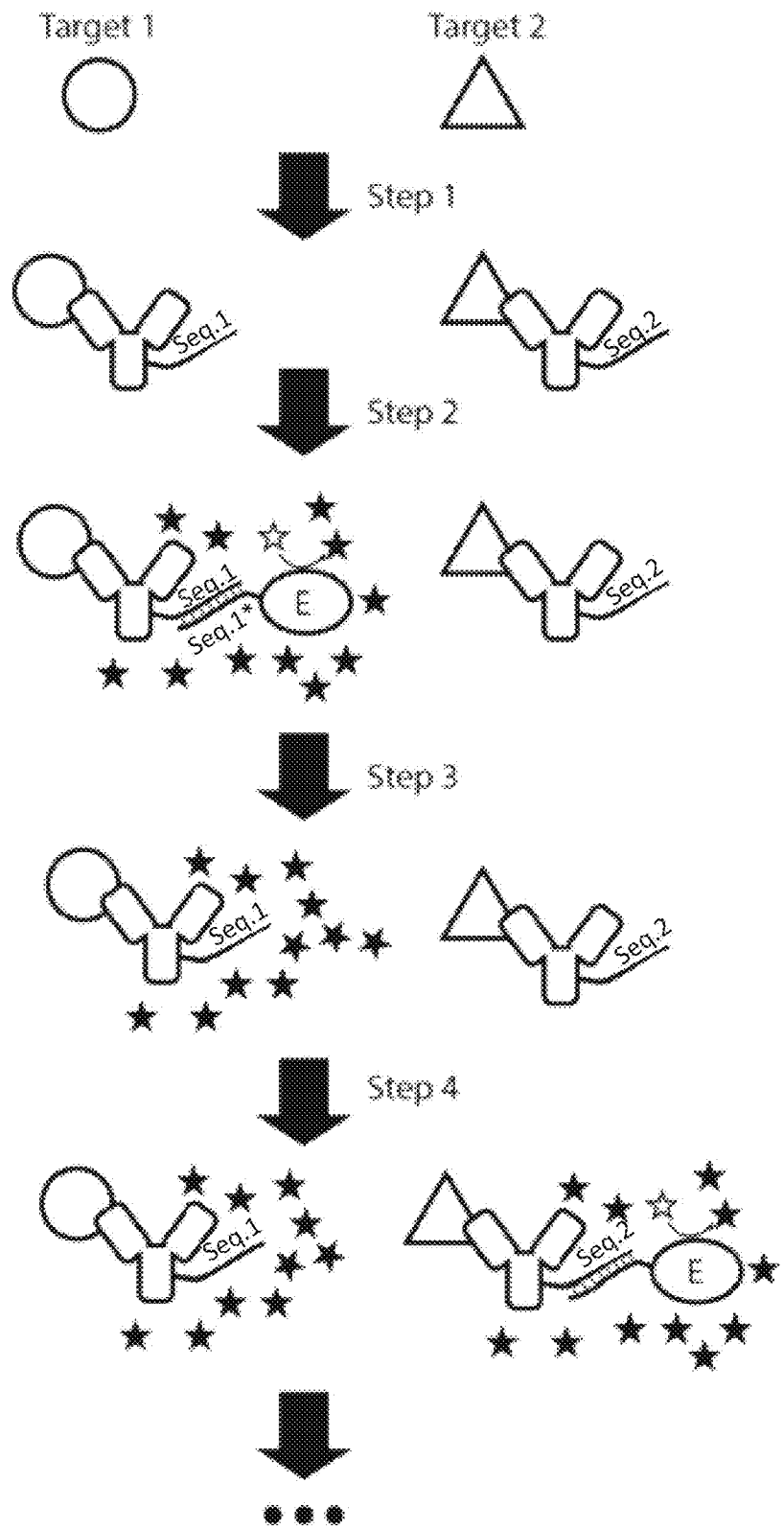

FIG. 4b illustrates a method for sequential amplification and simultaneous imaging. In this case, after staining of docking strand-conjugated antibodies (FIG. 4b, Step 1), introducing the imager strand-conjugated enzyme for one target and the substrate (FIG. 4, Step 2, using HRP and TSA for example) to generate amplified product, one can remove the imager strand-conjugated enzyme without removing the amplified product, and repeat multiple rounds of amplification for multiple targets prior to imaging the sample in a single imaging step.

One may also use RCA, HCR, and HDR to achieve signal amplification without decoding the amplification product. For example, after multiplexed antibody staining, one can add reagent (circular template in the case of RCA, and substrate hairpins in the case of HCR and HDR) that only supports the polymerization/dendrimerization of one subset of target and directly incorporation of fluorescent dyes in the amplification product (e.g., via fluorescent-labeled nucleotides in the case of RCA, and via fluorophore-labeled hairpin substrate in the case of HCR and HDR). After imaging of this subset of targets and inactivation of the dye by bleaching or cleavage as described above, one can introduce the reagent that supports the polymerization/dendrimerization of another subset of targets and directly incorporation of fluorescent dyes in the amplification product. This process can then be repeated.

Multiple types of signal amplification can even be used in combination. For example, Gusev et al reported combining rolling circle amplification and HRP-based signal amplification (PMID: 11438455).

One may replace the fluorophore (that is brought to the target via DNA complexes or other amplification method), by other molecule or moieties that can be directly or indirectly observed. These molecules or moieties include, but are not limited to, metal particles, plasmonic enhancers, and proteins.

2. Nonlinear Amplification

A nonlinear DNA template could be employed for signal amplification as a circular amplification strand. A circular oligo, with complementarity to a docking strand, can be generated separately from the amplification method. For example, ex situ ligation could be performed on a template DNA strand to form a circular strand of DNA. A circular strand could be hybridized to a docking strand that is attached to a target-specific binding partner before contacting the sample. Alternatively, the target-specific binding partner could first be used to stain the sample, and then subsequently the circular strand could be introduced to the sample to hybridize with the docking strand on the target-specific binding partner. Following the formation of a complex wherein a circular strand is attached to a docking strand that is linked to a target-specific binding partner, rolling circle amplification (RCA) could be carried out. This method offers certain advantages as it can be used to circumvent issues with inefficient in situ ligation steps.

In some situations, an amplifier strand may be employed. For example, in some embodiments, a method comprises (1) contacting a sample being tested for the presence of one or more targets with one or more target-specific binding partners, wherein each target-specific binding partner is linked to a nucleic acid strand and wherein target-specific binding partners of different specificity are linked to different nucleic acid strands, (2) optionally removing unbound target-specific binding partners, (3) contacting the sample with a nonlinear amplifier strand having complementarity to a nucleic acid strand, wherein the nucleic acid strand in (1) is either a primer strand or a docking strand (4) optionally removing unbound nonlinear amplifier strands, (5) amplifying the docking strand with rolling circle amplification (i.e., increasing the number of docking strands or introducing a plurality of docking strands), (6) contacting the sample with labeled imager strands capable of binding a docking strand, either directly or indirectly, (7) imaging the sample to detect bound labeled imager strands, (8) removing the bound labeled imager strands, and (9) optionally repeating steps (1)-(8), or any subset thereof.

In some embodiments, a polymerase may be used for RCA. In some instances, the labeled imager strands are linear strands. In some instances, the nonlinear amplifier strands are circular strands. In some instances, the nonlinear amplifier strands are branched strands. In some instances, the nonlinear amplifier strand becomes circular after ligation.

In some embodiments, amplification products may comprise a geometric shape, such as a triangle, quadrilateral, pentagon, hexagon, and the like.

B. Variations in Method Steps

There are various ways of approaching multiplexed imaging, including options for amplifying the signal using amplification steps at different time points and repeated steps to allow for imaging of multiple targets or reinterrogation of a single target. Methods may also optionally include extinguishing the signaling image at various points in time.

1. Amplifying Signal Before Applying Imager Strands and Optionally Extinguishing Signal from the Bound Labeled Imager Strand In some embodiments, a method to test a sample for the presence of one or more targets comprises (1) contacting the sample with one or more target-specific binding partners, wherein each target-specific binding partner is linked to a nucleic acid strand and wherein target-specific binding partners of different specificity are linked to different nucleic acid strands, (2) optionally removing unbound target-specific binding partners, (3) wherein the nucleic acid strand is a docking strand or a primer strand and if the nucleic acid is (a) a docking strand, increasing the number of docking strands associated with each target-specific binding partner or (b) a primer strand, associating more than one docking strand with the primer strand, (4) contacting the sample with labeled imager strands capable of binding a docking strand, either directly or indirectly, (5) optionally removing unbound labeled imager strands, (6) imaging the sample to detect bound labeled imager strands, and (7) optionally extinguishing signal from the bound labeled imager strand. In some instances, after step (4) and after optionally performing step (5) the method further comprises increasing the number of docking strands associated with each target-specific binding partner. In some embodiments, the method further comprises removing unbound labeled imager strand after the increasing the number of docking strands. Thus, in some modes, amplifying the docking strand with rolling circle amplification occurs separately from contacting the sample with labeled imager strands having complementarity to the amplified strand. By amplified strand, we mean the product of amplification (sometimes also called the amplification product or the RCA product if rolling circle amplification is employed).

In some instances, the sample is mounted to an optically transparent support. In some embodiments, the increase in the number of docking strands associated with each target-specific binding partner is achieved using an enzyme. For example, the enzyme approaches described in Section I.A above may be employed.

1. Amplifying Signal in the Presence of Imager Strands and Optionally Extinguishing Signal from the Bound Labeled Imager Strand In some embodiments, a method to test a sample for the presence of one or more targets comprises (1) contacting the sample with one or more target-specific binding partners, wherein each target-specific binding partner is linked to a nucleic acid strand and wherein target-specific binding partners of different specificity are linked to different nucleic acid strands, (2) optionally removing unbound target-specific binding partners, (3) contacting the sample with labeled imager strands capable of binding a docking strand, either directly or indirectly, (4) wherein the nucleic acid strand is a docking strand or a primer strand and if the nucleic acid is (a) a docking strand, increasing the number of docking strands associated with each target-specific binding partner or (b) a primer strand, associating more than one docking strand with the primer strand, wherein the amplification occurs in the presence of the imager strand (5) optionally removing unbound labeled imager strands, (6) imaging the sample to detect bound labeled imager strands, and (7) optionally extinguishing signal from the bound labeled imager strand. In some instances, after step (4) and after optionally performing step (5) the method further comprises increasing the number of docking strands associated with each target-specific binding partner. In some embodiments, the method further comprises removing unbound labeled imager strand after the increasing the number of docking strands.

In some instances, the sample is mounted to an optically transparent support. In some embodiments, the increase in the number of docking strands associated with each target-specific binding partner is achieved using an enzyme. For example, the enzyme approaches described in Section I.A above may be employed.

The imager strands may have complementarity to the docking strand. The imager strand may be a circular imager strand for rolling circle amplification. The imager strand may be an imager strand that circularizes in the presence of the docking strand and ligase. In some embodiments, the imager strand may comprise at least 2, 3, 4, 5, 6, 7, 8, 9, or 10 regions that are complementary to the docking strand.

2. A Method to Test a Sample Mounted to an Optically Transparent Support

In some embodiments, a method to test a sample mounted to an optically transparent support for the presence of one or more targets comprises (1) contacting the sample with one or more target-specific binding partners, wherein each target-specific binding partner is linked to a nucleic acid strand and wherein target-specific binding partners of different specificity are linked to different nucleic acid strands, (2) optionally removing unbound target-specific binding partners, (3) wherein the nucleic acid strand is a docking strand or a primer strand and optionally if the nucleic acid is (a) a docking strand, increasing the number of docking strands associated with each target-specific binding partner or (b) a primer strand, associating more than one docking strand with the primer strand (4) contacting the sample with labeled imager strands capable of binding a docking strand, either directly or indirectly, wherein the labeled imager strands are provided in a liquid medium or buffer solution (5) optionally removing unbound labeled imager strands, (6) optionally removing liquid to create a liquid-free sample, (7) affixing a second optically-transparent material parallel to the first support, and (8) imaging the sample to detect bound labeled imager strands.

In some embodiments, the second optically-transparent material is glass or plastic. In some instances, the second optically-transparent material is from about 5 microns to 5 mm, from 50 microns to 500 microns, or from 500 microns to 5 mm from the first support. In some instances, the imaging is carried out with an upright microscope.

In some embodiments, optionally removing liquid to create a liquid-free sample comprises preparing the sample for storage, such as long-term storage for at least 4 hours, 1 day, 3 days, 1 week, 2 weeks, or one month. In some embodiments, optionally removing liquid to create a liquid-free sample increases sample handling convenience because the user does not need to keep the sample hydrated.

By optionally removing liquid to create a liquid-free sample, this means removing at least about 90%, 91%, 92%, 93%, 94%, 95%, 96%, 97%, 98%, 99%, or 100% of the liquid in a sample (namely, the liquid previously in the sample and associated with the other sample components, such as the sample itself, the docking strand, the imager strand, etc.). In some embodiments, the mounting medium comprises air. In other embodiments, the mounting media comprises a mounting media in a gel formulation. In some embodiments, the mounting media comprises a formula that begins as a liquid but changes to a gel or solid as time elapses (such as a hardening material, glue, cement, or other optically transparent and similarly-functioning material).

In other embodiments, the liquid in the sample may be replaced by a liquid mounting media such as a saline-based buffered solution (such as PBS).

Mounting media may be used to hold a specimen in place, to prevent a sample from drying out, to more closely match the refractive index of the objective you will use, to prevent photobleaching (when not desired), and to preserve a sample for long-term storage. The choice of mounting media depends on the sample type, the imaging strategy, which observable moiety is used, and the objectives of the user (whether the user wishes to hydrate the sample or whether the user wishes to store the sample).

In some embodiments, a method to test a fixed sample mounted to an optically transparent support for the presence of one or more targets comprises (1) contacting the sample with one or more target-specific binding partners, wherein each target-specific binding partner is linked to a nucleic acid strand and wherein target-specific binding partners of different specificity are linked to different nucleic acid strands, (2) optionally removing unbound target-specific binding partners, (3) wherein the nucleic acid strand is a docking strand or a primer strand and if the nucleic acid is (a) a docking strand, increasing the number of docking strands associated with each target-specific binding partner or (b) a primer strand, associating more than one docking strand with the primer strand, (4) contacting the sample with labeled imager strands capable of binding a docking strand, either directly or indirectly, (5) optionally removing unbound labeled imager strands, (6) optionally removing liquid to create a liquid-free sample, (7) affixing a second optically-transparent material parallel to the first support, and (8) imaging the sample to detect bound labeled imager strands.

In the various multiple embodiments, the optically transparent support and the second optically transparent material parallel to the first support may comprise a flow cell. In the various multiple embodiments, by parallel, it includes geometrical arrangements that are perfectly parallel, as well as those that deviate from parallel by up to 1°, 2°, 3°, 4°, 5°, 6°, 7°, 8°, 9°, or 10°.

3. Sample Reinterrogation

In some embodiments, users may desire to reinterrogate a sample for the same target multiple times. When reinterrogation is desired, the multiplex imaging is conducted by conducting another round of imaging with the same imager stand. Thus, when a user desires to image different targets, the imager strand has a unique nucleotide sequence relative to all other labeled imager strands. When a user desires to image the same target multiple times, the repeated steps use an imager strand that does not have a unique nucleotide sequence relative to all other labeled imager strands, but instead has the same sequence as a previously employed imager strand.

Thus, in some embodiments, a method comprises (1) contacting a sample being tested for the presence of one or more targets with one or more target-specific binding partners, wherein each target-specific binding partner is linked to a nucleic acid strand and wherein target-specific binding partners of different specificity are linked to different nucleic acid strands, (2) optionally removing unbound target-specific binding partners, (3) wherein the nucleic acid strand is a docking strand or a primer strand and optionally if the nucleic acid is (a) a docking strand, increasing the number of docking strands associated with each target-specific binding partner or (b) a primer strand, associating more than one docking strand with the primer strand, (4) contacting the sample with labeled imager strands capable of binding a docking strand, either directly or indirectly, (5) optionally removing unbound labeled imager strands, (6) imaging the sample to detect presence, location, and number of bound labeled imager strands, (7) extinguishing signal from the bound labeled imager strand, and (8) repeating steps (3)-(6) or (3)-(7), with a labeled imager strand optionally having a unique nucleotide sequence relative to all other labeled imager strands.

4. Spectral and Sequential Multiplexing

Two main methods exist for creating multiplexing in exchange imaging: spectral multiplexing and sequential multiplexing. Spectral multiplexing refers to the ability to use different labels (such as different fluorophores) in a single round of imaging. Spectral multiplexing does not necessitate extinguishing the signal from the first label before viewing the second label. For example, in the case of fluorophores, different excitation wavelengths of light can be used to individually excite different fluorophores. This does not require separate rounds of imaging. Sequential multiplexing refers to the ability to use the same labels (such as the same fluorophore) in multiple rounds of imaging by extinguishing the signal from the first round of imaging before the second round of imaging. Spectral multiplexing and sequential multiplexing can either be used alone or in conjugation with each other. Using more than one technique of multiplexing, however, can significantly increase the number of targets that a user can visualize during a particular experiment.

In some embodiments, multiple rounds of imaging are performed with at least some of the same fluorophores. For example, in a first round of imaging, target A can be imaged with label X, target B can be imaged with label Y, and target C can be imaged with label Z. As a next step, the signals from these labels can be extinguished. Then, in a second round of imaging, target D can be imaged with label X, target E can be imaged with label Y, and target F can be imaged with label Z. Item In some embodiments, at least two targets are imaged using at least two labels, the signal extinguished, and then at least one more target is imaged using at least one of the same labels, wherein the imaging steps may be performed in either order. This means that the order of steps could be reversed so the first imaging step comprises imaging at least one target, the signal extinguished, and the second imaging step comprises imaging at least two targets.

Combining both spectral multiplexing and sequential multiplexing can increase the overall convenience of performing the imaging for the user and reduce disruption to the sample being imaged.

C. Stable Binding

In some embodiments, at least some of the complementary agents used in imaging are stably binding to each other and in other embodiments, all the complementary agents used in imaging are stably binding to each other. In some embodiments, the docking strand is stably bound to the imager strand. In some embodiments, the amplifier strand is stably bound to the docking strand. In some embodiments, the amplifier strand is stably bound to the imager strand.

In some embodiments, the intermediate strand is stably bound to the docking strand. In some embodiments, the intermediate strand is stably bound the amplifier strand. In some embodiments, the intermediate strand is stably bound the imager strand. In some embodiments, the amplifier strand is stably bound to the imager strand. In some embodiments, the primer strand is stably bound to the docking strand.

In some embodiments, a composition comprises a sample bound to more than one target-specific binding partners, each binding partner bound to a docking strand, and at least one docking strand stably bound to a labeled imager strand.

In some embodiments, the stable binding comprises at least the percentage binding for the time recited in Table 2. For example, Table 2 includes 90% binding for at least 30 minutes. This means that of the items bound at t=0, 90% of the items stay bound for at least 30 minutes. This also means that an equilibrium is achieved that has at least 90% of the docking strand bound to imager strand, for example, at any one time and no more than 10% unbound. The stable binding can include an unbinding of some molecules and a rebinding of other molecules to achieve a population binding percentage; it does not require that at least 90% are permanently bound, it only requires that at any one time at least 90% are bound. Stable binding also can include, wherein V is a variable amount of time corresponding to the length required for the user's experiment and an x means that percentage bound for the length of time qualifies as stable binding:

TABLE 2

Stable Binding

| | | time (T) bound (at least) | | | | | | | | | | |
|---|---|---|---|---|---|---|---|---|---|---|---|---|
| | | minutes | | | | | | hours | | | days | |
| | V | 5 | 10 | 20 | 30 | 40 | 50 | 60 | 3 | 8 | 24 | 48 | 7 |
| Percentage bound at time T | 50 | x | x | x | x | x | x | x | x | x | x | x | x |
| | 60 | x | x | x | x | x | x | x | x | x | x | x | x |
| | 65 | x | x | x | x | x | x | x | x | x | x | x | x |
| | 70 | x | x | x | x | x | x | x | x | x | x | x | x |
| | 75 | x | x | x | x | x | x | x | x | x | x | x | x |
| | 80 | x | x | x | x | x | x | x | x | x | x | x | x |
| | 85 | x | x | x | x | x | x | x | x | x | x | x | x |
| | 90 | x | x | x | x | x | x | x | x | x | x | x | x |
| | 91 | x | x | x | x | x | x | x | x | x | x | x | x |
| | 92 | x | x | x | x | x | x | x | x | x | x | x | x |
| | 93 | x | x | x | x | x | x | x | x | x | x | x | x |
| | 94 | x | x | x | x | x | x | x | x | x | x | x | x |
| | 95 | x | x | x | x | x | x | x | x | x | x | x | x |
| | 96 | x | x | x | x | x | x | x | x | x | x | x | x |
| | 97 | x | x | x | x | x | x | x | x | x | x | x | x |
| | 98 | x | x | x | x | x | x | x | x | x | x | x | x |
| | 99 | x | x | x | x | x | x | x | x | x | x | x | x |
| | 100 | x | x | x | x | x | x | x | x | x | x | x | x |

For example, stably bound may include 70%, 80%, or 90% binding at from about 5 minutes to 7 days, 10 minutes to 60 minutes, 20 minutes to 3 hours, 30 minutes to 24 hours, 3 hours to 24 hours, or 24 hours to 7 days.

The values in Table 2 apply to all types of stable binding discussed above. Such measurements may be taken at imaging conditions (in some situations room temperature, neutral pH, and physiological buffer conditions), after non-reactive buffer wash(es), or after a non-enzymatic buffer wash(es).

In some embodiments, the docking strand, primer strand, or intermediate strand engaging in stable binding comprises 30 nucleotides or less, such as from about 8 to 30 nucleotides, from 10 to 25 nucleotides, or from 10 to 20 nucleotides. In some embodiments, the imager strand engaging in stable binding comprises 30 nucleotides or less, such as from about 8 to 30 nucleotides, from 10 to 25 nucleotides, or from 10 to 20 nucleotides. In some embodiments, the amplifier strand is from about 30 to 60 nucleotides, 20 to 80 nucleotides, 30 to 70 nucleotides, 30 to 60 nucleotides or more than 60 nucleotides. The type of amplification reaction can also impact the length of the amplifier strand desired, with longer lengths desired for hybridization chain reaction (HCR), for example. The person of ordinary skill in the art will recognize that the composition of different bases in the docking strand, imager strand, and/or amplifier strand will impact the number of nucleotides desired in each strand due to affinity differences. Temperature will also impact the number of nucleotides desired.

1. Proximity Imaging with Stable Binding

In some embodiments, a user may employ proximity imaging with stable binding. In some embodiments, a composition comprises: (a) at least one first binding partner-oligonucleotide conjugate comprising a binding partner linked to an oligonucleotide that comprises a half-docking domain, an optional stability domain, and optionally a spacer domain; (b) at least one second binding partner-oligonucleotide conjugate comprising a binding partner linked to an oligonucleotide that comprises a half-docking domain, an optional stability domain, and optionally a spacer domain; wherein the stability domains of (a) and (b) are complementary to each other, and wherein the half-docking domains of (a) and (b) can combine linearly to form a full docking domain; and (c) at least one labeled imager strand or intermediate strand comprising a 5' domain, a 3' domain, and a linker domain located between the 5' domain and the 3' domain, wherein the 5' domain is complementary to the half-docking domain of (a) and the 3' domain is complementary to the half-docking domain of (b), and wherein the labeled imager strand or intermediate strand capable of being stably bound to the full docking domain and if an intermediate strand is used also providing a labeled imager strand. Alternatively, an intermediate strand may be used and be complementary to both the docking strand and the imager strand. Amplification may also be employed. The stability criteria set forth in Table 2 also apply in this context.

In some embodiments, a user may employ proximity imaging with stable binding when employing a primer. In some embodiments, a composition comprises: (a) at least one first binding partner-oligonucleotide conjugate comprising a binding partner linked to an oligonucleotide that comprises a half-primer domain, an optional stability domain, and optionally a spacer domain; (b) at least one second binding partner-oligonucleotide conjugate comprising a binding partner linked to an oligonucleotide that comprises a half-primer domain, an optional stability domain, and optionally a spacer domain; wherein the stability domains of (a) and (b) are complementary to each other, and wherein the half-primer domains of (a) and (b) can combine linearly to form a full primer domain; (c) at least one docking strand capable of being stably bound to the full primer domain; and (d) at least one labeled imager strand capable of being stably bound to the docking strand or an intermediate strand capable of being stably bound to the docking strand and a labeled imager strand capable of being stably bound to the intermediate strand. The docking strand capable of being stably bound to the full primer domain includes complementary binding (noncovalent) and extending from the same nucleic acid strand (covalent binding). In embodiments where the docking strand is noncovalently bound to the full primer domain and has a complementary nucleic acid sequence, the docking strand may comprise a 5' domain, a 3' domain, and a linker domain located between the 5' domain and the 3' domain, wherein the 5' domain is complementary to the half-primer domain of (a) and the 3' domain is complementary to the half-primer domain of (b). In embodiments where the docking strand is covalently bound, it may be extended out from the full primer domain by nucleic acid synthesis. Additionally and alternatively, an intermediate strand may be used and be complementary to both the docking strand and the imager strand. Amplification may also be employed. The stability criteria set forth in Table 2 also apply in this context.

D. Control Experiments and Background Subtraction

Control experiments and background subtraction may be employed to further improve the results of the methods of testing a sample for the presence of one or more targets. Neither of these aspects are required for useful experimentation; however, both improve the quality of multiplexing and can be used alone or in conjunction with each other.

1. Control Experiments

Control measurements may be added at multiple time points in a multiplexed process. In some embodiments, a method to test a fixed sample mounted to an optically transparent support for the presence of one or more targets comprises (1) contacting the sample with one or more target-specific binding partners, wherein each target-specific binding partner is linked to a nucleic acid strand and wherein target-specific binding partners of different specificity are linked to different nucleic acid strands, (2) optionally removing unbound target-specific binding partners, (3) wherein the nucleic acid strand is a docking strand or a primer strand and optionally if the nucleic acid is (a) a docking strand, increasing the number of docking strands associated with each target-specific binding partner or (b) a primer strand, associating more than one docking strand with the primer strand, (4) contacting the sample with labeled imager strands capable of binding a docking strand, either directly or indirectly, such as through an intermediate strand, (5) optionally removing unbound labeled imager strands, (6) imaging the sample to detect bound labeled imager strands, (7) extinguishing signal from the bound labeled imager strand, (8) performing a control step by contacting the sample with labeled imager strands having a nucleotide sequence that is not complementary to a docking strand or intermediate strand (i.e., one actually present in the method, if used, not a hypothetical intermediate strand), (9) optionally removing unbound labeled imager strands, (10) imaging the sample to detect bound labeled imager strands, and (11) optionally extinguishing signal from the bound labeled imager strand.

In some embodiments, a method to test a fixed sample mounted to an optically transparent support for the presence of one or more targets comprises (1) contacting the sample with one or more target-specific binding partners, wherein each target-specific binding partner is linked to a nucleic acid strand and wherein target-specific binding partners of different specificity are linked to different nucleic acid strands, (2) optionally removing unbound target-specific binding partners, (3) wherein the nucleic acid strand is a docking strand or a primer strand and optionally if the nucleic acid is (a) a docking strand, increasing the number of docking strands associated with each target-specific binding partner or (b) a primer strand, associating more than one docking strand with the primer strand, (4) performing a control step by contacting the sample with labeled imager strands having a nucleotide sequence that is not complementary to a docking strand or intermediate strand (i.e., one actually present in the method, if used, not a hypothetical intermediate strand), (5) optionally removing unbound labeled imager strands, (6) imaging the sample to detect presence, location, and/or number of bound labeled imager strands, (7) extinguishing signal from the bound labeled imager strand, (8) contacting the sample with labeled imager strands capable of binding a docking strand, either directly or indirectly, such as through an intermediate strand (9) optionally removing unbound labeled imager strands, (10) imaging the sample to detect presence, location, and/or number of bound labeled imager strands, and (11) optionally extinguishing signal from the bound labeled imager strand.

In either of the above two embodiments, in some instances, the method further comprises repeating steps (4)-(11). In some embodiments, the user would not repeat the control steps. In other embodiments, the user would repeat the control steps to assess noncomplementary binding.

In some of these embodiments, the labeled imager strand complementary to the docket strand used in the repeated steps optionally has a unique nucleotide sequence relative to at least one other labeled imager strands.

In some embodiments, the control experiment is used to assess crossbinding of noncomplementary strands to ensure in an example assessing targets A, B, and C (for example) that the imager strand (imager A) intended to bind to the docking strand (docking A) affixed to the target-specific binding partner (anti-A) for target A does not interact with the docking strand affixed to the target-specific binding partner for B (imager B) or to measure the degree of its interaction. In such embodiments, repeated processes may evaluate the interaction of imager C with docking strand A, etc. In these embodiments, the complementary strand (imager A binding to docking A) would not necessarily be repeated.

2. Background Subtraction

In any of the embodiments discussed throughout this application, the method may employ background subtraction. In some embodiments, the method comprises imaging the sample to detect and/or measure a background signal and subtracting the background signal from the image of the sample to detect bound labeled imager strands. Such background signals may include autofluorescence and/or residual fluorescence associated with incompletely extinguishing signal from the bound labeled imager strands. In some aspects, the background signal is measured before the image of the sample to detect bound labeled imager strands. In other aspects, the background signal is measured after the image of the sample to detect bound labeled imager strands.

E. Methods of Extinguishing Signal from the Bound Labeled Imager Strand

Various methods can be used to extinguish a signal from a bound labeled imager strand and this may be desired so that the same type of detectable moiety (such as a fluorophore) may be used on multiple imager strands so that the experiment is not spectrally limited.

In other words, removing the set of imager strands or inactivating the observable moieties on the imager strands allows for spectrally-unlimited multiplex imaging. Some prior methods of multiplex imaging were limited by the number of colors of fluorophores or other imaging agents available. Removing the imager strands, removing labels from imager strands, or inactivating the observable moieties allows for reuse of the same colors of fluorophores in a single experiment. In some embodiments, ideally, as much of the signal should be removed to ensure as low backgrounds as possible for continued imaging. In some embodiments, 100% of the prior signal-generating moiety is removed or destroyed, while in some embodiments at least about 90%, 91%, 92%, 93%, 94%, 95%, 96%, 97%, 98%, or 99% of the prior signal-generating moiety is removed or destroyed.

Thus, extinguishing the signal from the labeled imager strand includes any method for removing the imager strand from binding, directly or indirectly, to the docking strand, removing the label from the imager strand, or inactivating the label on the imager strand.

All methods for extinguishing the signal from imager strands may be applied to docking strands as well. In some embodiments, extinguishing the signal from the bound labeled imager strand involves disrupting the link between docking strand (or primer strand) and target-recognition moiety. In some embodiments, the docking strand comprises a photocleavable linker that can be cleaved photochemically (e.g. by UV exposure, visible light, infrared, near infrared, x-ray, microwave, radio waves, or gamma rays). In some embodiments, the docking strand (or primer strand) itself contains a moiety that can be cleaved by an enzyme. Examples of such enzymatically cleavable moieties include but are not limited to ribonucleotides, which can be cleaved by a variety of RNases; deoxyuridines, which can be cleaved by enzyme combinations such as USER (New England Biolabs); and restriction sites, which can be cleaved by sequence-specific nicking enzymes or restriction enzymes. In some embodiments, the docking nucleic acid comprises a deoxyuridine, in which the uracil group may be cleaved by uracil-DNA glycosylase. In some embodiments, the docking nucleic acid comprises an abasic site, which may be cleaved by endonuclease.

One non-limiting example of Exchange Imaging is DNA Exchange Immunofluorescence, where one uses antibodies as the target-recognizing molecules to image target proteins or other biomolecules, uses DNA oligonucleotides as docking strands, and uses DNA oligonucleotides that are complementary to the docking strands and labeled with fluorophores as the imager strands. A user may extinguish the signal from the labeled imager strand by using high temperature, denaturant, DNA helicase, DNase, and/or strand displacement, or may remove the fluorophores on the imager strands by chemical cleavage, enzymatic cleavage, chemical bleaching, photo-bleaching, and/or photochemical bleaching.

1. Nucleic Acid-Degrading Enzymes

A number of enzymes can break the covalent bonds within a nucleic acid molecule. For example, some glycosylase can remove the base from the sugar moiety of a nucleotide, endonuclease can cut the bond within the phosphodiester bridge inside the nucleic acid molecule, while exonuclease can similarly break the phosphodiester bridge at the 5' or 3' terminal of the nucleic acid molecule in a sequential fashion. Another example comprises DNAzymes or deoxyribozymes, oligonucleotides with catalytic activity capable of cleaving the phosphodiester bond in nucleic acid molecules. All these types of enzymes may be engineered for imager strand removal (FIG. 5) and constitute enzymatically cleaving, modifying, or degrading the labeled imager strand nucleic acids.

Glycosylase.

If a glycosylase can specifically remove a base that participates the base-pairing between the Docking Strand and the Imager Strand, it can reduce the strength of interaction between the two strands. For example, one can use deoxyuridine (dU) to replace deoxythymidine (dT) in the Imager Strand. dU can pair with dA in the Docking Strand just like the dT does, but can be specifically removed by Uracil-DNA Glycosylase (UDG, commercially available from New England Biolabs, Cat #M0280S). This reaction will result in abasic site(s) on the Imager Strand. Such abasic sites can be further cleaved by Endonuclease VIII. This will further promote the dissociation between the remnant of Imager Strand and the Docking Strand. Enzyme blend comprising both UDG and Endonuclease VIII is also commercially available (e.g., from New England Biolabs, under the tradename USER, Cat #M5505S). One may place from about 1 to 20, 1 to 15, 1 to 10, or 1 to 5 dU nucleotides in the Imager Strand. With USER, the dUs may be placed in a way that after removal of U, the remnants are short enough (e.g., less than or equal to about 9, 8, 7, 6, 5, 4, 3, 2, or 1 nucleotides) that they dissociate spontaneously and quickly. If only UDG (i.e., no Endonuclease VIII) is used, the removal of dU units could destabilize the strand enough to facilitate removal. Total number of base pairs between the imager strand and docking strand after dU removal may be less than or equal to 9, 8, 7, 6, 5, 4, 3, 2, or 1 nucleotides. Thus, in some embodiments the imager strand or intermediate strand may comprise at least one U capable of cleavage by USER.

The sequence of the remnants, as well as the temperature, will impact how short the remnants should be to dissociate spontaneously. For example, a sequence high in GC content might have more binding affinity at a shorter length than another sequence at a longer length. Thus, in some instances, a 9-mer may be sufficient for stable binding and in other instances a 9-mer may be sufficient to dissociate. A person of ordinary skill in the art can evaluate the sequences, temperatures, and affinities, here and in the cleavage of non-natural nucleotides discussed below.

Restriction endonuclease and nicking endonuclease.

One may engineer a restriction site in the docking strand: imager strand duplex. This allows the usage of the corresponding restriction endonuclease to cut such restriction site, which breaks the linkage between the target and the signal-generating moiety of the imager strand. As an example, Cas9 (CRISPR associated protein 9) is a RNA-guided endonuclease that can be used to specifically cleave docking: imager strand duplexes, by engineering a specific recognition site in the corresponding sequences. This results in both strands being cleaved, preventing one from re-interrogating the corresponding target. To solve this problem, one can use nicking endonuclease which only cut one strand. As an example, Cas9 nickases are Cas9 enzymes that have been engineered to only include one active cleaving site, leading to single strand cuts, while conserving the high specificity of Cas9. One can design the restriction site in a way that only the imager strand is cut, and that the remnant of imager strand that carries the signal-generating moiety is sufficiently short (e.g., <7 nucleotide) that it dissociates spontaneously and quickly from the docking strand. Other examples of endonucleases with site specific activity include but are not limited to: zinc finger nucleases, transcription activator-like effector nucleases (TALENs), and deoxyribozymes.

Rnase.

One may make some or all of nucleotides in the imager strand RNA nucleotides (also called ribonucleotides), instead of DNA nucleotides (also called deoxynucleotide). Such RNA nucleotides can be removed by Rnase. If the docking strand is comprised of DNA nucleotides and the imager strand contains RNA nucleotides, such RNA nucleotides in the DNA:RNA heteroduplex can be removed by Rnase H.

Polymerase.

Figure 6A:
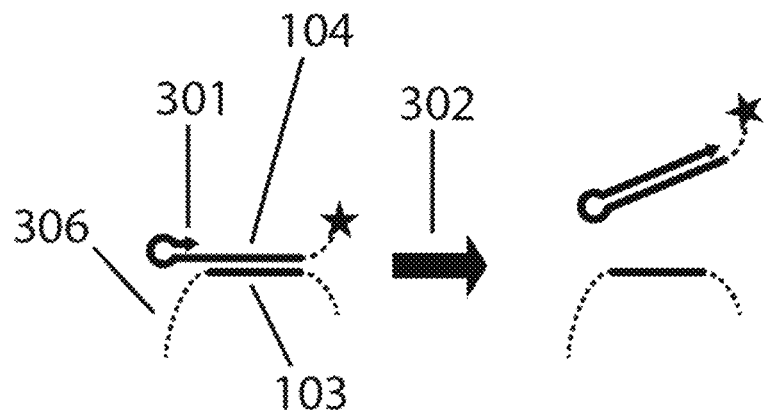
FIGS. 6A-F shows removal of Imager Strand using polymerase enzymes.
Figure 6B:
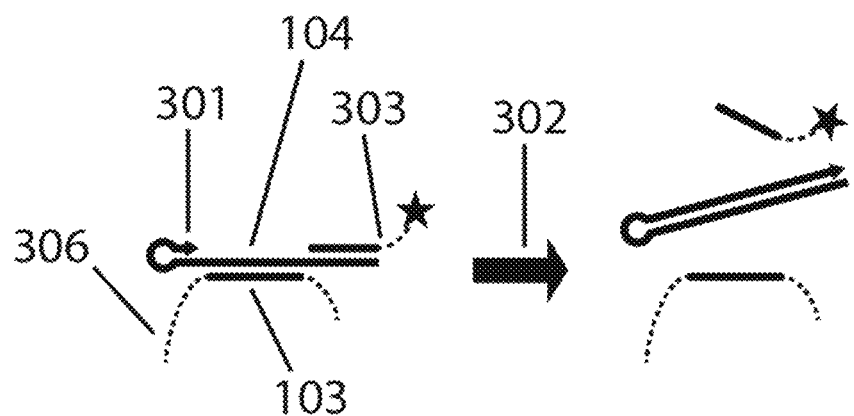
Figure 6C:
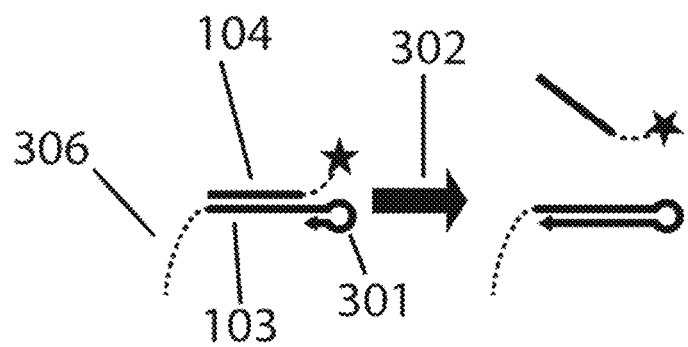
Figure 6D:
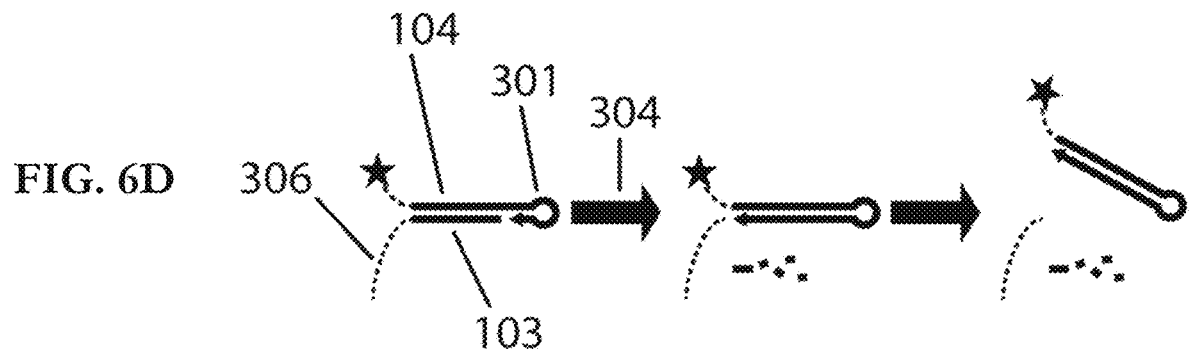
Figure 6E:
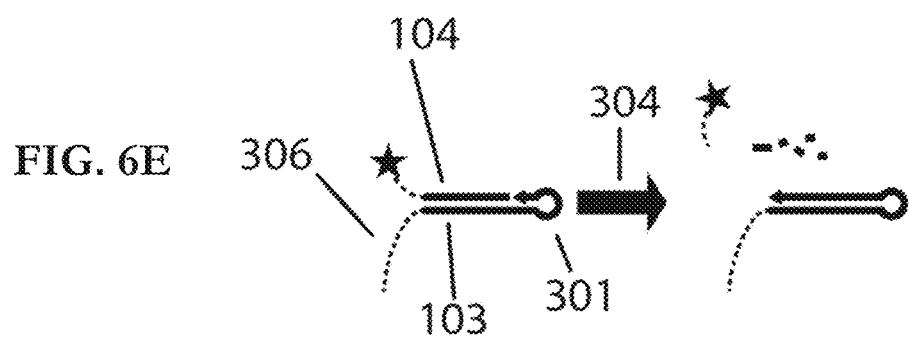
Figure 6F:
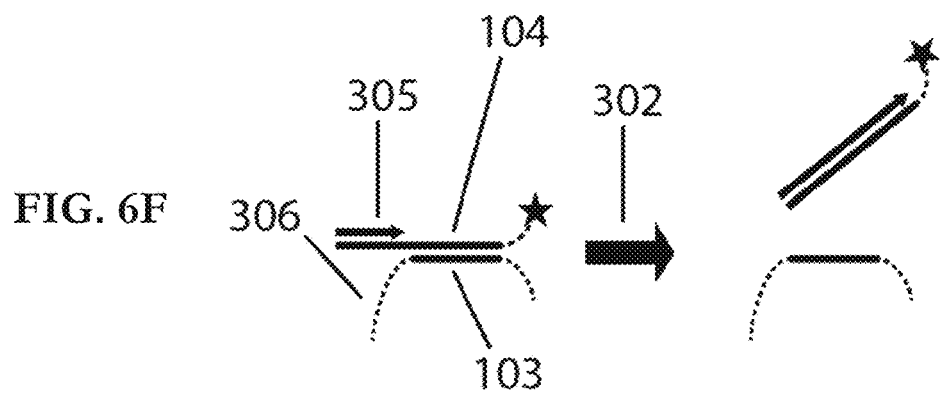

The imager strand can also be removed by using polymerases with strand-displacement activity or 5'-to-3' exonuclease activity. For example, one can engineer a hairpin structure at the 3' end of the docking strand made of DNA. When a DNA polymerase with strand displacement activity (e.g., Phi29, Bst, Vent) is introduced and supplied with suitable buffer and dNTPs, the 3' of the docking strand can be extended, during which the imager strand is displaced (FIG. 6c). The self-priming hairpin can also be engineered on the imager strand (FIG. 6a-b), for which the signal-general moiety can be either attached to the imager strand directly (FIG. 6a), or attached to the imager strand via DNA hybridization (FIG. 6b). When a DNA polymerase with 5'-to-3' exonuclease activity (e.g., DNA polymerase I, Taq) is introduced and supplied with suitable buffer and dNTPs, and a self-priming hairpin is engineered at the 3' end of the docking strand, the 3' can be extended, during which the imager strand is degraded (FIG. 6e) Similar effect can be achieved if the self-priming hairpin is engineered at the 3' end of the imager strand (FIG. 6d). Note that the self-priming hairpin can also be replaced by a stable duplex (e.g., FIG. 6f).

Cleavage of Non-Natural Nucleotides.

Non-natural nucleotide that serve as substrates for particular enzymes may be used. For example, 8-oxoguanine may be cleaved by DNA glycosylase OGG1. Abasic sites may also be incorporated into a DNA strand, such as an imager strand, which may be cleaved by an endonuclease. For example, a 1',2'-Dideoxyribose, dSpacer, apurinic/apyrimidinic, tetrahydrofuran, or abasic furan may be cleaved by Endonuclease VIII. Thus, in some embodiments the imager strand or intermediate strand may comprise at least one abasic site capable of cleavage by Endonuclease VIII. In some embodiments the imager strand or intermediate strand may comprise at least one deoxyuridine and at least one abasic site capable of cleavage by USER, UDG, or Endonuclease VIII. Photocleavable spacers or RNA abasic sites may also be used, such as ribospacer (rSpacer) or Abasic II modification. Other pairs of non-natural nucleotides and their paired enzymes may be employed.

Thus in some embodiments, a composition comprises (1) a label, (2) a first nucleic acid domain, a second nucleic acid domain, and a third nucleic acid domain, wherein each nucleic acid domain is from about 1 to 9 nucleotides long (for example, about 9, 8, 7, 6, 5, 4, 3, 2, or 1 nucleotides), (3) a first linking moiety linking the first nucleic acid domain and the second nucleic acid domain and (4) a second linking moiety linking the second nucleic acid domain and the third nucleic acid domain, wherein both linking moieties are independently chosen from (a) an abasic site with an intact phosphodiester backbone, (b) a linker cleavable by a nucleic acid glycosylase, or (c) a restriction site or nicking site. In some embodiments, additional nucleic acid domains are linked by additional linking moieties. In some embodiments, at least one linking moiety is an abasic site (apyrimidinic) with an intact phosphodiester backbone. In some embodiments, at least one linking moiety is susceptible to cleavage from Endonuclease VIII. In some embodiments, the nucleic acid domains comprise DNA and in some the nucleic acid domains comprise RNA. In some aspects, at least one linking moiety comprises at least one non-natural nucleotide. In some aspects, at least one linking moiety comprises 8-oxoguanine.

In some embodiments, methods of removing imager strand may be combined with amplification steps. In some embodiments, a method to test a sample for the presence of one or more targets comprises (1) contacting the sample with one or more target-specific binding partners, wherein each target-specific binding partner is linked to a nucleic acid strand, directly or indirectly and wherein target-specific binding partners of different specificity are linked to different nucleic acid strands, (2) optionally removing unbound target-specific binding partners, (3) wherein the nucleic acid strand is a docking strand or a primer strand and if the nucleic acid is (a) a docking strand, increasing the number of docking strands associated with each target-specific binding partner or (b) a primer strand, associating more than one docking strand with the primer strand, (4) contacting the sample with labeled imager strands capable of binding a docking strand, directly or indirectly, wherein the labeled imager strands comprise the composition described immediately above, (5) optionally removing unbound labeled imager strands, (6) imaging the sample to detect bound labeled imager strands, (7) removing the bound labeled imager strands from the docking strands, wherein the labeled imager strands are removed from the docking strands by enzymatically cleaving, modifying, or degrading the labeled imager nucleic acids, and (8) optionally repeating steps (1)-(7), or any subset thereof.

In some aspects, the labeled imager nucleic acids are removed by enzymatically cleaving the labeled imager strand.

F. Description of Samples

1. Types of Samples

Various types of samples may be imaged using these methods. In some embodiments, the sample is a fixed sample. In some embodiments, the sample is a cell, cell lysate, tissue, tissue lysate, and or a whole organism. In some embodiments, the sample is a cell or tissue sample, a cell or tissue lysate, or a bodily fluid. In some embodiments, the sample is tissue and the imaging comprises in-tissue multiplexing for immunostaining.

The sample may be provided in a liquid medium or buffer solution.

2. Antigen Retrieval

In some embodiments, staining a sample with a target-specific binding partner requires specific conditions and not all target-specific binding partners will bind to their antigens under the same conditions. This may be because their target antigens are not available under the same conditions.

Thus in some embodiments, a method to test a sample for the presence of one or more targets comprises (1) treating the sample to expose one or more previously unavailable targets, (2) contacting the sample with one or more target-specific binding partners, wherein each target-specific binding partner is linked to a nucleic acid strand, and wherein target-specific binding partners of different specificity are linked to different nucleic acid strands, (3) optionally removing unbound target-specific binding partners, (4) wherein the nucleic acid strand is a docking strand or a primer strand and optionally if the nucleic acid is (a) a docking strand, increasing the number of docking strands associated with each target-specific binding partner or (b) a primer strand, associating more than one docking strand with the primer strand, (5) contacting the sample with labeled imager strands capable of binding a docking strand, directly or indirectly, (6) optionally removing unbound labeled imager strands, (7) imaging the sample to detect bound labeled imager strands, (8) extinguishing signal from the bound labeled imager strand, and (9) optionally repeating steps (1)-(8), each time (a) exposing a different set of previously unavailable targets (b) using one or more different target-specific binding partners and (c) using a labeled imager strand having a unique nucleotide sequence relative to at least one other labeled imager strand.

3. Description of Targets and Use in Identifying Biomarkers

In some embodiments, the method is useful for identifying a biomarker. In some instances, samples are imaged and data analysis performed on those samples. In some embodiments, multiple targets are tested for using corresponding target-specific binding partners for each target. In some instances, the relationship between different targets may be assessed; for example, a user might seek to determine the relationship of multiple markers to a disease state and conclude that the disease sample has increased levels of A, decreased levels of B, and levels of C within a certain range, as compared to healthy tissue that does not have that biomarker distribution.

In some embodiments, at least 10, 96, 100, 384, or 500 samples are imaged and data analysis performed on those samples.

In some embodiments, at least 5, 10, 15, 25, 30, 50, 75, or 100 or more targets are tested for using corresponding target-specific binding partners for each target.

G. Equipment and Software

1. Imaging Chamber, Such as a Flow Cell

In some embodiments, an imaging chamber can be employed. In some instances, an imaging chamber is a fixed chamber with no inlet and no outlet. In some embodiments, an imaging chamber has a single inlet/outlet combination. In other instances, an imaging chamber allows for flow and is designated a flow cell. A flow cell may be comprised of a first optically transparent support in combination with a second optically transparent material (such as a glass or plastic coverslip) to provide a flow cell with a top and bottom surface and fluid flow between them. If a first and second optically transparent material are used, they may be placed parallel to each other. By parallel, it includes geometrical arrangements that are perfectly parallel, as well as those that deviate from parallel by up to 1°, 2°, 3°, 4°, 5°, 6°, 7°, 8°, 9°, or 10°. In some embodiments, the second optically transparent material is in close proximity to the first optically transparent material, such as about 5 microns to 5 mm, from 50 microns to 500 microns, or from 500 microns to 5 mm.

An imaging chamber may also be comprised of a first optically transparent support and a gasket (also referred to as an isolator or spacer). The gasket may be open to the air on the top surface or it may be closed and have an optically transparent top surface. The gasket may have a combined inlet/outlet or it may have both an inlet and an outlet. The gasket may also have no outlet. The gasket may be plastic, rubber, adhesive. A gasket may comprise a CoverWell Chamber Gasket (Thermo Fisher), an ultra-thin sealed chamber for upright and inverted microscopes (Bioscience Tools), or an incubation chamber (Grace Bio-Labs, including HybriSlip™ hybridization covers, HybriWell™ sealing system, CoverWell™ incubation chambers, imaging spacers, SecureSeal™ hybridization chambers, FlexWell™ incubation chambers, FastWells™ reagent barriers, and Silicone Isolators™).

In some instances, a gasket may be employed along with a coverslip forming the top surface of an imaging chamber or flow cell.

Imaging chambers, such as but not limited to flow cells, may be reusable or disposable.

Thus, in some embodiments, a method to test a fixed sample mounted to a first optically transparent support for the presence of one or more targets comprises (1) contacting the sample with one or more target-specific binding partners, wherein each target-specific binding partner is linked to a nucleic acid strand and wherein target-specific binding partners of different specificity are linked to different nucleic acid strands, (2) optionally removing unbound target-specific binding partners, (3) wherein the nucleic acid strand is a docking strand or a primer strand and optionally if the nucleic acid is (a) a docking strand, increasing the number of docking strands associated with each target-specific binding partner or (b) a primer strand, associating more than one docking strand with the primer strand, (4) in an imaging chamber (such as a flow cell), contacting the sample with labeled imager strands capable of binding a docking strand, directly or indirectly, (5) optionally removing unbound labeled imager strands, (6) imaging the sample to detect presence, location, and/or number of bound labeled imager strands and optionally removing the imaging chamber, (7) extinguishing signal from the bound labeled imager strand, and (8) repeating steps (4)-(6) or (4)-(7), at least once with a labeled imager strand optionally having a unique nucleotide sequence relative to at least one other labeled imager strands.

A method to image a fixed sample mounted to an optically transparent support comprising (1) contacting the sample with one or more target-specific binding partners, wherein each target-specific binding partner is linked to a nucleic acid strand, and wherein target-specific binding partners of different specificity are linked to different nucleic acid strands, (2) optionally removing unbound target-specific binding partners, (3) wherein the nucleic acid strand is a docking strand or a primer strand and if the nucleic acid is (a) a docking strand, increasing the number of docking strands associated with each target-specific binding partner or (b) a primer strand, associating more than one docking strand with the primer strand, (4) contacting the sample with labeled imager strands capable of binding a docking strand, either directly or indirectly, (5) optionally removing unbound labeled imager strands, (6) optionally removing liquid to create a liquid-free sample, (7) affixing a second optically-transparent material in close proximity to (namely about 5 microns to 5 mm, from 50 microns to 500 microns, or from 500 microns to 5 mm) and parallel to the first support, and (8) imaging the sample to detect bound labeled imager strands.

2. Software for Control of Fluidic Steps

In some embodiments, all fluidic exchange steps are performed using a fluidic system comprising electronic, and/or pneumatic, and/or hydraulic, and/or electro-fluidic actuators and systems. In certain situations, the fluidic system is controlled by software. In some embodiments, wherein the fluidic system is automatically controlled by software synchronizing steps (1 (contacting a sample with target-specific binding partners) and/or 2 (optionally removing unbound target-specific binding partners) and/or 3 (increasing the number of docking strands, or amplification) and/or 4 (contacting the sample with labeled imager strands capable of binding a docking strand, directly or indirectly) and/or 5 (optionally removing unbound labeled imager strands), and/or 7 (optionally removing the bound labeled imager strands from the docking strands) with the imaging step (6).

In some embodiments, the fluidic system is controlled by software synchronizing the steps (1 and/or 2 and/or 3 and/or 4 and/or 5, and/or 7) with the imaging step (6) by communicating with the imaging software, with the references to step numbers described in the preceding paragraph.

In some embodiments, all fluidic steps are performed while the sample is on the imaging device. In some embodiments, steps 4, 5, and 7 are performed while the sample is on the imaging device, with the references to step numbers described two paragraphs previously.

The sample may be fixed in a disposable imaging chamber (such as a flow cell) or a reusable imaging chamber (such as a flow cell).

H. Kits

In some embodiments, a composition comprises (1) one or more reagent(s) including but not limited to target-specific binding partners linked to docking-strands, wherein target-specific binding partners of different specificity are linked to different docking strands, labeled imager strands, buffers, amplification reagents, and/or reagents to remove bound imager strands, (2) a fluidic system to perform all fluid exchange steps, a software to control the fluidic system and time and/or synchronize the fluidic steps with the imaging steps, (3) an imaging chamber (such as a flow cell) to affix on the sample of interest with at least one optically transparent side to allow imaging of the sample. In some embodiments, the imaging chamber (such as a flow cell) is disposable.

II. Components of the Method

A. Target-Specific Binding Partners

The target recognition moiety refers to antibodies and antibody-like molecules that can be used to detect the target molecule. Antibody refers to any immunoglobulin from any species that can specifically recognize a target molecule. Antibody-like molecule refers to (Class A) any engineered variation or fragment of an antibody such as Fab, Fab', F(ab')$_2$, single heavy chain, diabody, and the like (antigen binding fragments of antibodies) (Class B) any known binding partner of a target molecule and engineered variants of such binding partner, (Class C) any binding partner of the target molecule engineered via directed evolution (e.g., peptides and aptamers), and (Class D) any molecule that selectively forms covalent bond(s) with a target (e.g., a suicide substrate of an enzyme of interest).

The target-specific binding partner may be provided in a liquid medium or buffer solution.

Table 3 provides a representative listing of targets and corresponding target recognition moieties.

TABLE 3

Representative Targets and Target Recognition Moieties

| Target | Target Recognition Moiety | Source or Sequence |
|---|---|---|
| Any protein | Antibody (Class A) | Variable |
| Fluorescein (chemical compound) | Antibody (Class A) | Abcam, product # ab7253 |
| Digoxigenin (chemical compound) | Antibody (Class A) | Abcam, product # ab76907 |
| Biotin | Avidin/Streptavidin (Class B) | |
| Epidermal growth factor receptor (EGFR, protein) | Epidermal growth factor (EGF, Class B) | |
| Platelet-derived growth factor receptor (PDGFR, protein) | Platelet-derived growth factor (PDGF, Class B) | |
| Epidermal growth factor receptor (EGFR, protein) | E07 aptamer (Class C) | Li et al., PloS ONE, 2011; 6(6): e20299 |
| Integrins (protein) | RGD-containing peptides (Class B) | |
| TNF-α (protein) | T09.12 peptide (Class C) | Xu et al., Chem Biol. 2002 August; 9(8): 933-42. |
| HaloTag (enzyme) | Halogenated compounds (Class D) | Bioconjug Chem. 2015 Jun. 17; 26(6): 975-86. |
| Oxidosqualene cyclase (OSC, enzyme) | [3H]29-methylidene-2,3-oxidosqualene ([3H]29-MOS, Class D) | Biochem Biophys Res Commun. 1992 Aug. 31; 187(1): 32-8. |

Table 4 provides a listing of additional targets. Antibodies and other known binding partners of these targets may be used as target recognizing moieties.

TABLE 4

Additional Representative Targets

Actin
AIF
AKT
alpha-synuclein
amyloid precursor protein
annexin
arrestin
BAD
BAX
Bcl-2
Bcl-2
beta-catenin
BRCA1
cAMP
caveolin
CD20
CD3
CD4
CD45
CD68
CD8
collagen
CREB
DNA
E-Cadherin
EGFR
EpCAM
ER
ERK
ERK
FOXA
FOXP3

TABLE 4-continued

Additional Representative Targets

GABA
GAPDH
GFP
granzymeB
GRB2
HER2
HER3
HIF-1
histoneH3
H5P27
HSP70
HSP90
keratin
Ki67
lamin
MAPK
MEK
MET
MMP
mTOR
MYC
NeuN
p21
p53
PAX
PD-1
PD-L1
PI3K
PR
PSD95
RAS
SOX
STAT
synapsin
Tau
TOM20
tubulin
ubiquitin
VEGF
vimentin
WNT B. Docking Strands In some embodiments, the docking moiety or docking strand is a nucleic acid, a protein, a peptide, or a chemical compound. Many proteins and domains of proteins are known to interact with other proteins, domains or peptides. Some of the best-known domains include SH2, SH3, and WD40 domains. In many cases the binding partner of these proteins and domains are known and can be engineered to have the desired affinity. For example, biotin and avidin/streptavidin interact with sufficient specificity. Many other chemical compounds, such as digoxigenin, fluorescein, tacrolimus and rapamycin also have well known binding partners.

In some embodiments, the docking strand comprises nucleic acids. In some embodiments, the nucleic acids are single stranded nucleic acids such as single stranded DNA, RNA, or a nucleic acid analog. A nucleic acid analog (also known as non-natural nucleic acid) may include an altered phosphate backbone, an altered pentose sugar, and/or altered nucleobases. Nucleic acid analogs may include, but are not limited to, 2'-O-Methyl ribonucleic acid, 2'-fluoro ribonucleic acid, peptide nucleic acid, morpholino and locked nucleic acid, glycol nucleic acid, and threose nucleic acid.

In some embodiments, the docking strand is attached to the imager strand covalently and in other embodiments noncovalently.

In some embodiments, the docking strand comprises single-stranded nucleic acids and may be from about 5 to 20 nucleotides long, from about 8 to 15, or from about 10 to 12 nucleotides long. In some embodiments, the docking strand is about 5, 8, 9, 10, 11, 12, 13, 14, 15, 18, or 20 nucleotides long.

The docking strand may be an independent element or it may be part of the target recognizing moiety. For example, if the target recognizing moiety is an antibody, part of the Fc domain of the antibody may be the docking strand and a peptide or protein that binds the Fc domain may be used, such as protein A or protein G.

The docking strand may be provided in a liquid medium or buffer solution.

C. Imager Strands

In some embodiments, the docking strand may be a nucleic acid strand. In such cases, the observable moiety or label may be conjugated to an imager moiety, which may be a nucleic acid strand that is complementary to the docking strand. In other words, the imager strand specifically binds the docking strand. In such a case, the label may be conjugated to an imager moiety that may be from about 5 to 20 nucleotides long, from about 8 to 15, or from about 10 to 12 nucleotides long. In some embodiments, the imager moiety is about 5, 8, 9, 10, 11, 12, 13, 14, 15, 18, or 20 nucleotides long.

In some embodiments, the imager strand is even longer, such as from 20 to 80 nucleotides long, for example less than or equal to 80, 75, 70, 65, 60, 55, 50, 45, 40, 35, or 30 nucleotides long. In embodiments employing a hairpin structure for the imager strand, the length of the imager strand may be longer than if no hairpin structure is used.

In some embodiments, the complementary portions between the imager moiety and the docking strand may be from about 5 to 20 nucleotides long, from about 8 to 15, or from about 10 to 12 nucleotides long. In some embodiments, the complementary portions between the imager moiety and the docking strand may be about 5, 8, 9, 10, 11, 12, 13, 14, 15, 18, or 20 nucleotides long.

In some embodiments, the nucleic acid imager strand comprises single stranded nucleic acids such as single stranded DNA, RNA, or a nucleic acid analog. A nucleic acid analog (also known as non-natural nucleic acid) may include an altered phosphate backbone, an altered pentose sugar, and/or altered nucleobases. Nucleic acid analogs may include, but are not limited to, 2'-O-Methyl ribonucleic acid, 2'-fluoro ribonucleic acid, peptide nucleic acid, morpholino and locked nucleic acid, glycol nucleic acid, and threose nucleic acid.

In some embodiments, the imager moiety is a protein, peptide, or a chemical compound, as a partner to the docking strand options discussed above in Section II.B above.

In some embodiments, the docking strand may bind to the imager moiety indirectly, such as through an intermediate moiety. For instance, when the docking strand and the imager moiety are nucleic acids, an intermediate moiety comprising nucleic acids may be used as long as the intermediate moiety has a first region complementary to the docking strand and a second region complementary to the imager moiety. In this embodiment, it is not necessary for the docking strand to be complementary to the imager moiety. The intermediate moiety may serve only a bridging function or it may also serve an amplification function.

The imager strand may be provided in a liquid medium or buffer solution.

D. Primer Strands

In some instances, the target-specific binding partner is linked indirectly to a docking strand, such as through a primer. For instance, when the docking moiety and the imager moiety comprise nucleic acids, the primer strand comprising nucleic acids may be used as a binding location for the docking strand (if the docking strand has a region complementary to the primer strand) or it may be used as a primer for nucleic acid synthesis through, for example, rolling circle amplification. The primer strand may also be used to initiate the cascade of binding events in hybridization chain reaction amplification. In instances where the primer serves as a location for amplification (such as rolling circle amplification, hybridization chain reaction amplification), the primer is not necessarily complementary to the docking strand. Instead, it serves as a template for amplification and the docking strands are included through the amplification process.

In some embodiments, the target-specific binding partner and linked primer are added to the sample as a first step, docking strand added as a second step, and imager strand added as a third step. In another embodiment, the components are not added in discrete steps. Washing steps may be added between the first, second, and/or third steps.

In some embodiments, the primer strand comprises nucleic acids. In some embodiments, the nucleic acids are single stranded nucleic acids such as single stranded DNA, RNA, or a nucleic acid analog. A nucleic acid analog (also known as non-natural nucleic acid) may include an altered phosphate backbone, an altered pentose sugar, and/or altered nucleobases. Nucleic acid analogs may include, but are not limited to, 2'-O-Methyl ribonucleic acid, 2'-fluoro ribonucleic acid, peptide nucleic acid, morpholino and locked nucleic acid, glycol nucleic acid, and threose nucleic acid.

In some embodiments, the primer strand comprises single-stranded nucleic acids and may be from about 5 to 20 nucleotides long, from about 8 to 15, or from about 10 to 12 nucleotides long. In some embodiments, the primer strand is about 5, 8, 9, 10, 11, 12, 13, 14, 15, 18, 20, 25, 30, 35, 40, 45, 50, 55, 60, 65, or 70 nucleotides long.

The primer strand may be provided in a liquid medium or buffer solution.

E. Intermediate Strands

In some instances, the docking strand binds to the imager strand through an intermediate moiety (or intermediate strand). For instance, when the docking moiety and the imager moiety comprise nucleic acids, the intermediate strand comprising nucleic acids may be used as long as the intermediate strand has a first region complementary to the docking strand and a second region complementary to the imager strand. In such embodiments, it is not necessary for the docking strand to be complementary to the imager moiety.

In some embodiments, the intermediate strand is added as a first step to a sample comprising the target-specific binding partner linked to a docking strand, either directly or indirectly, and the imager strands added as a second step. In another embodiment, the intermediate strand and imager strand are not added in discrete steps. In some instances, the intermediate strand and imager strand are hybridized together before being added in a single step.

In some embodiments, the intermediate strand comprises nucleic acids. In some embodiments, the nucleic acids are single stranded nucleic acids such as single stranded DNA, RNA, or a nucleic acid analog. A nucleic acid analog (also known as non-natural nucleic acid) may include an altered phosphate backbone, an altered pentose sugar, and/or altered nucleobases. Nucleic acid analogs may include, but are not limited to, 2'-O-Methyl ribonucleic acid, 2'-fluoro ribonucleic acid, peptide nucleic acid, morpholino and locked nucleic acid, glycol nucleic acid, and threose nucleic acid.

In some embodiments, the intermediate strand comprises single-stranded nucleic acids and may be from about 5 to 30 nucleotides long, from about 8 to 15, or from about 10 to 12 nucleotides long. In some embodiments, the intermediate strand is about 5, 8, 9, 10, 11, 12, 13, 14, 15, 18, 20, 25, or 30 nucleotides long.

The intermediate strand may be provided in a liquid medium or buffer solution.

F. Nucleic Acids in Hairpin Format

Any of the linear nucleic acids described herein may optionally be provided in a hairpin format. This includes the imager strand, docking strand, primer strand, and intermediate strand. In the hairpin format, a region of from at least 1-5 nucleotides at the end of the hairpin stem region may optionally comprise only G's and C's. This G/C region is known as a clamp. The G/C region prevents or reduces fraying at the end of the hairpin to prevent opening up into linear DNA.

A hairpin may be used in contexts when a user desires to break the interaction (direct or indirect) between the imager strand and the docking strand using a polymerase with a strand-displacement activity (e.g., phi29) or a polymerase with a 5'-to-3' exonuclease activity (e.g., DNA Polymerase I). A hairpin may also be used to limit unwanted binding of single-stranded nucleic acids.

G. Labels

Various labels, also known as observable moieties, may be bound to the imager strand. These labels or observable moieties assist the user by enabling detection of the bound imager strand. When the application refers to detecting bound labeled imager strands, the application references detecting the signal produced by the label or observable moiety bound to the imager strand.

In some embodiments, any observable moiety may be employed and, in some embodiments, the moiety is optically observable. The moiety may be signal absorbing or signal emitting. Of signal emitting molecules, molecules that fluoresce may be used, such as organic small molecules, including, but not limited to fluorophores, such as, but not limited to, fluorescein, Rhodamine, cyanine dyes, Alexa dyes, DyLight dyes, Atto dyes, etc.

In some embodiments, organic polymers, such as p-dots may be employed. In some embodiments, the observable moiety may be a biological molecule, including but not limited to a fluorescent protein or fluorescent nucleic acid (including fluorescent RNAs including Spinach and its derivatives). In some embodiments, the observable moiety may be an inorganic moiety including Q-dots. In some embodiments, the observable moiety may be a moiety that operates through scattering, either elastic or inelastic scattering, such as nanoparticles and Surface Enhanced Raman Spectroscopy (SERS) reporters (e.g., 4-Mercaptobenzoic acid, 2,7-mercapto-4-methylcoumarin). In some embodiments, the observable moiety may be chemiluminescence/electrochemiluminescence emitters such as ruthenium complexes and luciferases. The observable moiety may generate an optical signal, an electromagnetic signal (across the entire electromagnetic spectrum), atomic/molecular mass (e.g. detectable by mass spectrometry), tangible mass (e.g., detectable by atomic force microscope), current or voltage.

EXAMPLES

Example 1: Multiple Modes of Amplification

There are multiple approaches to amplification. This example demonstrates the use of three approaches including enzymatic amplification using HRP conjugates (FIG. 7A-C), rolling circle amplification (FIG. 7D-E), and hybridization chain reaction (HCR) (FIG. 7F-G).

For HRP-based amplification, formalin-fixed paraffin-embedded (FFPE) tonsil tissue sections were dewaxed and antigen-retrieved using R-Buffer A (Fisher Scientific) in a Lab Vision PT-module. Tissue sections were blocked in 3% BSA and 0.2% Triton-X 100 for 1.5 hours. Tissue sections were stained with a mouse anti-cytokeratin primary antibody overnight at 4° C. in a humidity chamber. Tissue sections were then washed with 1×PBS, and stained for 2 hours at room temperature with a goat anti-mouse secondary antibody conjugated to a DNA docking strand (D1). Tissue sections were washed again in 1×PBS, and stained for DAPI.

A fluorescence microscope was used to image the tissue section in the DAPI and Cy5 channels to serve as a blank. An imager strand (I1-650), comprising a red fluorophore attached to DNA that includes a domain complementary to a docking strand D1, was added to the prepared tissue section and allowed to hybridize for 25 minutes at room temperature. Sections were washed to remove unbound I1-650. Then, fluorescence images were captured in the DAPI and Cy5 channels using a 10× objective. See FIG. 7B.

The imager strand I1-650 was then removed by applying 10 units of USER enzyme to the tissue sections for 15 minutes at room temperature, washing with 1×PBS, incubating the tissue sample with 30% formamide for 5 minutes, then washing with 1×PBS. A fluorescence microscope was used to confirm the complete removal of fluorescent signal in the Cy5 channel. Then a brightfield image was taken at 10× magnification as a blank.

To amplify the cytokeratin signal for brightfield immunohistochemical detection, the tissue section was incubated with an imager strand (I1-HRP), comprising a horseradish peroxidase (HRP) enzyme attached to DNA that includes a domain complementary to docking strand D1. The sample was washed by submerging the tissue section in 1×PBS. Then, chromogenic signal amplification was carried out by applying a solution of 3,3'-diaminobenzidine (DAB) chromogen to the sample for 10 minutes. The sample was washed in 1×PBS. Finally, the sample was imaged using brightfield illumination. FIG. 7C.

Figure 7A:
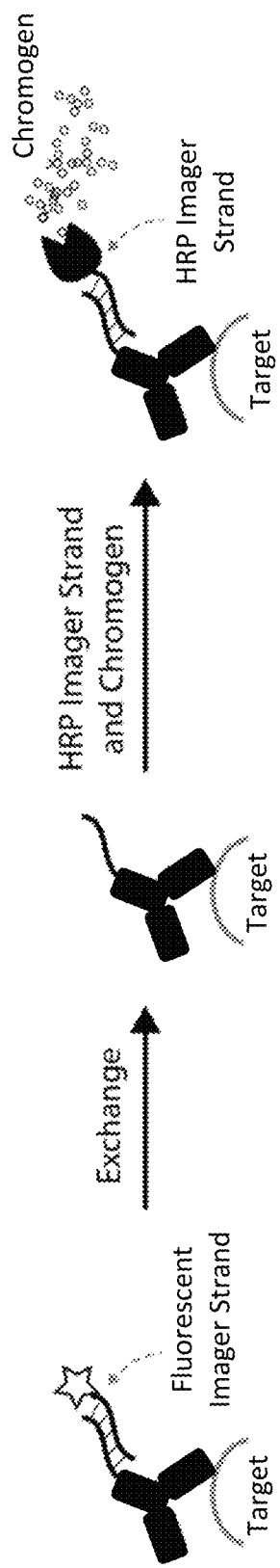
FIGS. 7A-G provide images after amplification.
Figure 7C:
Figure 7B:
Figure 7B:
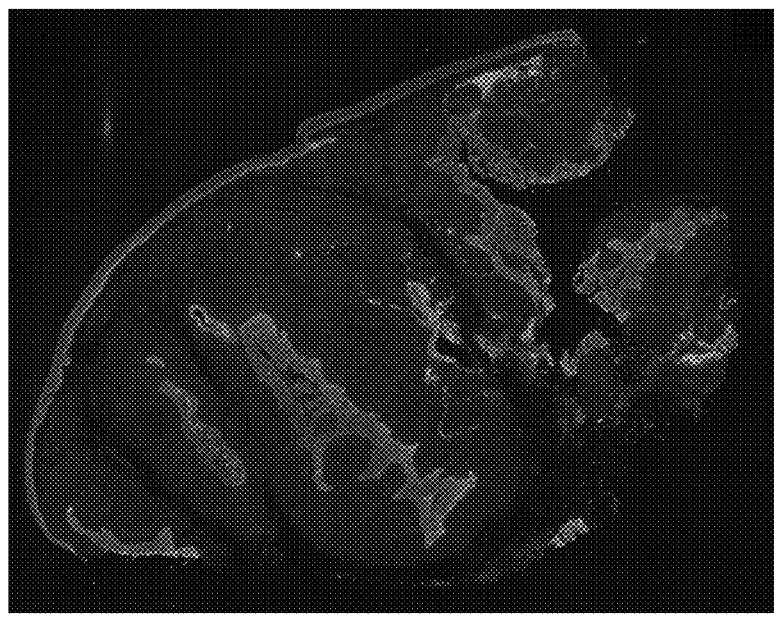

FIG. 7A-C illustrate the use of DNA Exchange to enable fluorescence and brightfield (e g immunohistochemistry) images to be captured on the same sample. While this example demonstrates the use of HRP-conjugated imager strands for chromogenic signal amplification, HRP-conjugated imager strands could also be applied for fluorescent signal amplification using alternative enzyme substrates (e.g. tyramide).

In a separate approach for amplification based on rolling circle amplification, cultured HeLa cells were fixed with warm 3% paraformaldehyde and 0.1% glutaraldehyde, reduced with 0.1% sodium borohydride, blocked and permeabilized with 3% bovine serum albumin and 0.2% Triton-X 100, and then stained with a rabbit primary antibody against vimentin overnight.

Figure 7D:
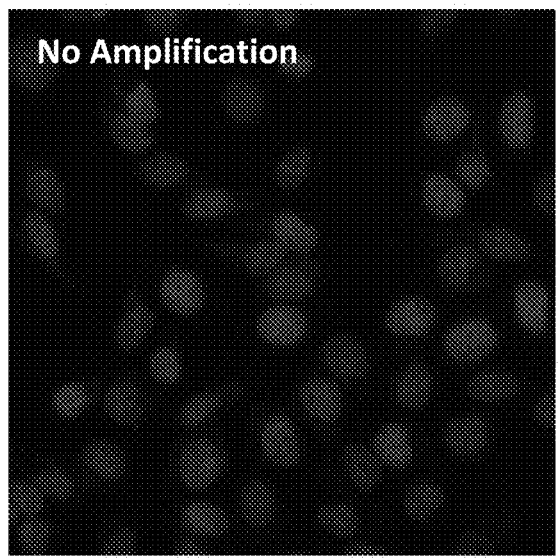
Figure 7E:
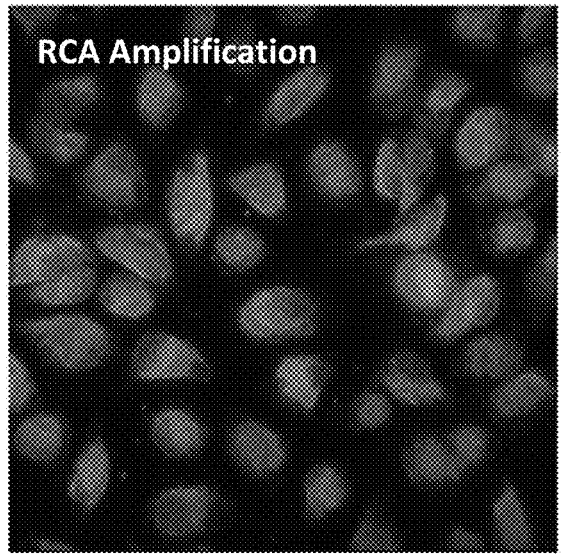
Figure 7F:
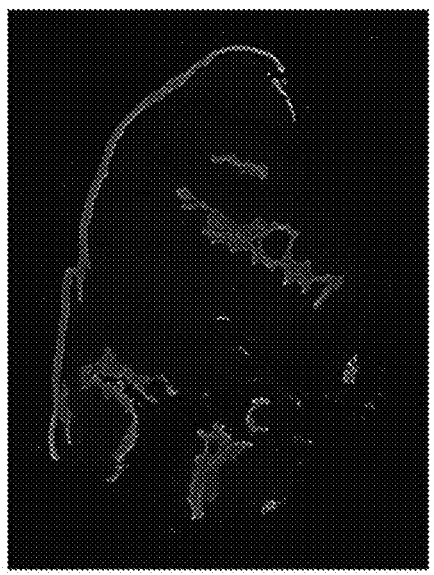
Figure 7G:
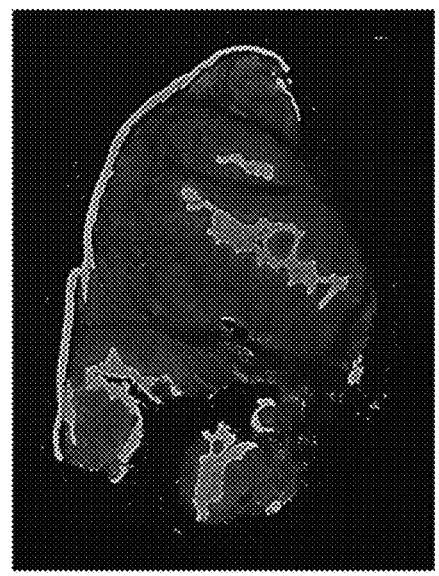

For a control sample, a goat-anti-rabbit antibody conjugated to a docking strand (Gt-a-Rb-D1) was incubated with the cells for 2 hours at room temperature as a secondary staining step. After washing the control sample, DAPI and 100 nM fluorescently labeled imager strands were added to the sample. Fluorescence images in the DAPI and Cy5 channels were collected of the control well. FIG. 7D.

The following procedure was carried out for cell samples undergoing rolling circle amplification. A goat-anti-rabbit antibody conjugated to a docking strand (Gt-a-Rb-D1), was used as a template for ligation. A ligation solution was made in a PCR tube with 125 nM circle oligo (IDT DNA), 125 nM Gt-a-Rb-D1, 20 U/µL T4 ligase (NEB), in 1× ligation buffer (NEB). The ligation solution was incubated at room temperature for two hours. After ligation, the ligation solution was diluted 1:5 in blocking buffer, added to the cell samples, and allowed to incubate for 2 hours at room temperature, then washed in 1×PBS.

In a separate vessel, a polymerase solution was made containing 0.1 mg/mL BSA, 0.2 mM dNTPs, and 1 U/µL phi29 DNA Polymerase in 1× polymerase reaction buffer (New England Biolabs). The polymerase solution was applied directly the cell samples that were prepared for RCA. The samples were incubated with the polymerase solution for 1.5 hours at 30° C. The cell samples were washed three times with 1×PBS. DAPI was added to stain the cell nuclei. Finally, 100 nM fluorescently labeled imager strands were added prior to imaging. Fluorescence images in the DAPI and Cy5 channels were collected following RCA. See FIG. 7E.

In a separate approach for amplification based on a hybridization chain reaction, formalin-fixed paraffin-embedded (FFPE) tonsil tissue sections were dewaxed and antigen-retrieved using R-Buffer A (Fisher Scientific) in a Lab Vision PT-module. Tissue sections were blocked in 3% BSA and 0.2% Triton-X 100 for 1.5 hours. Tissue sections were stained with a mouse anti-cytokeratin primary antibody overnight at 4° C. in a humidity chamber. Tissue sections were then washed with 1×PBS, and stained for 2 hours at room temperature with a goat anti-mouse secondary antibody conjugated to a DNA docking strand (D1). Tissue sections were washed again in 1×PBS, and stained for DAPI.

A fluorescence microscope was used to image the tissue section in the DAPI and Cy5 channels to serve as a blank. An imager strand (I1-650), comprising a red fluorophore attached to DNA that includes a domain complementary to a docking strand D1, was added to the prepared tissue section and allowed to hybridize for 25 minutes at room temperature. Sections were washed to remove unbound I1-650. Then, fluorescence images were captured in the DAPI and Cy5 channels using a 10× objective. See FIG. 7F.

The imager strand I1-650 was then removed by applying 10 units of USER enzyme to the tissue sections for 15 minutes at room temperature, washing with 1×PBS. A fluorescence microscope was used to confirm the complete removal of fluorescent signal in the Cy5 channel (data not shown).

After removal of the imager strand, a primer strand including the I1 sequence was hybridized to the D1 docking strand (20 nM) for 30 minutes at room temperature. The sections were washed with 1×PBS to wash the unbound primer strands. In parallel, hairpin strands H1 and H2-D2 were diluted to 1 uM in 5×SSX in separate microcentrifuge tubes. The tubes were heated and held at 90° C. for 5 minutes, and then slowly cooled down to room temperature. The hairpins were then pooled and diluted to 200 nM in 5×SSC with 0.1% Tween 20 and 10% dextran sulfate. This solution was added to the tissue section and incubated overnight in an incubation chamber at room temperature. The sections were then washed with PBS 1× Finally, 100 nM fluorescently labeled imager strands I2 were added prior to imaging. Fluorescence images in the DAPI and Cy5 channels were collected following HCR amplification. FIG. 7G, right.

Example 2: Amplification with Pre-Ligated Circle Oligo

Figure 8:
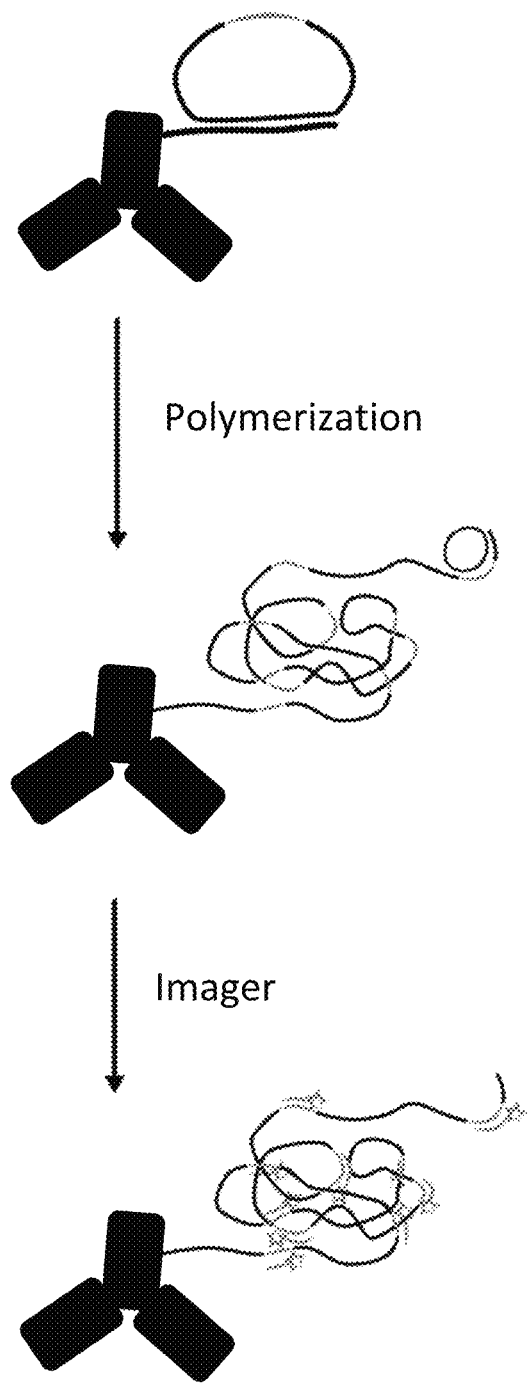
FIG. 8 shows the use of pre-formed nonlinear DNA strands that can be hybridized to docking strands as a starting point for rolling circle polymerization.

Nonlinear DNA strands were made in advance of performing an assay. Using nonlinear DNA strands provides the benefit that it may increase the efficiency of signal amplification, particularly if the signal amplification method used is similar to rolling circle amplification (FIG. 8). In this example, a circular DNA strand was made via a ligation step. The DNA sequence used in the ligation step was referred to as the circle oligo, which includes a domain that is equivalent to an imager strand sequence (i.e. complementary to a docking strand).

Cultured HeLa cells were fixed with warm 3% paraformaldehyde and 0.1% glutaraldehyde, reduced with 0.1% sodium borohydride, blocked and permeabilized with 3% bovine serum albumin and 0.2% Triton-X 100, and then stained with a rabbit primary antibody against vimentin overnight. A goat-anti-rabbit antibody conjugated to a docking strand (Gt-a-Rb-D1), was then used as a secondary stain and allowed to incubate for 2 hours at room temperature.

A ligation solution was made in a PCR tube with 0.5 µM circle oligo (IDT DNA), 50 µM ATP, 2.5 mM $MnCl_2$, 5 U/µL CircLigase (Cat #CL4111K, EpiCentre), in 1× reaction buffer (EpiCentre). The ligation solution was placed in a thermocycler for 1 hour to incubate at 60° C. After ligation, a 1:4 dilution of the ligation solution was made in blocking buffer, added to the stained cell samples, and allowed to incubate for 25 minutes to hybridize to a docking strand on an antibody-labeled target complex before washing in PBS.

As an alternative approach, the ligation step can be carried out prior to staining the sample with a secondary antibody conjugate. Following the ligation step, an excess of ligation solution was hybridized to an antibody DNA conjugate such that the molar ratio of ligated circle oligo was at least two-fold greater than the molar ratio of docking strands bound to the antibody. After hybridization of the ligated circle oligo to Gt-a-Rb-D1, the complex was added to the sample and incubated for two hours at room temperature as a secondary staining step, then washed three times in 1×PBS.

In a separate vessel, a polymerase solution was made containing 0.1 mg/mL BSA, 0.2 mM dNTPs, and 1 U/µL phi29 DNA Polymerase in 1× polymerase reaction buffer (New England Biolabs). The polymerase solution was applied directly to a fixed cell sample that was already stained with a primary antibody, a secondary antibody docking strand conjugate, and hybridized to a ligated circle oligo. The sample was incubated with the polymerase solution for 1.5 hours at 30° C. The cell samples were washed three times with 1×PBS. DAPI was added to stain the cell nuclei. Finally, 100 nM fluorescently labeled imager strands were added prior to imaging. FIG. 8 shows the use of pre-formed nonlinear DNA strands that can be hybridized to docking strands as a starting point for rolling circle polymerization.

Example 3: Sample Re-Interrogation (0-A-0-A)

This example demonstrates the ability to use Exchange Imaging to reinterrogate a target in a sample. It also shows that the enzymatic method of extinguishing signal does not affect, modify, or degrade the staining of the sample.

In this example, docking strands (D1 and D2) were conjugated to secondary antibodies goat anti-mouse and goat anti-rabbit respectively. The imagers strands I1U and I2U, respectively complementary to D1 and D2, were labeled with a fluorescent dye (ATTO647N). The sequence of the imager strands I1U and I2U includes several uracil nucleobases. An enzyme, or cocktail of enzymes, can cleave bases leading to the dehybridization of the docking-imager duplex, leading to a decrease in the observed signal.

Cultured HeLa cells were fixed with warm 3% paraformaldehyde and 0.1% glutaraldehyde, reduced with 0.1% sodium borohydride, blocked and permeabilized with 3% bovine serum albumin and 0.2% Triton-X 100 in 1×PBS for 1.5 hours. The cells were first stained using a cocktail of primary antibodies anti-tubulin and anti-TOM20, raised in mouse and rabbit respectively, overnight at 4° C. Goat secondary antibodies against mouse and rabbit conjugated to two different docking strands (Gt-a-Ms-D1 and Gt-a-Rb-D2) were used for a secondary staining for 2 hours at room temperature. DAPI was added to stain the cell nuclei.

Samples were loaded onto an inverted Nikon Eclipse Ti microscope (Nikon Instruments) with a fluorescence module and an Andor Zyla sCMOS camera. The microscope was equipped with two fluorescence filter sets to image DAPI and the fluorescently labeled imager strands (Cy5 channel).

Figures 9A, 9B, 9C, 9D, 9E, 9F:
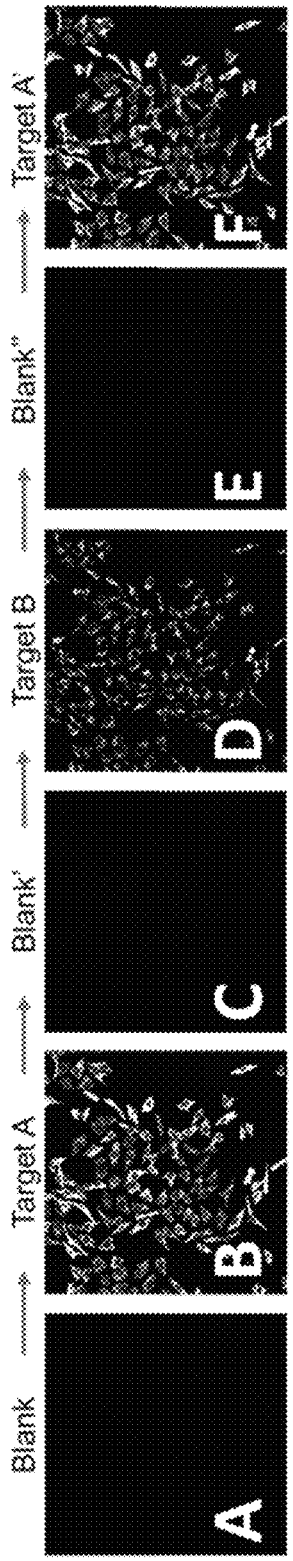
FIGS. 9A-F and 9H-K show a series of images obtained in the Cy5 channel during an exchange imaging experiment to reinterrogate a target in a sample.
Figure 9G:
FIG. 9G shows the average signal intensity in the images of FIGS. 9A-F.

The sample was first imaged using a 20× dry objective (Nikon, 0.45 NA), in both DAPI and Cy5 channels to register the cells using DAPI, and to measure the autofluorescence signal in the Cy5 channel (FIG. 9A). A solution of 100 nM I1U was added to the sample and incubated for 15 minutes. The sample was then washed 3 times with 1×PBS, and imaged again (FIG. 9B). To extinguish the signal, a solution containing 5 units of USER™, 50 mM potassium acetate, 20 mM tris-acetate, 10 mM magnesium acetate, and 100 µg/ml BSA, was added to the sample, and incubated at room temperature for 15 minutes. The sample was then washed 3 times with PBS 1×, and imaged (FIG. 9C). A solution of 100 nM I2U was added to the sample and incubated for 15 minutes. The sample was then washed 3 times with 1×PBS, and imaged (FIG. 9D). The signal was extinguished as previously, and the sample was imaged again (FIG. 9E). Finally, a solution of 100 nM I1U was added to the sample and incubated for 15 minutes. The sample was washed 3 times with 1×PBS, and imaged (FIG. 9F).

FIG. 9 shows the series of images obtained in the Cy5 channel during this experiment. In FIGS. 9A, 8C, and 8E, no signal is observed. These images correspond to: before introduction of imager strand, after removal of I1U, and after removal of I2U respectively. After addition of the imager strand I1U, the microtubule networked is observed (FIG. 8B, 8F). FIG. 8D shows the presence of mitochondria after adding I2U. FIG. 9G presents the average signal intensity in the images of FIGS. 9A-F. The signal decreases by more than 98% in both cases shown in FIGS. 9C and 8E. The signal recovery on the microtubule target after two rounds of exchange is over 95%, demonstrating the ability to reliably reinterrogate a target after multiple exchange steps.

The images in FIGS. 9A-F were obtained by manually pipetting the incubation and wash solutions in and out of the imaging chambers. The Exchange Imaging workflow can be automated by using flow cells and a fluidic system.

Using a fluidics system synchronized with the acquisition software of the microscope, the fluidics steps required for the hybridization of the imager strand (injections, incubation, washes), as well as the signal removal can be automatically performed between imaging rounds.

Figure 9K:
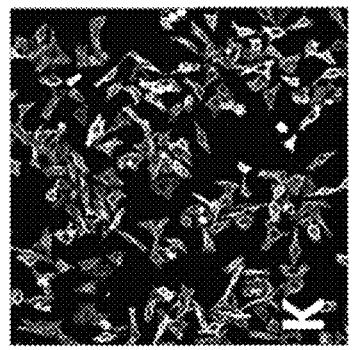
Figure 9J:
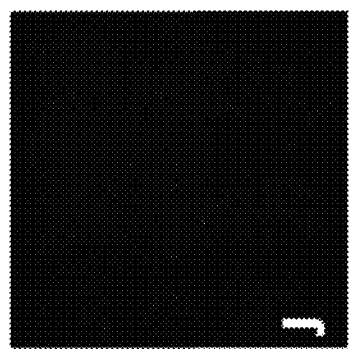
Figure 9I:
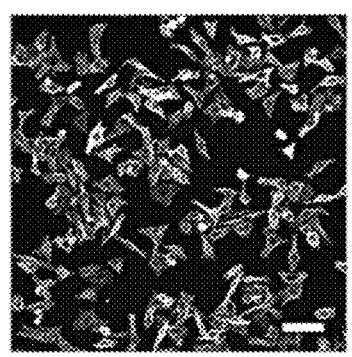
Figure 9H:
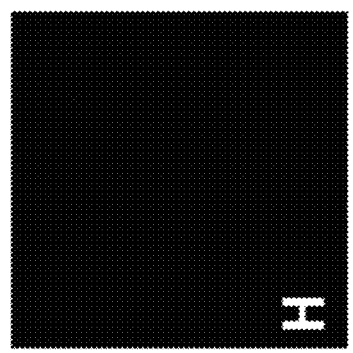

HeLa cells were cultured, fixed, and stained as described above, in a flow cell, which can be fitted on a regular microscope stage. The sample was first imaged using a 20× dry objective (Nikon, 0.45 NA), in both DAPI and Cy5 channels to register the cells using DAPI, and to measure the autofluorescence signal in the Cy5 channel (FIG. 9, Image H). A solution of 100 nM I1U was flowed into the sample chamber and incubated for 15 minutes. The sample was then washed with 1×PBS with continuous flow for 30 seconds, and imaged again (FIG. 9I). Next, a solution containing 5 units of USER™, 50 mM potassium acetate, 20 mM tris-acetate, 10 mM magnesium acetate, and 100 µg/ml BSA, was injected into the flow cell, and incubated for 15 minutes. The sample was then washed for 30 seconds with PBS 1×, and imaged (FIG. 9J) Finally, the solution of imager I1U was injected again into the flow cell, incubated for 15 minutes, washed with PBS for 30 seconds. The sample was imaged one last time (FIG. 9K).

Example 4: Proximity Detection with Stable Binding

A pair of proximity probes (PL and PR) were conjugated to anti-mouse antibodies using the ThunderLink kit (Innova Biosciences). Cultured HeLa cells were fixed with warm 3% paraformaldehyde and 0.1% glutaraldehyde, reduced with 0.1% sodium borohydride, blocked and permeabilized with 3% bovine serum albumin and 0.2% Triton-X 100, and then stained with a mouse primary antibody against alpha-tubulin. Fixed cells were then stained with a mixture of PL- and PR-conjugated secondary antibodies, and washed to remove any unbound material. A large fraction of anti-alpha-tubulin antibodies in the sample should receive at least one molecule of PL-conjugated secondary antibody and at least one molecule of PR-conjugated antibody. To detect proximity signal, DAPI and 100 nM of imager strand was added to the sample, and the sample was imaged with wide-field fluorescence microscope at 20×, with an LED light source (FIG. 10A (top panel)).

In a negative control experiment (FIG. 10, bottom panel), one of the proximity probes was conjugated to an off-target, anti-rabbit secondary antibody. Fixed cells were stained with mouse anti-tubulin primary, PL-conjugated anti-mouse and PR-conjugated anti-rabbit secondary antibodies. The anti-rabbit secondary antibody should not bind to the mouse derived primary, and thus the proximity probes should not be co-localized and the full docking site will not be available to bind the imager strand.

As shown in FIG. 10 the microtubule structures are apparent only when both proximity probes are specifically bound to the target. Fluorescence signal is stable for standard fluorescence imaging.

Example 5: Control Experiment for Off-Target Crossreactivity

Cross-reactivity between off-target imager and docking strands was assessed by measuring the signal intensity of a sample before and after exposure to noncomplementary imager strand sequences.

Cultured HeLa cells were fixed, reduced, blocked and permeabilized, then stained with a mouse primary antibody against alpha-tubulin. Fixation buffer was composed of 3% paraformaldehyde and 0.1% glutaraldehyde. A solution containing 0.1% sodium borohydride was used to reduce fixed cells. A solution with 3% bovine serum albumin and 0.2% Triton-X 100 was used to block and permeabilized cells for 1.5 hours, prior to overnight primary antibody staining. To test the crossreactivity of docking strand A to imager strands B and C, anti-mouse antibodies conjugated to docking strand A (a-Ms-$A_d$) were added to fixed cell samples stained for alpha-tubulin. Secondary staining with a-Ms-$A_d$ was done for 2 hours at room temperature in blocking buffer, then washed three times in 1×PBS. DAPI stain was added to all wells, and blank images were taken in both the DAPI and Cy5 channels on a Nikon fluorescence microscope with a 20× objective.

After recording blank images, imager strand solutions were prepared. In this example, an imager strand was partially double stranded; the imager strand was composed of a universal domain and a non-universal domain, where the universal domain is hybridized a complementary sequence that is attached to a fluorophore and the non-universal domain is single stranded and available to interact with a docking strand in a sample. In this example, a fluorophore is included in the imager strand indirectly, through a DNA-based bridge. In this example, the non-universal domain in an imager strand is complementary to a specific docking strand (ex. docking strand A, B, or C.)

A 100 nM solution of imager strands A ($A_i$), B ($B_i$), or C ($C_i$) was added to separate sample wells and allowed to hybridize for 10 minutes. Following hybridization of the imager strands, samples were washed with 1×PBS three times. Images were taken of each well in both the DAPI and Cy5 channels on a Nikon fluorescence microscope with a 20× objective. The same field of view was imaged as selected for the blank image previously.

The signal intensity of each sample was compared before and after addition of the imager strand using custom made software. Images were aligned using the DAPI channel, and a mask was made to segment individual cells from the background. The mean fluorescence intensity inside the cell region was calculated for the Cy5 channel and divided by the mean intensity of the background to yield a signal-to-noise ratio. The signal-to-noise ratios obtained in the blank image were compared to the signal-to-noise ratios obtained post-addition of imager strand to assess cross-reactivity between imager strands $A_i$, $B_i$, and $C_i$ with docking strand A.

Figures 11A, 11B, 11C:
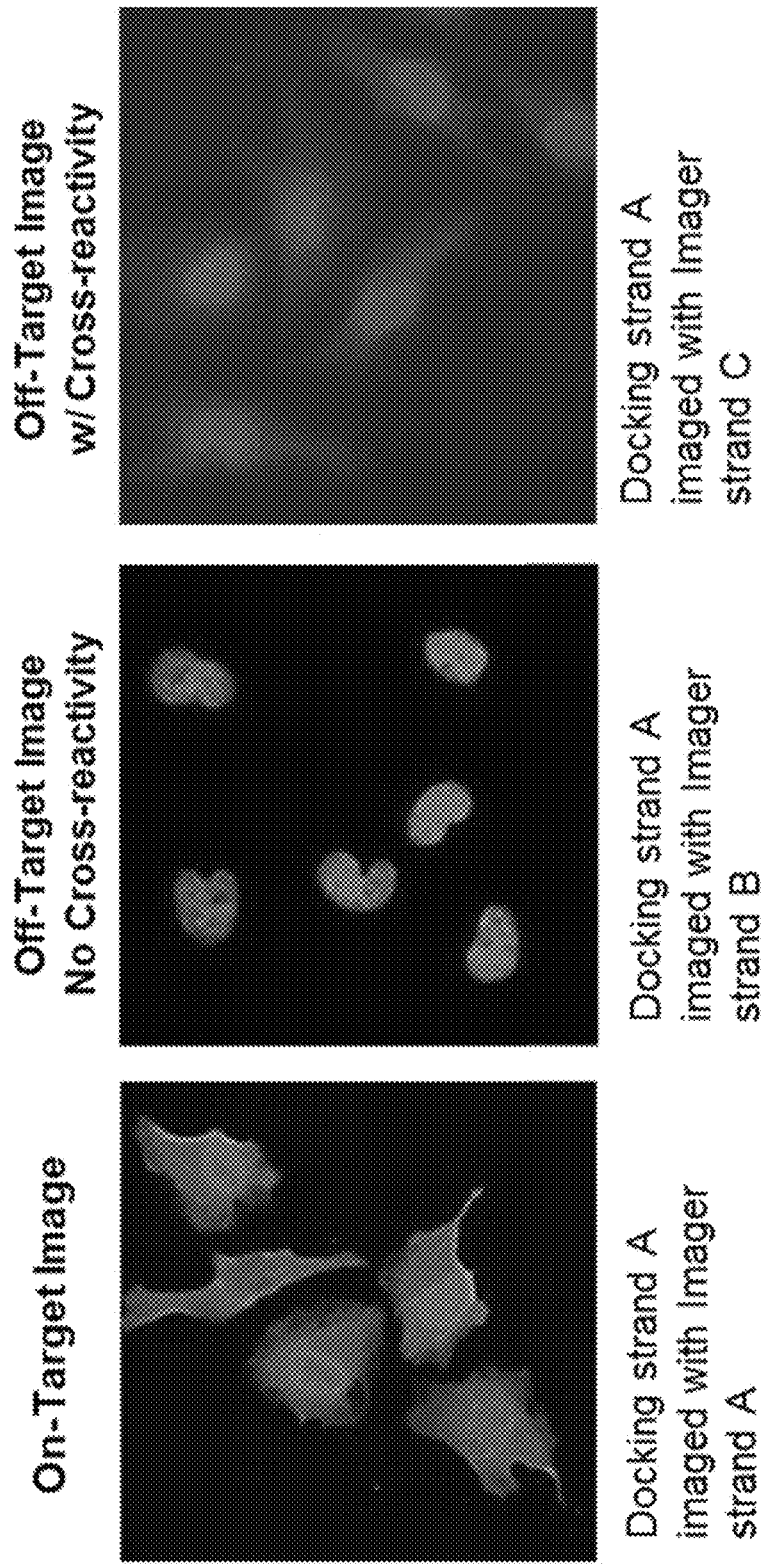
FIGS. 11A-C shows cell staining in an experiment designed to evaluate off-target cross reactivity. These figures also use DAPI staining of the nucleus inside of cells (blue). Alpha-tubulin staining (red) is strongly present in FIG. 11A, absent in FIG. 11B, and weakly present in FIG. 11C.
Figure 12A:
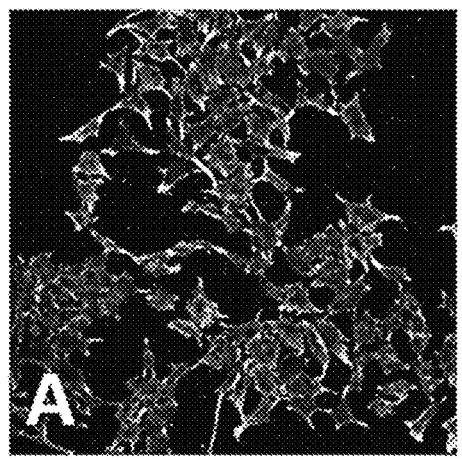
FIGS. 12A-D show that the signal from a target can be almost completely extinguished either using USER or UDG.
Figure 12B:
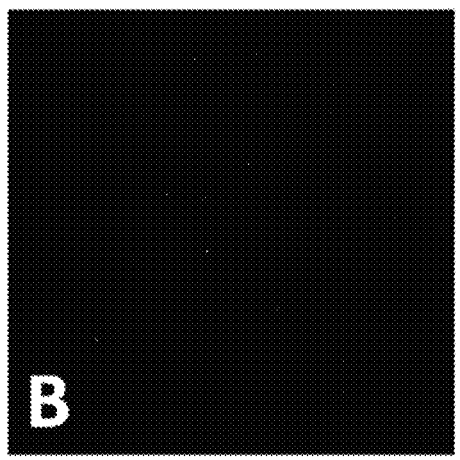
Figure 12C:
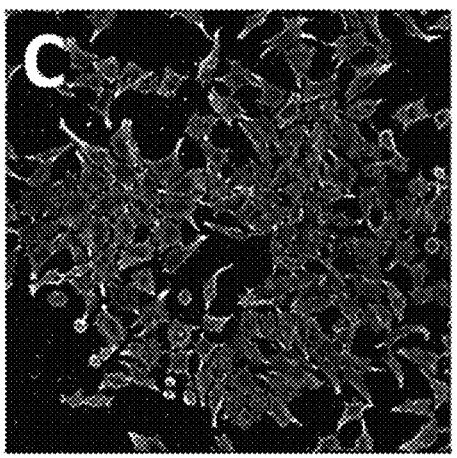
Figure 12D:
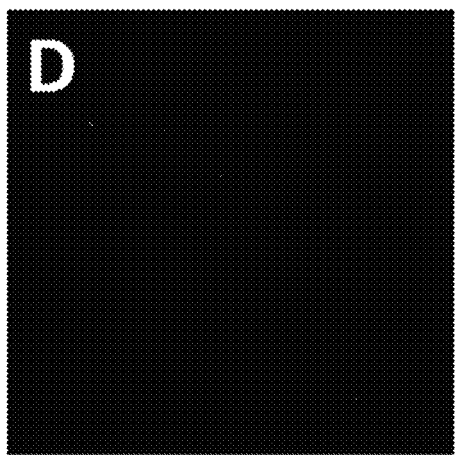
Figure 13A:
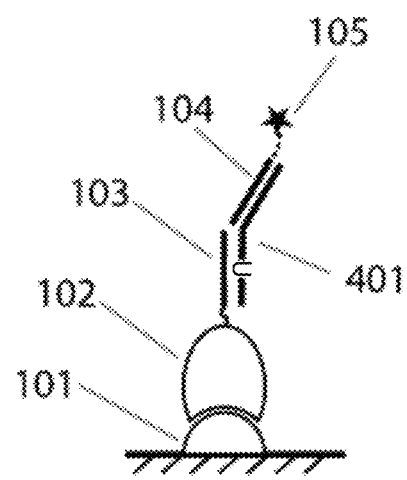
FIGS. 13A-D show various embodiments of exchange imaging, some using primer and intermediate strands in addition to imager and docking strands.
Figure 13B:
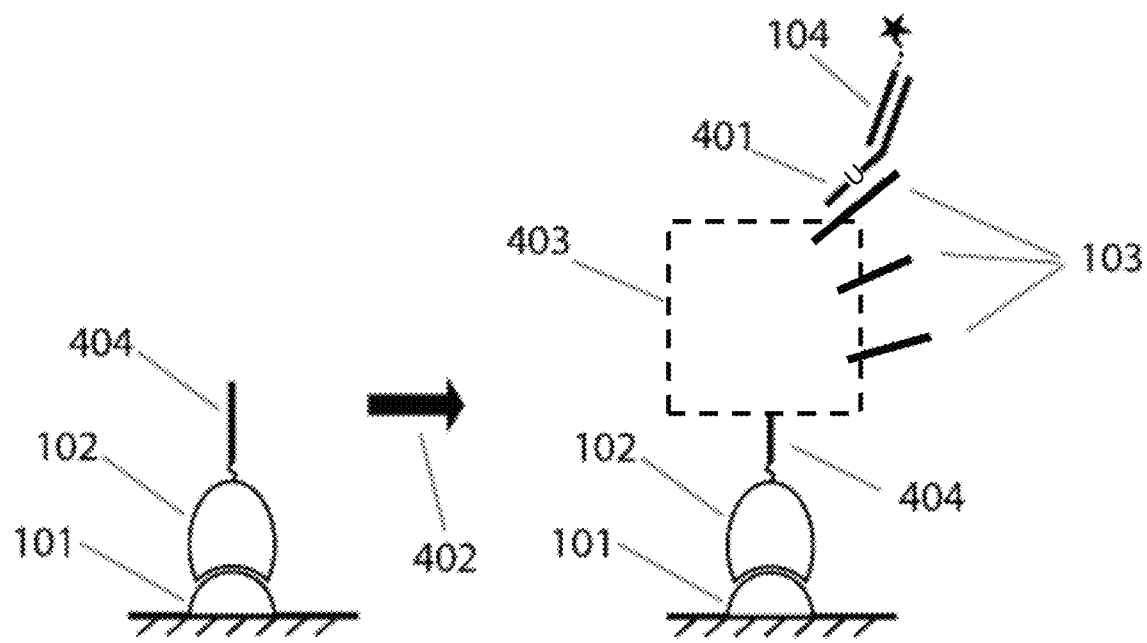
Figure 13C:
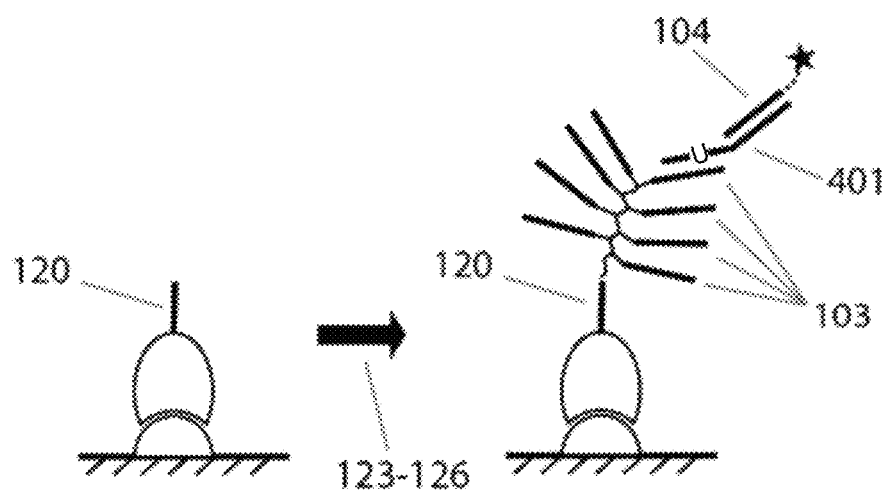
Figure 13D:
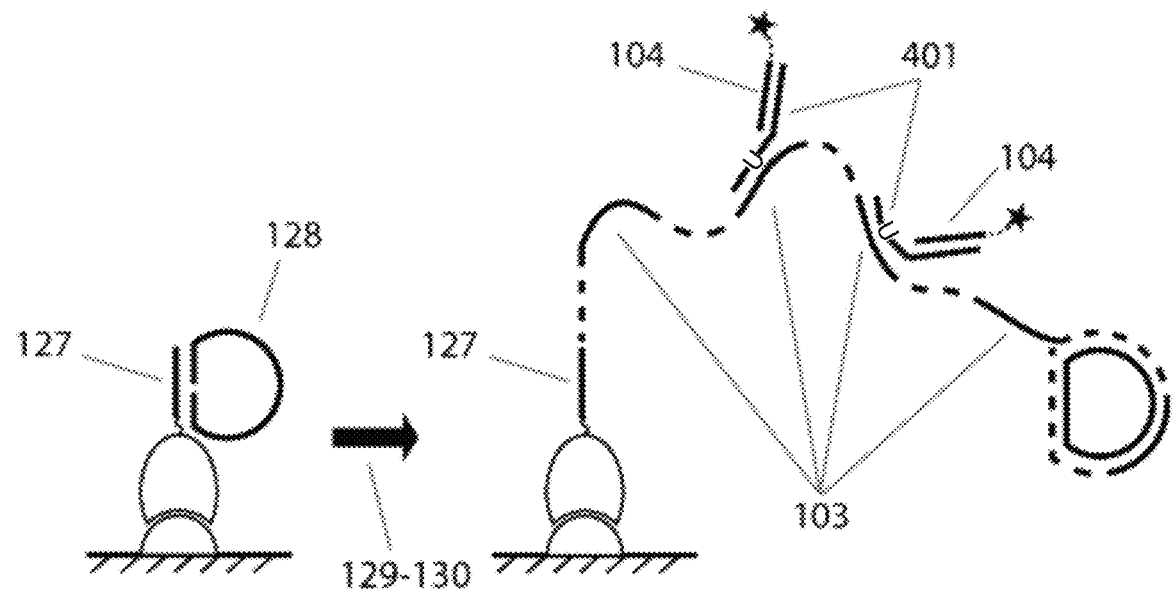
Figure 15A:
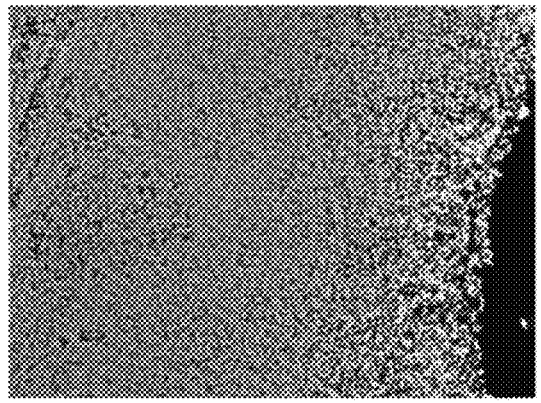
FIGS. 15A-F show an embodiment of exchange imaging in which four targets are imaged using four imager strands labeled with two different fluorophores, two targets at a time, sequentially. Thus.
Figure 15D:
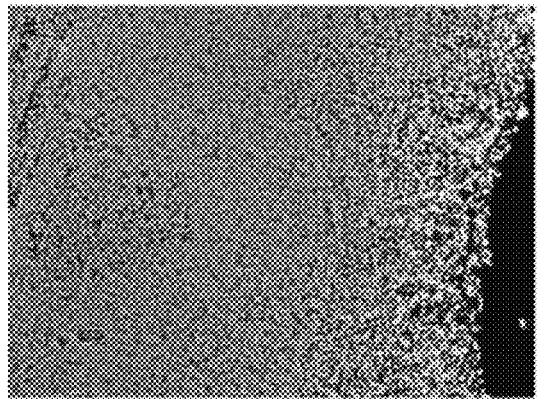
Figure 15B:
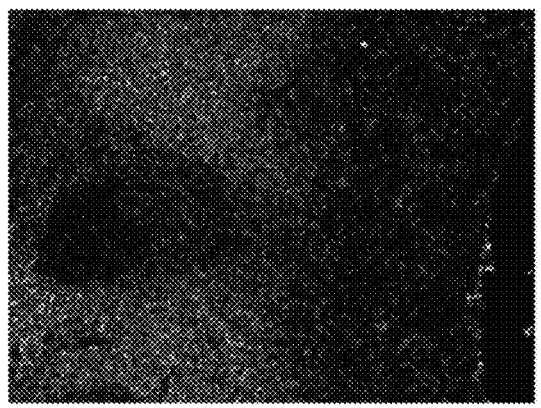
Figure 15E:
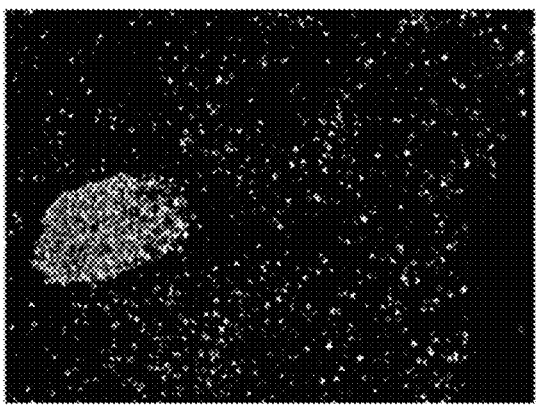
Figure 15C:
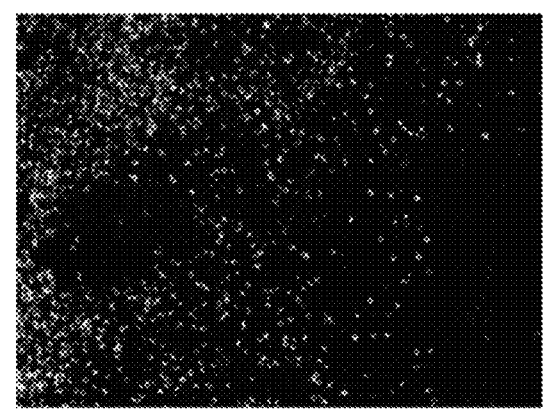
Figure 15F:
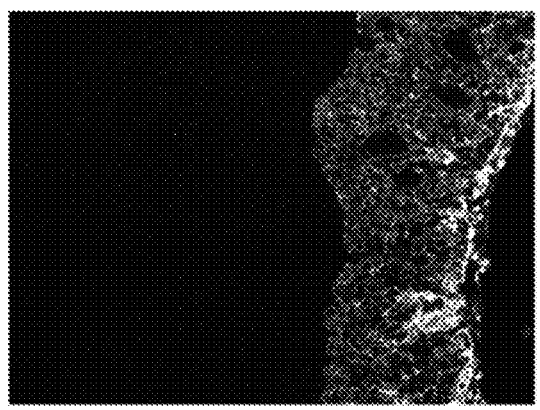

As shown in FIG. 11, the on-target imager strand Ai clearly shows the specific microtubule structures stained with a-Ms-$A_d$. FIG. 11 also shows that $B_i$ does not crossreact with docking strand A, but $C_i$ zdoes.

Example 6: USER and SubUSER

This example demonstrates the ability to extinguish signal from a target using enzymatic activity. In this example, the docking strand (D1) was conjugated to secondary antibodies goat anti-mouse. The imagers strands I1U complementary to D1, were labeled with a fluorescent dye (ATTO647N). The imager strand I1U contained several uracil nucleobases that can be cleaved by specific enzymatic activity, destabilizing the duplex imager/docking strands, resulting in the removal of fluorescent signal.

Cultured HeLa cells were fixed with warm 3% paraformaldehyde and 0.1% glutaraldehyde, reduced with 0.1% sodium borohydride, blocked and permeabilized with 3% bovine serum albumin and 0.2% Triton-X 100 in 1×PBS for 1.5 hours. The cells were first stained with a primary antibody anti-tubulin raised in mouse, overnight at 4° C. Secondary staining was performed using a goat secondary antibody against mouse conjugated to D1 for 2 hours at room temperature. DAPI was added to stain the cell nuclei.

Samples were loaded onto an inverted Nikon Eclipse Ti microscope (Nikon Instruments) with a fluorescence module and an Andor Zyla sCMOS camera. The microscope was equipped with two fluorescence filter sets to image DAPI and the fluorescently labeled imager strands (Cy5 channel).

A solution of 100 nM I1U was added to two separate samples and incubated for 15 minutes. The samples were then washed 3 times with 1×PBS, and imaged using a 20× dry objective (Nikon, 0.45 NA), in both DAPI and Cy5 channels (FIG. 12, Image A and C). To extinguish the signal, a solution containing 2 units of USER™, 50 mM potassium acetate, 20 mM tris-acetate, 10 mM magnesium acetate, and 100 µg/ml BSA, was added to one sample. To the other sample, a solution of 10 units Uracil-DNA Glycosylase (UDG) in 20 mM Tris-HCl, 1 mM DTT, 1 mM EDTA. Both samples were incubated at room temperature for 15 minutes. The samples were then washed 3 times with PBS 1×, and imaged (FIG. 12, Image B for USER and D for UDG).

As shown on FIG. 12, signal can be almost completely extinguished either using USER or UDG.

Example 7: Cleavage of Imager Strands by USER

As shown in FIG. 14, the extent that signal can be extinguished may depend on the imager strand architecture and/or sequence design. In this example, formalin-fixed paraffin embedded (FFPE) tissue samples were dewaxed, antigen retrieved, blocked, and stained with anti-CD3 antibodies conjugated to docking strand D1. The number of D1 docking strands bound to the sample were amplified by RCA and labeled with imager strands containing a domain complementary to D1 and linked to a fluorophore. Imager strands either contained several uracil nucleobases (FIGS. 14A and C) or several uracil nucleobases and an abasic site (FIGS. 14B and D). Images were collected using a fluorescence microscope to detect the presence of targets bound by labeled imager strands (FIG. 14A-B).

To extinguish the signal, a solution containing USER was added and incubated with the tissue sample for 15 minutes, followed by washing steps to remove the cleaved imager strands. Fluorescence images were collected to confirm the removal of the fluorescence signal. As shown in FIG. 14D, the presence of an abasic site in addition to dideoxyuridines in the imager strand sequence design results in improved removal efficiency compared with FIG. 14C.

Example 8: Combined Multicolor and Sequential Detection

This example illustrates the ability to use Exchange Imaging to detect multiple targets using sets of imager strands functionalized with different, spectrally separated fluorophores.

Formalin-fixed paraffin-embedded (FFPE) tonsil tissue samples were dewaxed, antigen retrieved, blocked, and stained with DAPI, as well as anti-CD4, anti-CD8, anti-Ki67, and anti-Cytokeratin antibodies respectively conjugated to docking strand D1, D2, D3, and D4. The number of docking strands (D1, D2, D3, D4) bound to the sample via the antibodies was amplified by RCA. Imager strands I1, I2, I3, and I4, containing a domain complementary to D1, D2, D3, and D4 respectively, also comprised several uracil bases for enzymatic removal. I1, and I3 are labeled with Atto565 dye, while I2 and I4 are labeled with Atto647N. Samples were imaged using an inverted Nikon Eclipse Ti microscope (Nikon Instruments) with a fluorescence module and an Andor Zyla sCMOS camera. The microscope was equipped with fluorescence filter sets to image DAPI and the fluorescently labeled imager strands (TRITC and Cy5 channels).

In a first step, the sample was labeled using I1 and I2 imager strands, by incubating a cocktail of the two strands on the sample for 25 minutes. The unbound strands were washed away, and images were collected in the TRITC and Cy5 channels to detect the presence of the targets labeled with the imager strands I1 and I2, respectively CD4 and CD8 (FIGS. 15 B and C respectively). A DAPI image was also collected to detect the cell nuclei (FIG. 15 A).

The signal was then extinguished, using a solution containing USER, which was incubated with the tissue sample for 15 minutes, followed by washing steps to remove the cleaved imager strands. Fluorescence images were collected to confirm the removal of the fluorescence signal.

Finally, the sample was labeled again using a cocktail solution of the imager strands I3 and I4, followed by a wash step to remove unbound imager strands. A fluorescence image was acquired in the TRITC and Cy5 channels to detect the presence of Ki67 and Cytokeratin (FIGS. 15 E and F respectively). A DAPI image was also collected (FIG. 15 D), and used to align and overlay the images of the four targets.

Example 9: Numbered Items

The following numbered items provide a further description of the embodiments herein and how they relate to each other.

Item 1. A method comprising
(1) contacting a sample being tested for the presence of one or more targets with one or more target-specific binding partners, wherein each target-specific binding partner is linked to a nucleic acid strand and wherein target-specific binding partners of different specificity are linked to different nucleic acid strands,
(2) optionally removing unbound target-specific binding partners,
(3) wherein the nucleic acid strand is a docking strand or a primer strand and if the nucleic acid is
    (a) a docking strand, increasing the number of docking strands associated with each target-specific binding partner, or
    (b) a primer strand, associating more than one docking strand with the primer strand,
(4) contacting the sample with labeled imager strands capable of binding a docking strand, directly or indirectly,
(5) optionally removing unbound labeled imager strands,
(6) imaging the sample to detect bound labeled imager strands,
(7) optionally removing the bound labeled imager strands from the docking strands, and
(8) optionally repeating steps (1)-(6), or any subset thereof.

Item 2. A method comprising
(1) contacting a sample being tested for the presence of one or more targets with one or more target-specific binding partners, wherein each target-specific binding partner is linked to a nucleic acid strand and wherein target-specific binding partners of different specificity are linked to different nucleic acid strands,
(2) optionally removing unbound target-specific binding partners,
(3) contacting the sample with labeled imager strands capable of binding a docking strand, directly or indirectly, wherein the nucleic acid strand in (1) is either a primer strand or a docking strand and if the nucleic acid strand is a primer strand, it is linked to a docking strand, (4) optionally removing unbound labeled imager strands,
(5) imaging the sample to detect bound labeled imager strands and determine if amplification (step (7)) is required,
(6) optionally removing the bound labeled imager strands from the docking strands,
(7) optionally increasing the number of docking strands associated with each target-specific binding partner, and
(8) optionally repeating steps (1)-(7), or any subset thereof.

Item 3. A method to test a sample for the presence of one or more targets comprising
(1) contacting a sample being tested for the presence of one or more targets with one or more target-specific binding partners, wherein each target-specific binding partner is linked to a nucleic acid strand and wherein target-specific binding partners of different specificity are linked to different nucleic acid strands,
(2) optionally removing unbound target-specific binding partners,
(3) contacting the sample with a nonlinear amplifier strand having complementarity to a nucleic acid strand, wherein the nucleic acid strand is either a docking strand or a primer strand,
(4) optionally removing unbound nonlinear amplifier strands,
(5) in either one or two steps amplifying the docking strand with rolling circle amplification and contacting the sample with labeled imager strands having complementarity to the docking strand or amplified strand,
(6) imaging the sample to detect bound labeled imager strands,
(7) removing the bound labeled imager strands, and
(8) optionally repeating steps (1)-(8), or any subset thereof.

Item 4. The method of item 3, wherein a polymerase is used for rolling circle amplification.

Item 5. The method of any one of items 3-4, wherein the nonlinear amplifier strand is combined with the target-specific binding partner linked to a nucleic acid strand before contacting the sample.

Item 6. The method of any one of items 3-5, wherein amplifying the docking strand with rolling circle amplification occurs separately from contacting the sample with labeled imager strands having complementarity to the docking strand or amplified strand.

Item 7. The method of any one of items 3-6, wherein amplifying the docking strand with rolling circle amplification occurs in the same step as contacting the sample with labeled imager strands having complementarity to the docking strand and wherein the imager strand optionally comprises a 3' modification to prevent amplification of the imager strand.

Item 8. The method of any one of items 3-5 or 7, wherein the imager strand is a circular imager strand for rolling circle amplification.

Item 9. The method of any one of items 3-7, wherein the imager strand is a linear imager strand that circularizes in the presence of the docking strand and a ligase.

Item 10. The method of any one of items 3-9, wherein the imager strand or amplifier strand comprises at least two regions that are complementary to the docking strand.

Item 11. The method of any one of items 3-10, wherein the labeled imager strands are linear strands.

Item 12. The method of any one of items 3-11, wherein the nonlinear amplifier strand is a circular strand.

Item 13. The method of any one of items 3-12, wherein the nonlinear amplifier strand becomes circular after ligation.

Item 14. A method to test a sample for the presence of one or more targets comprising
(1) contacting the sample with one or more target-specific binding partners, wherein each target-specific binding partner is linked to a nucleic acid strand, directly or indirectly, and wherein target-specific binding partners of different specificity are linked to different nucleic acid strands,
(2) optionally removing unbound target-specific binding partners,
(3) wherein the nucleic acid strand is a docking strand or a primer strand and if the nucleic acid is
  (a) a docking strand, optionally increasing the number of docking strands associated with each target-specific binding partner, or
  (b) a primer strand, optionally associating more than one docking strand with the primer strand,
(4) contacting the sample with labeled imager strands capable of binding a docking strand, directly or indirectly,
(5) optionally removing unbound labeled imager strands,
(6) imaging the sample to detect bound labeled imager strands, and
(7) optionally extinguishing signal from the bound labeled imager strand;
(8) optionally repeating steps (1)-(7) or any subset thereof.

Item 15. The method of item 14, wherein the sample is mounted to an optically transparent support.

Item 16. The method of any one of items 14-15, wherein after step (6) and after optionally performing step (7) the method further comprises increasing the number of docking strands associated with each target-specific binding partner and repeating steps (4), optionally (5), (6), and optionally (7).

Item 17. The method of any one of items item 14-16, wherein the method comprises at step (3) increasing the number of docking strands associated with each target-specific binding partner or associating more than one docking strand with the primer strand.

Item 18. The method of any one of items 1-17, where the increase in the number of docking strands associated with each target-specific binding partner is achieved using an enzyme and wherein the enzyme is optionally a polymerase.

Item 19. The method of any one of items 1-18, wherein enzymatically cleaving, modifying, or degrading unbound labeled imager strands is achieved by using an enzyme and wherein the enzyme is optionally a glycosylase, a restriction endonuclease, a nicking endonuclease, an RNase, and an enzyme that cleaves at a non-natural nucleotide.

Item 20. A method to test a sample mounted to an optically transparent support for the presence of one or more targets comprising
(1) contacting the sample with one or more target-specific binding partners, wherein each target-specific binding partner is linked to a nucleic acid strand, and wherein target-specific binding partners of different specificity are linked to different nucleic acid strands,
(2) optionally removing unbound target-specific binding partners,
(3) wherein the nucleic acid strand is a docking strand or a primer strand and optionally if the nucleic acid is (a) a docking strand, increasing the number of docking strands associated with each target-specific binding partner, or (b) a primer strand, associating more than one docking strand with the primer strand, (4) contacting the sample with labeled imager strands capable of binding a docking strand, directly or indirectly, (5) optionally removing unbound labeled imager strands, (6) optionally removing liquid to create a liquid-free sample, (7) affixing a second optically-transparent material parallel to the first support, and (8) imaging the sample to detect bound labeled imager strands.

Item 21. The method of item 20, where the second optically-transparent material is glass.

Item 22. The method of item 21, where the second optically-transparent material is plastic.

Item 23. The method of any one of items 20-22, wherein the second optically-transparent material is 5 microns to 5 mm, from 50 microns to 500 microns, or from 500 microns to 5 mm from the first support.

Item 24. The method of item 20, where the imaging is carried out with an upright microscope.

Item 25. A method to test a fixed sample mounted to an optically transparent support for the presence of one or more targets comprising (1) contacting the sample with one or more target-specific binding partners, wherein each target-specific binding partner is linked to a nucleic acid strand and wherein target-specific binding partners of different specificity are linked to different nucleic acid strands, (2) optionally removing unbound target-specific binding partners, (3) wherein the nucleic acid strand is a docking strand or a primer strand and if the nucleic acid is (a) a docking strand, increasing the number of docking strands associated with each target-specific binding partner, or (b) a primer strand, associating more than one docking strand with the primer strand, (4) contacting the sample with labeled imager strands capable of binding a docking strand, directly or indirectly, (5) optionally removing unbound labeled imager strands, (6) optionally removing liquid to create a liquid-free sample, (7) affixing a second optically-transparent material parallel to the first support, and (8) imaging the sample to detect bound labeled imager strands.

Item 26. A method comprising (1) contacting a sample being tested for the presence of one or more targets with one or more target-specific binding partners, wherein each target-specific binding partner is linked to a nucleic acid strand and wherein target-specific binding partners of different specificity are linked to different nucleic acid strands, (2) optionally removing unbound target-specific binding partners, (3) wherein the nucleic acid strand is a docking strand or a primer strand and optionally if the nucleic acid is (a) a docking strand, increasing the number of docking strands associated with each target-specific binding partner, or (b) a primer strand, associating more than one docking strand with the primer strand, (4) contacting the sample with labeled imager strands capable of binding a docking strand, directly or indirectly, (5) optionally removing unbound labeled imager strands, (6) imaging the sample to detect presence, location and number of bound labeled imager strands, (7) extinguishing signal from the bound labeled imager strand, and (8) repeating steps (3)-(6) or (3)-(7), with a labeled imager strand optionally having a unique nucleotide sequence relative to all other labeled imager strands.

Item 27. A composition comprising:

a sample bound to more than one target-specific binding partners, each binding partner bound to a nucleic acid strand and at least one docking strand stably bound to a labeled imager strand, directly or indirectly, wherein the nucleic acid strand is a docking strand or a primer strand if the nucleic acid is (a) a docking strand, increasing the number of docking strands associated with each target-specific binding partner, or (b) a primer strand, associating more than one docking strand with the primer strand.

Item 28. The composition of item 27, wherein the docking strand bound to a labeled imager strand, directly or indirectly, comprises at least 90% binding for 30 minutes.

Item 29. The composition of any one of items 27-28, wherein the (a) docking strand or (b) docking strand and any intermediate strand is 80 nucleotides or less, 70, 60, 50, 40, or 30 nucleotides or less.

Item 30. The composition of any one of items 27-29, wherein the imager strand is 60 nucleotides or less.

Item 31. A composition comprising:

(a) a composition employing a half-docking domain, wherein the composition comprises (i) at least one first binding partner-oligonucleotide conjugate comprising a binding partner linked to an oligonucleotide that comprises a half-docking domain, an optional stability domain, and optionally a spacer domain; (ii) at least one second binding partner-oligonucleotide conjugate comprising a binding partner linked to an oligonucleotide that comprises a half-docking domain, an optional stability domain, and optionally a spacer domain; wherein the stability domains of (a) (i) and (a) (ii) are complementary to each other, and wherein the half-docking domains of (a) (i) and (a) (ii) combine linearly to form a full docking domain; and (iii) at least one labeled imager strand or intermediate strand comprising a 5' domain, a 3' domain, and a linker domain located between the 5' domain and the 3' domain, wherein the 5' domain is complementary to the half-docking domain of (a) (i) and the 3' domain is complementary to the half-docking domain of (a)(ii), and wherein the labeled imager or intermediate strand is stably bound to the full docking domain and if an intermediate strand is used also providing a labeled imager strand; or (b) a composition employing a half-primer domain, wherein the composition comprises (i) at least one first binding partner-oligonucleotide conjugate comprising a binding partner linked to an oligonucleotide that comprises a half-primer domain, an optional stability domain, and optionally a spacer domain; (ii) at least one second binding partner-oligonucleotide conjugate comprising a binding partner linked to an oligonucleotide that comprises a half-primer domain, an optional stability domain, and optionally a spacer domain; wherein the stability domains of (b) (i) and (b) (ii) are complementary to each other, and wherein the half-primer domains of (b) (i) and (b) (ii) can combine linearly to form a full primer domain; (iii) at least one docking strand capable of being stably bound to the full primer domain; and (iv) at least one labeled imager strand capable of being stably bound to the docking strand or an intermediate strand capable of being stably bound to the docking strand and a labeled imager strand capable of being stably bound to the intermediate strand.

Item 32. The composition of item 31, wherein at least one imager strand is bound to a full docking domain for at least 30 minutes.

Item 33. The composition of item 31, wherein at least 70% of imager strands bound to full docking domains remain bound for at least 30 minutes.

Item 34. The composition of item 31, wherein at least 90% of imager strands bound to full docking domains are resistant to non-enzymatic buffer washes.

Item 35. A method to test a fixed sample mounted to an optically transparent support for the presence of one or more targets comprising
  (1) contacting the sample with one or more target-specific binding partners, wherein each target-specific binding partner is linked to a nucleic acid strand and wherein target-specific binding partners of different specificity are linked to different nucleic acid strands,
  (2) optionally removing unbound target-specific binding partners,
  (3) wherein the nucleic acid strand is a docking strand or a primer strand and optionally if the nucleic acid is
     (a) a docking strand, increasing the number of docking strands associated with each target-specific binding partner, or
     (b) a primer strand, associating more than one docking strand with the primer strand,
  (4) contacting the sample with labeled imager strands capable of binding a docking strand, directly or indirectly, wherein when used indirect binding is capable of occurring through an intermediate strand,
  (5) optionally removing unbound labeled imager strands,
  (6) imaging the sample to detect bound labeled imager strands,
  (7) extinguishing signal from the bound labeled imager strand,
  (8) contacting the sample with labeled imager strands having a nucleotide sequence that is not complementary to a docking strand or, when used, an intermediate strand,
  (9) optionally removing unbound labeled imager strands,
  (10) imaging the sample to detect bound labeled imager strands, and
  (11) optionally extinguishing signal from the bound labeled imager strand.

Item 36. A method to test a fixed sample mounted to an optically transparent support for the presence of one or more targets comprising
  (1) contacting the sample with one or more target-specific binding partners, wherein each target-specific binding partner is linked to a nucleic acid strand, and wherein target-specific binding partners of different specificity are linked to different nucleic acid strands,
  (2) optionally removing unbound target-specific binding partners,
  (3) wherein the nucleic acid strand is a docking strand or a primer strand and optionally if the nucleic acid is
     (a) a docking strand, increasing the number of docking strands associated with each target-specific binding partner, or
     (b) a primer strand, associating more than one docking strand with the primer strand,
  (4) contacting the sample with labeled imager strands having a nucleotide sequence that is not complementary to a docking strand or, when used, any intermediate strand,
  (5) optionally removing unbound labeled imager strands,
  (6) imaging the sample to detect presence, location and/or number of bound labeled imager strands,
  (7) extinguishing signal from the bound labeled imager strand.
  (8) contacting the sample with labeled imager strands capable of binding a docking strand, directly or indirectly, wherein, when used, indirect binding is capable of occurring through an intermediate strand,
  (9) optionally removing unbound labeled imager strands,
  (10) imaging the sample to detect presence, location, and/or number of bound labeled imager strands, and
  (11) optionally extinguishing signal from the bound labeled imager strand.

Item 37. The method of either one of items 35 or 36, wherein the method further comprises repeating steps (4)-(11).

Item 38. The method of either one of items 35-37, wherein the method further comprises repeating steps to detect binding of additional noncomplementary imaging strands.

Item 39. The method of any one of items 35-38, wherein the labeled imager strands capable of binding a docking strand, directly or indirectly, used in the repeated steps optionally has a unique nucleotide sequence relative to at least one other labeled imager strands capable of binding another docking strand, directly or indirectly.

Item 40. A composition comprising
  (1) a label,
  (2) a first nucleic acid domain, a second nucleic acid domain, and a third nucleic acid domain, wherein each nucleic acid domain is from 1 to 9 nucleotides long,
  (3) a first linking moiety linking the first nucleic acid domain and the second nucleic acid domain and
  (4) a second linking moiety linking the second nucleic acid domain and the third nucleic acid domain, wherein both linking moieties are independently chosen from (a) an abasic site with an intact phosphodiester backbone, (b) a linker cleavable by a nucleic acid glycosylase, (c) non-natural nucleotides, or (d) restriction site or a nicking site.

Item 41. The composition of item 40, wherein additional nucleic acid domains are linked by additional linking moieties.

Item 42. The composition of any one of items 40-41, wherein at least one linking moiety is an abasic site (apyrimidinic) with an intact phosphodiester backbone.

Item 43. The composition of any one of items 40-42, wherein at least one linking moiety is susceptible to cleavage from Endonuclease VIII.

Item 44. The composition of any one of items 40-43, wherein the nucleic acid domains comprise DNA.

Item 45. The composition of any one of items 40-44, wherein the nucleic acid domains comprise RNA.

Item 46. The composition of any one of items 40-45, wherein at least one linking moiety comprises at least one non-natural nucleotide.

Item 47. The composition of any one of items 40-46, wherein at least one linking moiety comprises 8-oxoguanine.

Item 48. A method to test a sample for the presence of one or more targets comprising
 (1) contacting the sample with one or more target-specific binding partners, wherein each target-specific binding partner is linked to a nucleic acid strand, directly or indirectly and wherein target-specific binding partners of different specificity are linked to different nucleic acid strands,
 (2) optionally removing unbound target-specific binding partners,
 (3) wherein the nucleic acid strand is a docking strand or a primer strand and if the nucleic acid is
  (a) a docking strand, increasing the number of docking strands associated with each target-specific binding partner, or
  (b) a primer strand, associating more than one docking strand with the primer strand,
 (4) contacting the sample with labeled imager strands capable of binding a docking strand, directly or indirectly, wherein the labeled imager strands comprise the composition of any one of items 34-41,
 (5) optionally removing unbound labeled imager strands,
 (6) imaging the sample to detect bound labeled imager strands,
 (7) removing the bound labeled imager strands from the docking strands, wherein the labeled imager strands are removed from the docking strands by enzymatically cleaving, modifying, or degrading the labeled imager nucleic acids,
 (8) optionally repeating steps (1)-(7), or any subset thereof.

Item 49. The method of item 48, wherein the labeled imager nucleic acids are removed by enzymatically cleaving the labeled imager strand.

Item 50. A method to test a sample for the presence of one or more targets comprising
 (1) treating the sample to expose one or more previously unavailable targets,
 (2) contacting the sample with one or more target-specific binding partners, wherein each target-specific binding partner is linked to a nucleic acid strand and wherein target-specific binding partners of different specificity are linked to different nucleic acid strands,
 (3) optionally removing unbound target-specific binding partners,
 (4) wherein the nucleic acid strand is a docking strand or a primer strand and optionally if the nucleic acid is
  (a) a docking strand, increasing the number of docking strands associated with each target-specific binding partner, or
  (b) a primer strand, associating more than one docking strand with the primer strand,
 (5) contacting the sample with labeled imager strands capable of binding a docking strand, directly or indirectly,
 (6) optionally removing unbound labeled imager strands,
 (7) imaging the sample to detect bound labeled imager strands,
 (8) extinguishing signal from the bound labeled imager strand, and
 (9) optionally repeating steps (1)-(8), each time (a) exposing a different set of previously unavailable targets (b) using one or more different target-specific binding partners and (c) using a labeled imager strand having a unique nucleotide sequence relative to at least one other labeled imager strand.

Item 51. A method to test a fixed sample mounted to a first optically transparent support for the presence of one or more targets comprising
 (1) contacting the sample with one or more target-specific binding partners, wherein each target-specific binding partner is linked to a nucleic acid strand and wherein target-specific binding partners of different specificity are linked to different nucleic acid strands,
 (2) optionally removing unbound target-specific binding partners,
 (3) wherein the nucleic acid strand is a docking strand or a primer strand and optionally if the nucleic acid is
  (a) a docking strand, increasing the number of docking strands associated with each target-specific binding partner, or
  (b) a primer strand, associating more than one docking strand with the primer strand,
 (4) in an imaging chamber (such as a flow cell), contacting the sample with labeled imager strands capable of binding a docking strand, directly or indirectly,
 (5) optionally removing unbound labeled imager strands,
 (6) imaging the sample to detect presence, location, and/or number of bound labeled imager strands,
 (7) extinguishing signal from the bound labeled imager strand, and
 (8) repeating steps (4)-(6) or (4)-(7), at least once with a labeled imager strand optionally having a unique nucleotide sequence relative to at least one other labeled imager strands.

Item 52. The method of item 51, wherein the imaging chamber is removed after an imaging step and before repeating steps (4)-(6) or (4)-(7).

Item 53. The method of any one of items 51-52, wherein the imaging chamber does not permit fluid flow and the imaging chamber is removed after an imaging step and before repeating steps (4)-(6) or (4)-(7).

Item 54. The method of any one of items 51-53, where the flow cell is formed with a second optically-transparent material.

Item 55. The method of item 54, where the second optically-transparent material comprises glass.

Item 56. The method of item 54, where the second optically-transparent material comprises plastic.

Item 57. The method of any one of items 51-52, wherein the imaging chamber (such as a flow cell) comprises a gasket with at least one fluid inlet and/or outlet ports.

Item 58. The method of any one of items 54-56, wherein the flow cell comprises a second optically-transparent material parallel to the first optically-transparent support.

Item 59. The method of any one of items 1-26, 35-39, or 48-58, wherein all fluidic exchange steps are performed using a fluidic system comprising electronic, and/or pneumatic, and/or hydraulic, and/or electro-fluidic actuators and systems.

Item 60. The method of item 59, wherein the fluidic system is controlled by software.

Item 61. The method of item 59, wherein the fluidic system is automatically controlled by software synchronizing steps (1 and/or 2 and/or 3 and/or 4 and/or 5, and/or 7) with the imaging step (6), with reference to the numbering provided in item 1.

Item 62. The method of item 59, wherein the fluidic system is controlled by software synchronizing the steps (1 and/or 2 and/or 3 and/or 4 and/or 5, and/or 7) with the imaging step (6) by communicating with the imaging software, with reference to the numbering provided in item 1.

Item 63. The method of any one of items 59-62, wherein all fluidic steps are performed while the sample is on the imaging device.

Item 64. The method of any one of items 59-63, wherein steps 4, 5, and 7 are performed while the sample is on the imaging device, with reference to the numbering provided in item 1.

Item 65. The method of any one of items 59-64, wherein the sample is fixed in a disposable imaging chamber (such as a flow cell).

Item 66. The method of any one of items 59-65, wherein the sample is fixed in a reusable imaging chamber (such as a flow cell).

Item 67. A kit comprising:
(1) one or more reagent(s) including but not limited to target-specific binding partners linked to nucleic acid strands, wherein target-specific binding partners of different specificity are linked to different nucleic acid strands, labeled imager strands, buffers, amplification reagents, and/or reagents to remove bound imager strands, wherein the nucleic acid strand is a docking strand or a primer strand and if the nucleic acid strand is a docking strand, increasing the number of docking strands associated with each target-specific binding partner, or if the nucleic acid is a primer strand, associating more than one docking strand with the primer strand,
(2) a fluidic system to perform all fluid exchange steps, a software to control the fluidic system and time and/or synchronize the fluidic steps with the imaging steps,
(3) a flow cell to affix on the sample of interest with at least one optically transparent side to allow imaging of the sample.

Item 68. The kit of item 67, wherein the flow cell is a disposable flow cell.

Item 69. The method of any one of items 1-26, 35-39, or 48-66, wherein imaging the sample to detect bound labeled imager strands detects the presence of bound labeled imager strands.

Item 70. The method of any one of items 1-26, 35-39, or 48-66, wherein imaging the sample to detect bound labeled imager strands detects the presence, location, and/or number of bound labeled imager strands.

Item 71. The method of any one of items 70, wherein the method comprises imaging the sample to detect and/or measure a background signal and subtracting the background signal from the image of the sample to detect bound labeled imager strands.

Item 72. The method of item 71, wherein the background signal comprises autofluorescence.

Item 73. The method of any one of items 71-72, wherein the background comprises residual fluorescence associated with incompletely extinguishing signal from the bound labeled imager strands.

Item 74. The method of any one of items 71-73, wherein the background signal is measured before the image of the sample to detect bound labeled imager strands.

Item 75. The method of any one of items 71-74, wherein the background signal is measured after the image of the sample to detect bound labeled imager strands.

Item 76. The method of any one of items 1-26, 35-39, or 48-75, wherein the sample is a fixed sample.

Item 77. The method of any one of items 1-26, 35-39, or 48-76, wherein the sample is a cell, cell lysate, tissue, tissue lysate, bodily fluid, and/or a whole organism.

Item 78. The method of any one of items 1-26, 35-39, or 48-77, wherein the method is useful for identifying a biomarker.

Item 79. The method of item 78, wherein at least 96 samples are imaged and data analysis performed on those samples.

Item 80. The method of any one of items 78-79, wherein at least 15 targets are tested for using corresponding target-specific binding partners for each target.

Item 81. The method of any one of items 1-26, 35-39, or 48-80, wherein the imaging is performed using a light microscope, fluorescence microscope including widefield, confocal (line and point scanning, spinning disk), total internal reflection (TIR), stimulated emission depletion (STED), light-sheet illumination, structured illumination (SIM), and expansion microscopy.

Item 82. The method of any one of items 1-26, 35-39, or 48-81, wherein the docking strand bound to a labeled imager strand, directly or indirectly, comprises at least 90% binding for 30 minutes.

Item 83. The method of any one of items 1-26, 35-39, or 48-82, wherein the target-specific binding partner is directly linked to a docking strand.

Item 84. The method of any one of items 1-26, 35-39, or 48-83, wherein the target-specific binding partner is indirectly linked to a docking strand through a primer strand.

Item 85. The method of any one of items 1-26, 35-39, or 48-84, wherein the docking strand binds the imager strand directly.

Item 86. The method of any one of items 1-26, 35-39, or 48-85, wherein the docking strand has complementarity to the imager strand.

Item 87. The method of any one of items 1-26, 35-39, or 48-86, wherein the docking strand binds the imager strand indirectly through an intermediate strand.

Item 88. The method of any one of items 1-26, 35-39, or 48-87 or the kit of items 67-68, wherein the imager strand and/or the intermediate strand comprises at least one U capable of cleavage by USER.

Item 89. The method of any one of items 1-26, 35-39, or 48-88 or the kit of items 66-67 and 88, wherein the imager strand and/or intermediate strand comprises at least one abasic site.

Item 90. The method of any one of items 1-25, 34-38, or 47-89 or the kit of items 66-67 and 89, wherein the imager strand and/or the intermediate strand comprise a hairpin.

Item 91. The method of any one of items 1-25, 34-38, or 47-90 or the kit of items 66-67 or 88-90, wherein the imager strand and/or the intermediate strand comprise a hairpin with a clamp.

Item 92. The method of any one of items 1-25, 34-38, or 47-91, wherein at least two targets are imaged using at least two labels in the same imaging step.

Item 93. The method of any one of items 1-25, 34-38, or 47-92, wherein at least two targets are imaged using the same label in different imaging steps.

Item 94. The method of any one of items 1-25, 34-38, or 47-93, wherein at least two targets are imaged using at least two labels, the signal extinguished, and then at least one more target is imaged using at least one of the same labels, wherein the imaging steps may be performed in either order.

Item 95. The method of any one of items 1-25, 34-38, or 47-93, wherein extinguishing the signal from the bound labeled imager strand comprises removing the nucleic acid strand from the target-specific binding partner.

Item 96. The method of item 95, wherein removing the nucleic acid strand comprises enzymatically cleaving, modifying, or degrading the nucleic acid strand linked to the target specific binding partner.

Item 97. The method of item 97, wherein the nucleic acid strand is docking strand.

Item 98. The method of item 97, wherein the nucleic acid strand is a primer strand.

Item 99. The method of any one of items 1-25, 34-38, or 47-94, wherein if the nucleic acid strand linked to the target specific binding partner is a primer strand, extinguishing the signal from the bound labeled imager strand comprises removing the docking strand from the primer strand.

Item 100. The method of item 99, wherein removing the docking strand comprises enzymatically cleaving, modifying, or degrading the docking strand.

Item 101. The method of any one of items 1-25, 34-38, or 47-94, wherein extinguishing the signal from the bound labeled imager strand comprises removing the imager strand.

Item 102. The method of any one of items 1-25, 34-38, or 47-94, wherein removing the imager strand comprises enzymatically cleaving, modifying, or degrading the imager strand.

Item 103. The method of any one of items 1-25, 34-38, or 47-94, wherein extinguishing the signal from the bound labeled imager strand comprises removing the label from the imager strand.

EQUIVALENTS

The foregoing written specification is sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

What is claimed is:

1. A method for detecting two or more targets, comprising:
   (1) contacting a sample being tested for the presence of two or more targets with two or more target-specific binding partners, wherein each target-specific binding partner is linked to a docking strand and wherein target-specific binding partners of different specificity are linked to different docking strands;
   (2) optionally removing unbound target-specific binding partners;
   (3) contacting the sample with enzyme-labeled strands capable of binding a docking strand, wherein the enzyme-labeled strands comprise horseradish peroxidase (HRP)-labeled strands;
   (4) optionally removing unbound enzyme-labeled strands;
   (5) contacting the sample with a substrate for the enzyme comprising a tyramide moiety linked to a fluorophore;
   (6) allowing an enzymatic reaction to produce an amplification product;
   (7) quenching the enzymatic reaction by removing the bound enzyme-labeled strands;
   (8) repeating steps (3)-(7),
   (9) after step (8), imaging the sample to detect the presence or absence of two or more targets; and
   (10) optionally repeating at least some of steps (1)-(9).

2. The method of claim 1, wherein the bound enzyme-labeled strands are removed by enzymatically cleaving, modifying, or degrading the enzyme-labeled strands.

3. The method of claim 1, wherein the bound enzyme-labeled strands are removed by photochemically cleaving the enzyme-labeled strands.

4. The method of claim 1, further comprising removing or inactivating the amplification product after imaging.

5. The method of claim 1, wherein the enzyme is capable of converting the tyramide moiety to an activated state capable of binding to tyrosine residues, resulting in deposition of the amplification product on or near the target.

6. The method of claim 1, wherein the target-specific binding partner is an antibody or a fragment thereof.

7. The method of claim 1, wherein the docking strand is a nucleic acid strand.

8. The method of claim 7, wherein the enzyme-labeled strand has a nucleic acid sequence complementary to a corresponding sequence of the docking strand.

9. The method of claim 1, wherein at least 5 targets are tested for, using a corresponding target-specific binding partner for each target.

10. The method of claim 1, wherein at least 3 targets are imaged using at least 3 labels in the same imaging step.

11. The method of claim 1, wherein at least 3 targets are imaged using at least 3 labels, the signal extinguished, and then at least one more target is imaged using at least one of the same labels, wherein the imaging steps may be performed in either order.

12. A method for detecting one or more targets, comprising:
   (1) contacting a sample having a target site being tested for the presence of one or more targets with one or more target-specific binding partners, wherein each target-specific binding partner is linked to a docking strand, and wherein target-specific binding partners of different specificity are linked to different docking strands;
   (2) optionally removing unbound target-specific binding partners;
   (3) contacting the sample with enzyme-labeled strands having a nucleotide sequence that is complementary to a docking strand, wherein the enzyme-labeled strands comprise horseradish peroxidase (HRP)-labeled strands;
   (4) optionally removing unbound enzyme-labeled strands;
   (5) contacting the sample with tyramide-bound docking strands, wherein the docking strand is a barcode for an imager strand;
   (6) enzymatically converting the tyramide moiety into an activated state, wherein the activated state results in a covalent linkage of the tyramide-bound docking strand to the target site;
   (7) removing the enzyme-labeled strands;
   (8) optionally repeating a subset of steps 3-7;

(9) contacting the sample with one or more imager strands;

(10) imaging the sample to detect the presence or absence of one or more targets; and

(11) optionally repeating at least some of steps 3-10.

13. The method of claim 12, wherein the docking strand of the tyramide-bound docking strands comprises a nucleotide sequence complementary to the imager strand.

14. The method of claim 12, wherein the docking strand linked to the target-specific binding partner introduced in step (1) is different from the docking strand of the tyramide-bound docking strands introduced in step (5).

15. A method for detecting two or more targets, comprising:

(1) contacting a sample being tested for the presence of two or more targets with two or more target-specific binding partners, wherein each target-specific binding partner is linked to a docking strand and wherein target-specific binding partners of different specificity are linked to different docking strands;

(2) optionally removing unbound target-specific binding partners;

(3) contacting the sample with enzyme-labeled strands capable of binding a docking strand wherein the enzyme-labeled strands comprise horseradish peroxidase (HRP)-labeled strands;

(4) optionally removing unbound enzyme-labeled strands;

(5) contacting the sample with a substrate for the enzyme comprising a tyramide moiety linked to a fluorophore;

(6) allowing an enzymatic reaction to produce an amplification product;

(7) quenching the enzymatic reaction by removing the bound enzyme-labeled strands;

(8) imaging the sample to detect the presence or absence of two or more targets; and (9) optionally repeating at least some of steps (1)-(8).

* * * * *